(12) United States Patent
Thorne

(10) Patent No.: US 10,962,544 B2
(45) Date of Patent: Mar. 30, 2021

(54) METHODS OF PREDICTING PROGRESSION OF BARRETT'S ESOPHAGUS

(71) Applicant: CERNOSTICS, INC., Bethlehem, PA (US)

(72) Inventor: Rebecca J. Thorne, Pittsburgh, PA (US)

(73) Assignee: Cernostics, Inc., Pittsburgh, PA (US)

( * ) Notice: Subject to any disclaimer, the term of this patent is extended or adjusted under 35 U.S.C. 154(b) by 356 days.

(21) Appl. No.: 15/778,403

(22) PCT Filed: Nov. 23, 2016

(86) PCT No.: PCT/US2016/063482
§ 371 (c)(1),
(2) Date: May 23, 2018

(87) PCT Pub. No.: WO2017/091658
PCT Pub. Date: Jun. 1, 2017

(65) Prior Publication Data
US 2018/0348226 A1    Dec. 6, 2018

Related U.S. Application Data

(60) Provisional application No. 62/260,010, filed on Nov. 25, 2015.

(51) Int. Cl.
*G01N 33/574* (2006.01)

(52) U.S. Cl.
CPC .. *G01N 33/57484* (2013.01); *G01N 33/57446* (2013.01); *G01N 2800/56* (2013.01)

(58) Field of Classification Search
None
See application file for complete search history.

(56) References Cited

U.S. PATENT DOCUMENTS

| | | |
|---|---|---|
| 5,989,835 A | 11/1999 | Dunlay et al. |
| 6,025,128 A | 2/2000 | Veltri et al. |
| 6,103,479 A | 8/2000 | Taylor |
| 6,218,122 B1 | 4/2001 | Friend et al. |
| 6,416,959 B1 | 7/2002 | Giuliano et al. |
| 6,573,039 B1 | 6/2003 | Dunlay et al. |
| 6,633,662 B2 | 10/2003 | Ravkin |
| 6,671,624 B1 | 12/2003 | Dunlay et al. |
| 6,727,071 B1 | 4/2004 | Dunlay et al. |
| 6,759,206 B1 | 7/2004 | Rubin et al. |
| 6,763,307 B2 | 7/2004 | Berg et al. |
| 6,875,578 B2 | 4/2005 | Giuliano et al. |
| 6,939,720 B2 | 9/2005 | Chandler et al. |
| 6,986,993 B1 | 1/2006 | Ghosh et al. |
| 7,060,445 B1 | 6/2006 | Dunlay et al. |
| 7,117,098 B1 | 10/2006 | Dunlay et al. |
| 7,130,746 B2 | 10/2006 | Friend et al. |
| 7,219,016 B2 | 5/2007 | Rimm et al. |
| 7,274,809 B2 | 9/2007 | MacAulay et al. |
| 7,282,347 B2 | 10/2007 | Bjorn et al. |
| 8,114,615 B2 | 2/2012 | Gough et al. |
| 8,597,899 B2 | 12/2013 | Gough et al. |
| 2001/0029019 A1 | 10/2001 | Waldman et al. |
| 2001/0039015 A1 | 11/2001 | Sauter |
| 2003/0059093 A1 | 3/2003 | Rosania et al. |
| 2003/0096243 A1 | 5/2003 | Busa |
| 2004/0043436 A1 | 3/2004 | Vlahou et al. |
| 2004/0101912 A1 | 5/2004 | Rubin et al. |
| 2004/0157242 A1 | 8/2004 | Ivey et al. |
| 2006/0014238 A1 | 1/2006 | Gholap et al. |
| 2006/0094868 A1 | 5/2006 | Giuliano et al. |
| 2006/0188140 A1 | 8/2006 | Gholap et al. |
| 2006/0199210 A1 | 9/2006 | Weichselbaum et al. |
| 2007/0019854 A1 | 1/2007 | Gholap et al. |
| 2007/0099219 A1 | 5/2007 | Teverovskiy et al. |
| 2007/0212721 A1 | 9/2007 | Fischer et al. |
| 2008/0008349 A1 | 1/2008 | Binnig et al. |
| 2008/0015786 A1 | 1/2008 | Ramer et al. |
| 2008/0057514 A1 | 3/2008 | Goldenring |
| 2009/0170091 A1 | 7/2009 | Giuliano et al. |
| 2009/0317836 A1 | 12/2009 | Kuhn et al. |
| 2013/0078632 A1 | 3/2013 | Krishnadath |

(Continued)

FOREIGN PATENT DOCUMENTS

| | | |
|---|---|---|
| WO | 1992017853 A | 10/1992 |
| WO | 1998035609 A | 8/1998 |

(Continued)

OTHER PUBLICATIONS

Hamilton, PW et al. "Digital pathology and image analysis in tissue biomarker research". Methods 70 (2014) 59-73. (Year: 2014).*
Szczurek, AT et al. "Single molecule localization microscopy of the distribution of chromatin using Hoechst and DAPI fluorescent probes". Nucleus, 5:4, 331-340 (Year: 2014).*
Abdel-Latif et al., "NF-kB Activation in Esophageal Adenocarcinoma: Relationship to Barrett's Metaplasia, Survival, and Response to Neoadjuvant Chemoradiotherapy," Annals of Surgery, Apr. 2004, vol. 239: No. 4, pp. 491-500.
Bobryshev et al., "Dendritic Cell-Associated Immune Inflammation of Cardiac Mucosa: A Possible Factor in the Formation of Barrett's Esophagus," J Gastrointest Surg, 2009, 13, pp. 442-450.
Brabender et al., "A Multigene Expression Panel for the Molecular Diagnosis of Barrett's Esophagus and Barrett's Adenacarcinoma of the Esophagus," Oncogene, 2004, vol. 23, pp. 4780-4788.
Cappello et al., "CDIa Expression by Barrett's Metaplasia of Gastric Type May Help to Predict Its Evolution Towards Cancer," British Journal of Cancer, 2005, vol. 92, pp. 888-890.
Ling et al., "HIF-1α mRNA is Not Associated with Histopathological Regression Following Neoadjuvant Chemoradiation in Esophageal Cancer," Anticancer Research, 2006, vol. 26, pp. 4505-4510.
Osterheld et al., "beta-Catenin Expression and Its Association With Prognostic Factors in Adenocarcinoma Developed in Barrett Esophagus," Am J Clin Pathol 2002, 117, pp. 451-456.

(Continued)

*Primary Examiner* — Joanne Hama
*Assistant Examiner* — Scott T. Humbarger
(74) *Attorney, Agent, or Firm* — Troutman Pepper Hamilton Sanders LLP

(57) ABSTRACT

Embodiments described herein provide methods of determining a risk of progression of Barrett's esophagus in a subject, classifying Barrett's esophagus in a subject, and detecting a field effect associated with malignant transformation of an esophagus of a subject suffering from Barrett's esophagus. The disclosure also provides kits for determining a risk of progression of Barrett's esophagus in a subject and classifying Barrett's esophagus in a subject.

11 Claims, 59 Drawing Sheets

(56) References Cited

U.S. PATENT DOCUMENTS

| | | | | |
|---|---|---|---|---|
| 2014/0141988 A1* | 5/2014 | Thorne | ............ | G01N 33/57407 506/9 |
| 2014/0162888 A1 | 6/2014 | Kuslich et al. | | |

FOREIGN PATENT DOCUMENTS

| | | |
|---|---|---|
| WO | 2000070528 A | 11/2000 |
| WO | 2001033228 A2 | 5/2001 |
| WO | 2001074405 A1 | 10/2001 |
| WO | 2001081895 A2 | 11/2001 |
| WO | 2004076643 A2 | 9/2004 |
| WO | 2004094992 A2 | 11/2004 |
| WO | 2005050556 A2 | 6/2005 |
| WO | 2005050563 A3 | 6/2005 |
| WO | 2005091203 A2 | 9/2005 |
| WO | 2006020627 A1 | 2/2006 |
| WO | 2006036726 A1 | 4/2006 |
| WO | 2006037622 A1 | 4/2006 |
| WO | 2007044944 A1 | 4/2007 |
| WO | 2007045896 A1 | 4/2007 |
| WO | 2007081968 A1 | 7/2007 |
| WO | 2007092547 A2 | 8/2007 |
| WO | 2007130677 A2 | 11/2007 |
| WO | 2007136724 A2 | 11/2007 |
| WO | 2008060483 A2 | 5/2008 |
| WO | 2009105533 A2 | 8/2009 |
| WO | 2010121266 A1 | 10/2010 |
| WO | 2011088226 A2 | 7/2011 |
| WO | 2012125807 A2 | 9/2012 |
| WO | 2017091658 A1 | 6/2017 |

OTHER PUBLICATIONS

Phillips et al., "Cdx2 as a Marker of Epithelial Intestinal Differentiation in the Esophagus," Am J Surg Pathol, Nov. 2003, vol. 27: No. 11, pp. 1442-1447.
Rauser et al., "High Number of CD45RO+ Tumor Infiltrating Lymphocytes is an Independent Prognostic Factor in Non-Metastasized (Stage I-IIA) Esophageal Adenocarinoma," BMC Cancer 2010, 10, pp. 608-616.
Rossi et al., "HER-2/neu in Barrett Esophagus: A Comparative Study Between Histology, Immunohistochemistry, and Fluorescence In Situ Hybridization," Diagn Mol Pathol, vol. 15: No. 3, Sep. 2006, pp. 125-130.
Sarbia et al., "Distinction Between Intestinal Metaplasia in the Cardia and in Barett's Esophagus: The Role of Histology and Immunohistochemistry," Institute of Pathology; Human Pathology, vol. 35: No. 3, Mar. 2004, pp. 371-376.
Shi et al., "p16, Cyclin D1, Ki-67, and AMACR as Markers for Dysplasia in Barrett Esophagus," Appl Immunohistochem Mol Morphol, Oct. 2008;vol. 16: No. 5, pp. 447-452.
Sikkema et al., "Aneuploidy and Overexpression of Ki67 and p53 as Markers for Neoplastic Progression in Barett's Esophagus: A Case-Control Study," The American Journal of Gastroenterology, Jul. 28, 2009, vol. 104, pp. 2673-2680.
Aldulaimi et al., "Barrett's Surveillance is Worthwhile and Detects Curable Cancers. A Prospective Cohort Study Addressing Cancer Incidence, Treatment Outcome and Survival," Eur J. Gastroenterol Hepatol., 17(9):943-950 (2005).
Allameh et al., "Immunohistochemical Analysis of Selected Molecular Markers in Esophagus Precancerous, Adenocarcinoma and Squamous Cell Carcinoma in Iranian Subjects," CancerEpidemiology, 33(1):79-84 (2009).
Blankenstein et al., "Modular Concept of a Laboratory on a Chip for Chemical and Biochemical Analysis," Biosensors & Bioelectronics, Elsevier Science Publishers, Barking, GB, vol. 13, No. 3/4, 1998, pp. 427-438, XP000700154, ISSN: 0956-5663.
Critchley-Thorne et al., "A Tissue Systems Pathology Assay for High-Risk Barrett's Esophagus," Cancer Epidemiol Biomarkers Prev, 25(6): 958-968 (2016).
Critchley-Thorne et al., "A Tissue Systems Pathology Test Detects Abnormalities Associated with Prevalent High-Grade Dysplasia and Esophageal Cancer in Barrett's Esophagus," Cancer Epidemiol Biomarkers Prev, 26(2): 240-248 (2017).
European Search Report for corresponding European Application No. 12757085.1 dated Mar. 6, 2015.
Gao et al., "p53 Tumor Suppressor Gene Mutation in Early Esophageal Precancerous Lesions and Carcinoma Among High-Risk Populations in Henan, China," Cancer Research, 54:4342-4346 (1994).
Giuliano et al., "Optimal Characteristics of Protein-Protein Interaction Biosensors for Cellular Systems Biology Profiling," Preprint to be published in High Content Screening: Science, Technology and Applications, ed. Haney, S.A., Wiley Publishers, (2007), Retrieved from the Internet: url:http://www.cellumen.com/downloads/cellumen-2007-Giuliano-PPIBs.pdf; [retrieved on Sep. 1, 2008].
Giuliano et al., "Systems Cell Biology Based on High-Content Screening," 1Vlethods in Enzymology, Elsevier Academic Press, Inc., pp. 601-619 (2006), XP009097131, ISSN: 0-12-182819-0(H).
Giuliano et al., "Systems Cell Biology Knowledge Created from High Content Screening," Assay and Drug Development Technologies, 3(5):501-514 (Oct. 2005) XP002473054, ISSN:1540-658X.
Helden et al., "Representing and Analysing Molecular and Cellular Function Using the Computer," Biological Chemistry vol. 381, No. 9/10, Sep. 2000, pp. 921-935, XP008032491, ISSN: 1431-6730.
Hormi-Carver et al., "Molecular Markers and Genetics in Cancer Development," Surg Oneal Clin N Am, 18(3):453-467 (2009).
International Preliminary Report on Patentability for PCT/US2007/011865 dated Nov. 18, 2008.
International Preliminary Report on Patentability for PCT/US2007/023678 dated May 22, 2009.
International Preliminary Report on Patentability for PCT/US2012/029198 dated Sep. 17, 2013.
International Search Report and Written Opinion for PCT/US2007/011865 dated Jan. 11, 2008.
International Search Report and Written Opinion for PCT/US2007/023678 dated Aug. 29, 2008.
International Search Report and Written Opinion for PCT/US2012/029198 dated Oct. 29, 2012.
International Search Report and Written Opinion for PCT/US2016/063482 dated Feb. 1, 2017.
Kyrgidis et al., "Research Review: New Molecular Concepts of Barrett's Esophagus: Clinical Implications and Biomarkers," Journal of Surgical Research, 125(2): 189-212 (2005).
Macdonald et al., Developmental Cellvol. 17, Issue 1, Jul. 21, 2009, pp. 9-26. "WnU13-Catenin Signaling: Components, Mechanisms, and Diseases".
Malpica et al., "Applying Watershed Algorithms to the Segmentation of Clustered Nuclei," Cytometry: The Journal of the Society for Analytical Cytology, U.S. Aug. 1, 1997, pp. 289-297, XP002242990, ISSN: 0196-4763.
Minghetti, "Cyclooxygenase-2 (COX-2) in inflammatory and degenerative brain diseases," J. Neuropathol Exp Neurol. (Sep. 2004); 63(9):901-10.
Mulrane et al., "Expert Reviews: Automated Image Analysis in Histopathology: A Valuable Tool in Medical Diagnostics," Expert Rev. Mol. Diagn., 8(6): 707-725 (2008).
Prichard et al., "TissueCyperTM : A Systems Biology Approach to Anatomic Pathology," J Pathol Inform, 1:48, pp. 1-14 (2015).
Van Dekken et al., "Immunohistochemical Evaluation of a Panel of Tumor Cell Markers During Malignant Progression in Barrett Esophagus," Am J Clin Pathol., 130(5):745-753 (2008).
Buttar et al., "The Effect of Selective Cyclooxygenase-2 Inhibition in Barrett's Esophagus Epithelium: An In Vitro Study," Journal of the National Cancer Institute, vol. 94, No. 6, Mar. 20, 2002.
Davison et al., "Independent Blinded Validation of a Tissue Systems Pathology Test to Predict Progression in Patients With Barrett's Esophagus," The American Journal of Gastroenterology, Feb. 18, 2020, pp. 1-10.
Ell et al., "Endoscopic Mucosal Resection of Early Cancer and High-Grade Dysplasia in Barrett's Esophagus," Gastroenterology, Apr. 2000, 118:670-677.
Frei et al., "Independent Validation of a Tissue Systems Pathology Assay to Predict Future Progression in Nondysplastic Barrett's

(56) References Cited

OTHER PUBLICATIONS

Esophagus: A Spatial-Temporal Analysis," Clinical and Translational Gastroenterology, Oct. 8 2020, vol. 11, pp. 1-8.
Frei et al., "Tissue Systems Pathology Test Objectively Risk Stratifies Barrett's Esophagus Patients With Low-Grade Dysplasia," Am. J. Gastroenterol., Nov. 18, 2020, vol. 00, pp. 1-8.
Gail et al., "Projecting Individualized Probabilities of Developing Breast Cancer for White Females Who Are Being Examined Annually," Journal of National Cancer Institute, vol. 81:1879-1886, Dec. 20, 1989.
Levenson et al., "Multispectral Imaging and Pathology: Seeing and Doing More," Expert Opinion Med Diagn. 2008 2 (9): 1067-1081.
Prasad et al., "Predictors of Progression in Barrett's Esophagus: Current Knowledge and Future Directions," Am J Gastroenterol. Jul. 2010; 105(7): 1490-1502.
Qin et al., "Predicting Progression in Barrett's Esophagus: Is the Holy Grail Within Reach?" Am. J. Gastroenterol., Apr. 14, 2020; 115:841-842.
Seibel et al., "Tethered Capsule Endoscopy, A Low-Cost and High-Performance Alternative Technology for the Screening of Esophageal Cancer and Barrett's Esophagus," IEEE Transactions on Biomedical Engineering, vol. 55, No. 3, Mar. 2008, pp. 1032-1042.

\* cited by examiner

E

| Patient Group | Comparison | Hazard Ratio (95% C.I.) | Odds Ratio (95% C.I.) |
|---|---|---|---|
| All 4 Institutions Combined | High vs. low risk | 14.73 (6.55, 33.16) | 29.77 (7.32, 121.10) |
| | Inter vs. low risk | 4.19 (1.52, 11.57) | 7.65 (1.89, 31.07) |
| US Patients | High vs. low risk | 14.35 (4.23, 48.69) | 19.34 (3.31, 112.88) |
| | Inter vs. low risk | 4.62 (1.16, 18.48) | 8.28 (1.39, 49.33) |
| Netherlands Patients | High vs. low risk | 10.82 (3.58, 32.64) | 55.25 (4.47, 682.43) |
| | Inter vs. low risk | 4.79 (1.04, 22.02) | 7.36 (0.74, 73.58) |

| Patient Group | Comparison | Hazard Ratio (95% C.I.) | Odds Ratio (95% C.I.) |
|---|---|---|---|
| All 4 Institutions Combined | High vs. low risk | 9.42 (4.61, 19.24) | 9.40 (2.65, 33.28) |
| | Inter vs. low risk | 2.45 (0.99, 6.07) | 2.35 (0.66, 8.41) |
| US Patients | High vs. low risk | 10.79 (2.40, 48.59) | 8.87 (0.91, 86.36) |
| | Inter vs. low risk | 3.24 (0.72, 14.50) | 1.82 (0.33, 10.15) |
| Netherlands Patients | High vs. low risk | 5.75 (2.54, 13.02) | 9.93 (2.13, 46.18) |
| | Inter vs. low risk | 2.71 (0.85, 8.66) | 3.26 (0.46, 23.33) |

| Comparison | Hazard Ratio (95% C.I.) | Odds Ratio (95% C.I.) |
|---|---|---|
| High Risk vs. Low Risk | 23.18 (8.57, 62.73) | 25.44 (5.33, 121.41) |
| Inter Risk vs. Low Risk | 7.05 (2.24, 22.22) | 2.83 (0.82, 9.79) |

| Comparison | OR (95% C.I.) | P value |
|---|---|---|
| Inter Risk vs. Low Risk | 7.67 (2.24 - 28.14) | 0.001 |
| High Risk vs. Low Risk | 46.0 (14.86 - 169) | < 0.0001 |

| Patient Subset | Pathologic Diagnosis | Low Risk | Inter Risk | High Risk |
|---|---|---|---|---|
| Prevalent Cases | ND/IND | 3 | 4 | 8 |
| | LGD | 2 | 3 | 10 |
| Non-Progressors | ND/IND | 114 | 19 | 7 |
| | LGD | 1 | 2 | 2 |

FIG. 8D

METHODS OF PREDICTING PROGRESSION OF BARRETT'S ESOPHAGUS

CROSS-REFERENCE TO RELATED APPLICATIONS

This application is a U.S. national stage filing under 35 U.S.C. § 371 of International Application No. PCT/US2016/063482 entitled "METHODS OF PREDICTING PROGRESSION OF BARRETT'S ESOPHAGUS" and filed on Nov. 23, 2016, which claims benefit and priority under 35 U.S.C. § 119(e) to U.S. Provisional Application No. 62/260,010 entitled "METHODS OF PREDICTING PROGRESSION OF BARRETT'S ESOPHAGUS", filed Nov. 25, 2015. The contents of each of these applications are incorporated herein by reference in their entireties.

SUMMARY

Barrett's esophagus (BE) is a precursor to esophageal adenocarcinoma (EAC). Although the risk of progression of non-dysplastic BE (ND) to EAC is very low, treatment options for advanced EAC are limited and early detection is critical for optimal patient management. EAC can be prevented if dysplasia is detected and treated early with endoscopic therapies such as radiofrequency ablation (RFA) and/or endoscopic mucosal resection (EMR). Despite endoscopic surveillance programs aimed at preventing EAC in BE patients, the incidence of EAC continues to remain a health concern with 5 year survival rates at 17%. Accurate tests are needed to identify BE patients who are at high risk for progression and require therapeutic intervention as well as to recognize low risk BE patients who can potentially reduce the frequency of endoscopic surveillance. Such tests have been challenging to develop to date.

Current practice guidelines recommend endoscopic surveillance with biopsies at frequencies determined by the grade of dysplasia. However, histologic evaluation of esophageal biopsies can be limited by inter-observer variation and random endoscopic sampling. The histologic abnormalities in BE form a continuous spectrum and it can be difficult to distinguish grades of dysplasia. Furthermore, the molecular and cellular changes associated with malignant transformation can precede the morphologic changes that pathologists can evaluate by histology. Efforts have long been underway to identify risk prediction biomarkers in BE. This concept has become more important with the advent of highly effective endoscopic therapies such as RFA and EMR. Many biomarkers have been evaluated in BE but risk prediction biomarkers have been difficult to identify. The British Society of Gastroenterology (BSG) recommends use of p53 immunohistochemistry (IHC) to aid diagnosis of dysplasia, however, no single biomarker or panel of biomarkers for accurate risk prediction has been identified and validated to date. The complex structure of tissues highlights the need for an alternative systems biology approach to anatomic pathology. Assessment of tissues as a "system" has the potential to improve upon current tools by quantifying genetic, immunologic, vascular and morphologic features relevant to patient outcomes. These molecular and cellular features may more accurately stratify the genetic and non-genetic differences that place BE patients at risk of progression. This tissue systems pathology approach has been demonstrated to have potential diagnostic applications in BE. This approach may also have prognostic applications by objectively quantifying multiple molecular and cellular features that precede definitive morphologic changes. Herein, we describe a tissue systems pathology approach to risk stratification in BE. The approach employs multiplexed fluorescence biomarker labeling with digital imaging and image analysis to objectively quantify multiple epithelial and stromal biomarkers and morphology. The quantitative biomarker/morphometric data is integrated by a multivariable classifier into prognostic scores. The aim was to develop and independently validate a tissue systems pathology test that predicts future risk of progressing to high-grade dysplasia (HGD)/EAC in patients with BE.

In some embodiments, methods of determining a risk of progression of Barrett's esophagus in a subject are provided. In some embodiments, the method comprises determining image analysis features associated with biomarkers and morphology in a sample from the subject, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, wherein the combination of the image analysis features determines a score, and wherein the score correlates to the risk of progression of Barrett's esophagus in the subject.

In some embodiments, embodiments are disclosed that provide methods of determining a risk of progression of Barrett's esophagus in a subject. In some embodiments, the methods comprise: a) detecting biomarkers in a sample from the subject, wherein the biomarkers are p53, HIF-1α, COX2, p16, alpha-methylacyl-CoA racemase (AMACR), CD68, CD45RO, K20, and HER2/neu; and b) determining image analysis features associated with the biomarkers and morphology, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression of cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, wherein the combination of the image analysis features determines a score, and wherein the score correlates to the risk of progression of Barrett's esophagus in the subject.

In some embodiments, the subject has an increased risk of progression to low grade dysplasia, high grade dysplasia or esophageal cancer. In some embodiments, the subject has received a diagnosis of non-dysplastic intestinal metaplasia, reactive atypia, indefinite for dysplasia, low grade dysplasia, or high grade dysplasia.

In some embodiments, method of classifying Barrett's esophagus in a subject are provided. In some embodiments, the methods comprise determining image analysis features associated with biomarkers and morphology in a sample from a subject, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity; AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, wherein the combination of the image analysis features determines a score, and wherein the score correlates to the classification of Barrett's esophagus.

In some embodiments, method of classifying Barrett's esophagus in a subject are provided, the methods comprising: a) detecting biomarkers in a sample from the subject, wherein the biomarkers are p53, HIF-1α, COX-2, p16, alpha-methylacyl-CoA racemase (AMACR), CD68, CD45RO, K20, and HER2/neu; and b) determining image analysis features associated with the biomarkers and morphology, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity; AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, wherein the combination of the image analysis features determines a score, and wherein the score correlates to the classification of Barrett's esophagus.

In some embodiments, the classification of Barrett's esophagus comprises non-dysplastic intestinal metaplasia, reactive atypia, low grade dysplasia, and high grade dysplasia.

In some embodiments, methods of detecting a field effect associated with malignant transformation in an esophagus of a subject suffering from Barrett's esophagus are provided, the method comprising determining image analysis features associated with biomarkers and morphology in a sample from a subject, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity; AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, wherein the combination of the image analysis features determines a score, and wherein the score correlates to the probability of high grade dysplasia or esophageal cancer being present in the subject.

In some embodiments, methods of detecting a field effect associated with malignant transformation in an esophagus of a subject suffering from Barrett's esophagus are provide, the methods comprising: a) detecting biomarkers in a sample from the subject, wherein the biomarkers are p53, HIF-1α, COX-2, p16, alpha-methylacyl-CoA racemase (AMACR), CD68, CD45RO, K20, and HER2/neu; and b) determining image analysis features associated with the biomarkers and morphology, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity; AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, wherein the combination of the image analysis features determines a score, and wherein the score to the probability of high grade dysplasia or esophageal cancer being present in the subject.

In some embodiments, kits for determining a risk of progression of Barrett's esophagus in a subject are provided, the kits comprising: a) one or more probes capable of detecting biomarkers in a sample from the subject, wherein the biomarkers are p53, HIF-1α, COX2, p16, alpha-methylacyl-CoA racemase (AMACR), CD68, CD45RO, K20, and HER2/neu; and b) instructions for determining image analysis features associated with the biomarkers, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, to generate a score from a cell and/or tissue sample of a subject.

In some embodiments, kits for classifying Barrett's esophagus in a subject, the kits comprising: a) one or more probes that is capable of detecting nine biomarkers in a sample from the subject, wherein the biomarkers are p53, HIF-1α, COX2, p16, alpha-methylacyl-CoA racemase (AMACR), CD68, CD45RO, K20, and HER2/neu; and b) instructions for determining image analysis features associated with the biomarkers, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, to generate a score from a cell and/or tissue sample of a subject.

In some embodiments, methods of determining a risk of progression of Barrett's esophagus in a subject are provided, the methods comprising: a) obtaining at least one section from one or more tissue samples from the subject; b) labeling the at least one section with a panel of fluorescently-labeled reagents that include a reagent that labels nuclei in cells of the one or more tissue samples, thereby producing a fluorescently-labeled section; c) detecting biomarkers in a sample from the subject, wherein the biomarkers are p53, HIF-1α, COX2, p16, alpha-methylacyl-CoA racemase (AMACR), CD68, CD45RO, K20, and HER2/neu; d) analyzing said section using a digital image platform for multi-channel fluorescence whole slide imaging to produce high dimensional quantitative image analysis feature data on biomarkers; and e) determining image analysis features associated with the biomarkers, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, wherein the combination of the image analysis features determines a score, and wherein the score correlates to the risk of progression of Barrett's esophagus in the subject.

In some embodiments, methods of detecting a field effect associated with malignant transformation of Barrett's esophagus in a subject are provided, the methods comprising: a) obtaining at least one section from one or more tissue samples from the subject; b) labeling the at least one section with a panel of fluorescently-labeled reagents that include a reagent that labels nuclei in cells of the one or more tissue samples, thereby producing a fluorescently-labeled section; c) detecting biomarkers in a sample from the subject, wherein the biomarkers are p53, HIF-1α, COX2, p16, alpha-methylacyl-CoA racemase (AMACR), CD68, CD45RO, K20, and HER2/neu; d) analyzing said section using a digital image platform for multi-channel fluorescence whole slide imaging to produce high dimensional quantitative image analysis feature data on biomarkers; and e) determining image analysis features associated with the biomarkers, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, wherein the combination of the image analysis features determines a score, and wherein the score correlates to the probability of high grade dysplasia or esophageal cancer being present in the subject.

In some embodiments, detecting the biomarkers comprises using probes that specifically bind to each of the biomarkers.

In some embodiments, the sample comprises cells containing cell nuclei, and wherein the cell nuclei are labeled with a nuclear label selected from the group consisting of Hoechst 33258, Hoechst 33342, Hoechst 34580, 4',6'-diamidino-2-phenylindole (DAPI), cyanine nucleic acid stains, and Hematoxylin.

In some embodiments, the sample comprises a brushing, scraping, biopsy, or surgical resection of cells and/or tissue from the subject. In some embodiments, the sample of cells and/or tissue is collected via random endoscopic sampling, computer-assisted endoscopic sampling, image-guided endoscopic sampling or non-endoscopic sampling via brushing, abrasion or scraping. In some embodiments, the sample is at room temperature or frozen. In some embodiments, the sample is freshly obtained, formalin fixed, alcohol fixed, or paraffin embedded. In some embodiments, the sample is a plurality of samples taken from multiple discrete endoscopic levels. For example, different samples are taken from a subject at different levels and a score is prepared based upon the totality of the samples as opposed to just one sample.

In some embodiments, the probes are fluorescent and/or comprise a fluorescent tag, or are detected via secondary probe that are fluorescent and/or comprise a fluorescent tag, e.g., wherein each probe is labeled with a different fluorophore. In some embodiments, the labeled slides are imaged to produce fields of view and/or whole slide images that are analyzed to extract features associated with biomarkers and morphology.

In some embodiments, the detection of 2 or more, e.g., 3 or more, e.g., 4 or more, e.g., 5 or more, e.g., 8 or more, e.g., 9 or more, e.g., 12 or more biomarkers are determined simultaneously.

In some embodiments, the subject is a human.

In some embodiments, the score is used to determine the frequency of endoscopic surveillance in a subject with Barrett's esophagus. In some embodiments, the score is used to determine whether a patient is a candidate for therapeutic intervention to prevent progression of Barrett's esophagus.

In some embodiments, the therapeutic intervention is an endoscopic ablation, endoscopic photodynamic therapy, endoscopic cryotherapy, endoscopic mucosal resection, and/or surgical resection therapy, or a non-endoscopic surgical therapy or systemic therapy.

In some embodiments, the image analysis features determine a score, relative to a control.

BRIEF DESCRIPTION OF THE DRAWINGS

FIG. 2A-FIG. 2E. Development and Performance of 15-Feature Risk Score in Training Set of BE Patients. FIG. 2A: ROC curve for 15-feature risk score in training set of incident progressor and non-progressor patients. FIG. 2B, FIG. 2C and FIG. 2D: KM analysis of probability of progression to HGD/EAC in patients scored low-, intermediate- and high-risk by the 15-feature risk classifier from all four institutions, the three US institutions and AMC, respectively. FIG. 2E: Univariate HRs and ORs with 95% C.I. for comparisons between risk groups.

FIG. 3A: Endoscopy image from IP showing BE without visible lesions; FIG. 3B: H&E-stained biopsy from IP showing ND; FIG. 3C: Biomarker patterns in ND biopsy from IP (upper-left fragment: p53, p16, AMACR, Hoechst, upper-right: HER2/neu, K20, Hoechst, lower-left: CD68, COX-2, Hoechst, lower-right: HIF-1α, CD45RO, Hoechst; FIG. 3D: Endoscopy image from NP showing BE without visible lesions; FIG. 3E: H&E-stained biopsy from NP showing ND; FIG. 3F: Biomarker patterns in ND biopsy from NP showing absence of high-risk changes (upper-left: p53, p16, AMACR, Hoechst, upper-right: HER2/neu, K20, Hoechst, lower-left: CD68, COX-2, Hoechst, lower-right: HIF-1α, CD45RO, Hoechst.

FIG. 4A-FIG. 4F. Validation of 15-Feature Risk Classifier in Independent Validation Set of BE Patients. FIG. 4A: ROC curve for 15-feature risk classifier in validation set. FIG. 4B, FIG. 4C and FIG. 4D: KM analysis of probability of progression to HGD/EAC in validation set patients scored low-, intermediate- and high-risk by the 15-feature risk classifier in patients from all four institutions, US institutions and AMC, respectively. FIG. 4E: HRs and ORs (95% C.I.) for comparisons between risk groups. FIG. 4F: 5-year progression rate as a continuous function of the risk score.

FIG. 6A-FIG. 6C Performance of 3-Tier Risk Classifier in Stratifying BE Patients with Prevalent HGD/EAC from Non-Progressor BE Patients. FIG. 6A: ROC Curve for 3-tier risk classifier based on the binary outcome of low/high. FIG. 6B: KM analysis of probability of subsequent diagnosis of HGD/EAC in patients scored low-, intermediate- and high-risk by the risk classifier. FIG. 6C: Univariate HRs and ORs with 95% C.I for comparisons between risk groups predicted by the classifier.

FIG. 8A-FIG. 8E illustrates performance of 15-Feature Risk Score in Non-Dysplastic and LGD BE Biopsies from Non-Progressor Patients and Patients with Prevalent HGD/EAC. FIG. 8A: ROC curve for 15-feature risk score and percentage of cells overexpressing p53 (determined by image analysis software as described previously (Example 3, reference 19). FIG. 8B: Box and whisker plots of the 15-feature risk score in non-progressors and prevalent cases ($p<0.0001$, Wilcoxon rank sum test comparing non-progressors vs. all prevalent cases). FIG. 8C: Univariate ORs with 95% C.I. and p-values from logistic regression for comparisons between the predicted risk classes. FIG. 8D: Number of cases scored low-, intermediate (inter)-, and high-risk by GI subspecialist pathologic diagnosis. FIG. 8E: Rate of subsequent diagnosis of HGD/EAC as a continuous function of the 15-feature risk score. Dashed curves indicate 95% C.I. The rug plot on the x-axis shows the risk score for non-progressor controls (black dashes) and prevalent cases (red dashes), and cutoffs for low-, inter-, and high-risk are shown.

FIG. 9A-FIG. 9D show an ND biopsy from a patient who had HGD on repeat endoscopy 310 days later; FIG. 9A: p53, AMACR, Hoechst, FIG. 9B: HER2/neu, Hoechst. FIG. 9C: CD68, COX-2, Hoechst, FIG. 9D: HIF-1α, CD45RO, Hoechst. FIG. 9E: p53, AMACR, Hoechst; FIG. 9F: HER2/neu, Hoechst. FIG. 9G: CD68, COX-2, FIG. 9H: HIF-1α, CD45RO, Hoechst. FIG. 9I: p53, AMACR, Hoechst; FIG. 9J: HER2/neu, Hoechst. FIG. 9K: CD68, COX-2, Hoechst, FIG. 9L: HIF-1α, CD45RO, Hoechst. FIG. 9M-FIG. 9P show a ND biopsy from a non-progressor patient with HGD/EAC-free surveillance time of 2,186 days; FIG. 9M: p53, AMACR, Hoechst; FIG. 9N: HER2/neu, Hoechst. FIG. 9O: CD68, COX-2, Hoechst; FIG. 9P: HIF-1α, CD45RO, Hoechst.

FIG. 10A-FIG. 10E and FIG. 10F-FIG. 10J show a LGD biopsy and a ND biopsy, respectively, from a patient with 2 cm segment BE who had HGD on repeat endoscopy 56 days later. The images show similar epithelial and stromal abnormalities in the biopsies despite the difference in diagnosis. The 15-feature risk scores for the LGD and ND biopsies were 8.7 and 8.9 (both high-risk), respectively. FIG. 10A-FIG. 10E LGD biopsy -FIG. 10A: H&E, FIG. 10B: p53, AMACR, Hoechst; FIG. 10C: HER2/neu, Hoechst. FIG. 10D: CD68, COX-2, Hoechst; FIG. 10E: HIF-1α, CD45RO, Hoechst. FIG. 10F-FIG. 10J ND biopsy -FIG. 10F: H&E, FIG. 10G: p53, AMACR, Hoechst; FIG. 10H: HER2/neu, Hoechst. FIG. 10I: CD68, COX-2, Hoechst; FIG. 10J: HIF-1α, CD45RO, Hoechst.

DETAILED DESCRIPTION

Figure 1A:
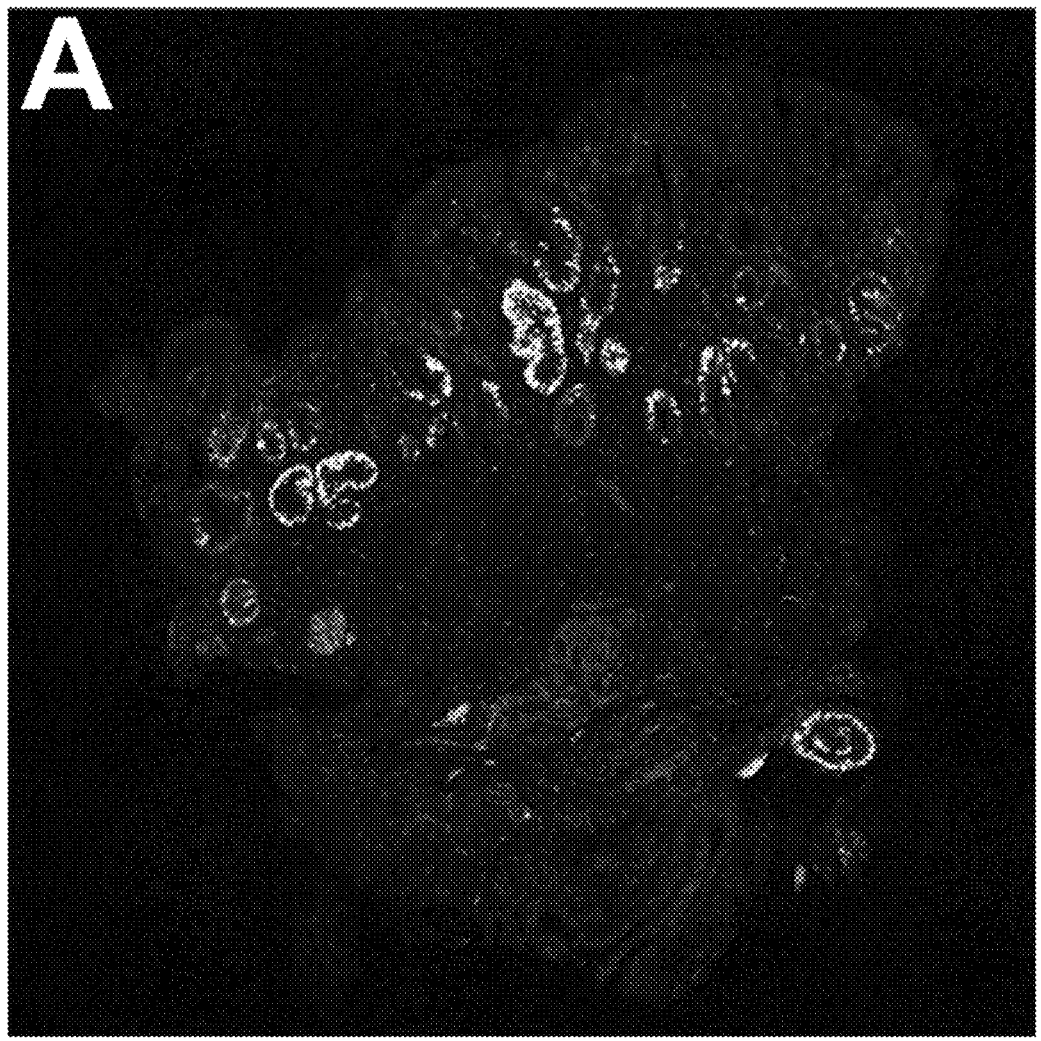
FIG. 1A-FIG. 1F. Multiplexed Biomarker Labeling and Imaging in Incident Progressor BE Cases. Representative images of the 9 biomarkers on which the 15-feature classifier is based from 2 ND biopsies (FIG. 1A-FIG. 1B and FIG. 1C-FIG. 1D) and 1 LGD biopsy (FIG. 1E-FIG. 1F) from incident progressors. A: p53, AMACR, p16, Hoechst; B: CD68, COX-2, Hoechst; C: p53, AMACR, p16, Hoechst; D: CD68, COX-2, Hoechst; E: HER2/neu, K20, Hoechst; F: HIF-1α, CD45RO, Hoechst.
Figure 1B:
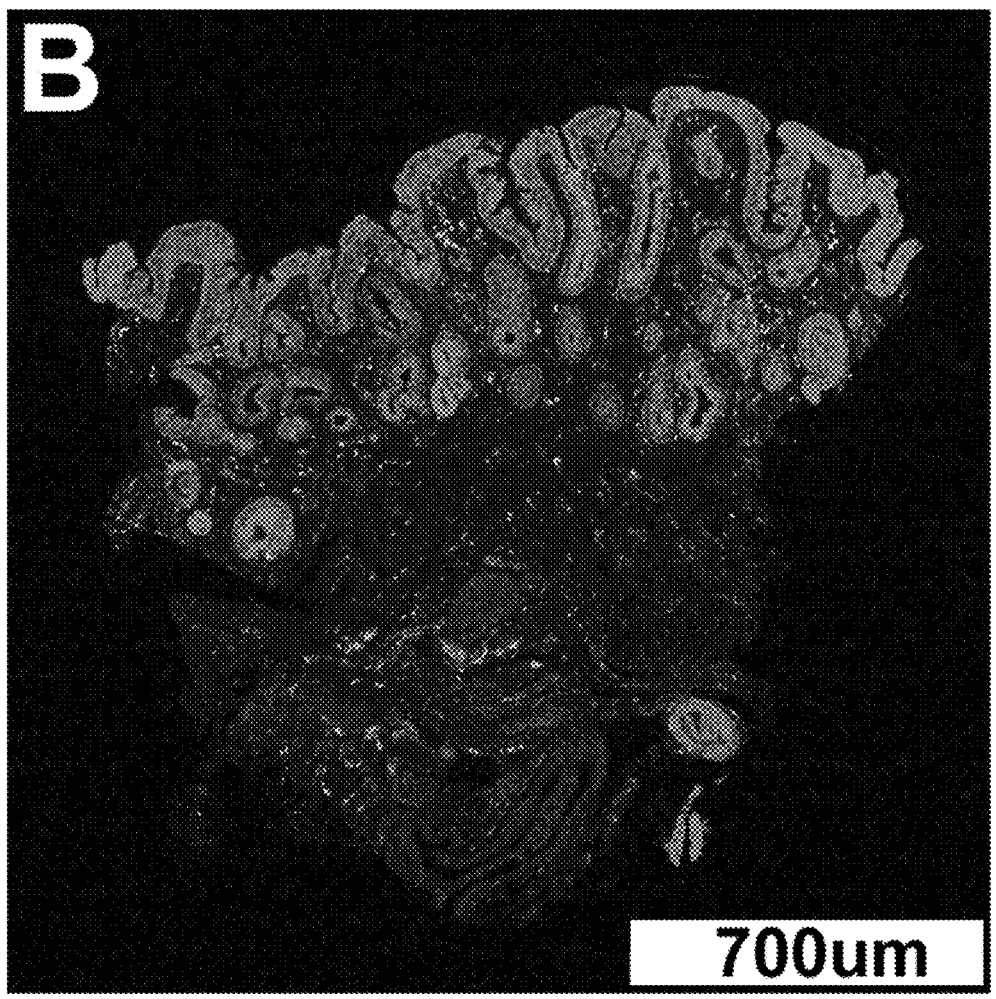
Figure 1C:
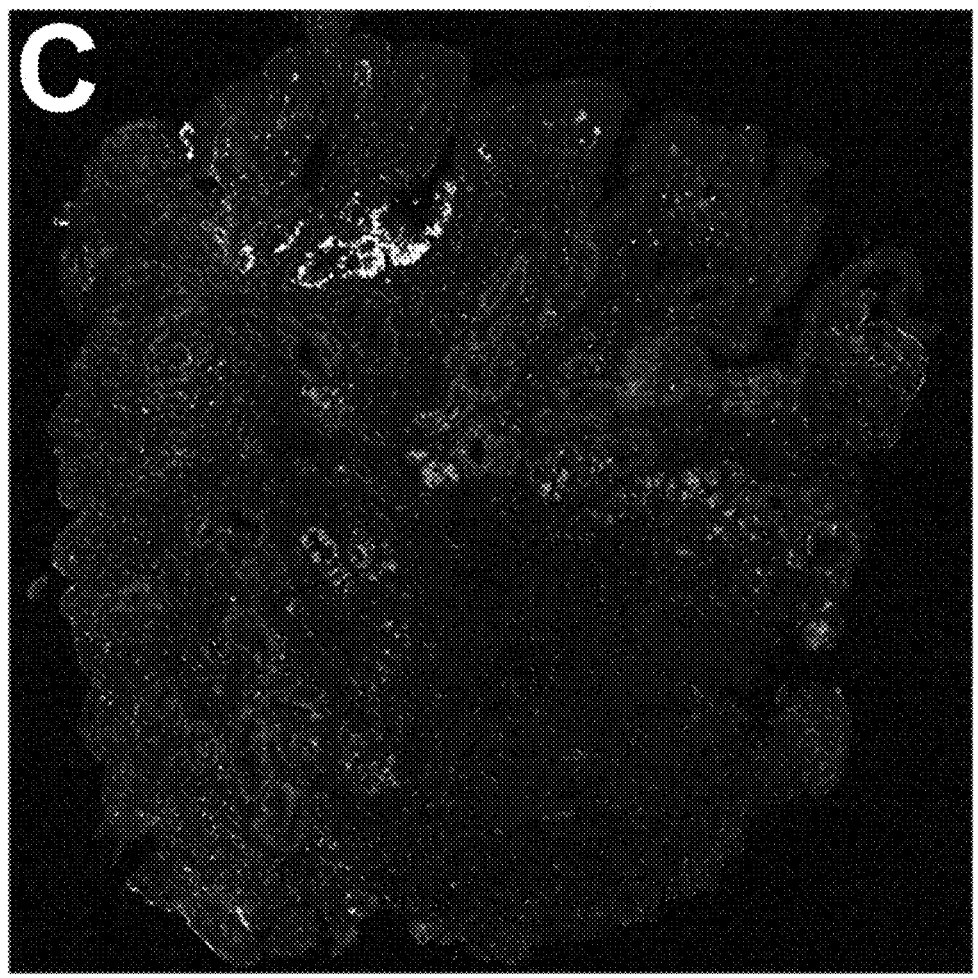
Figure 1D:
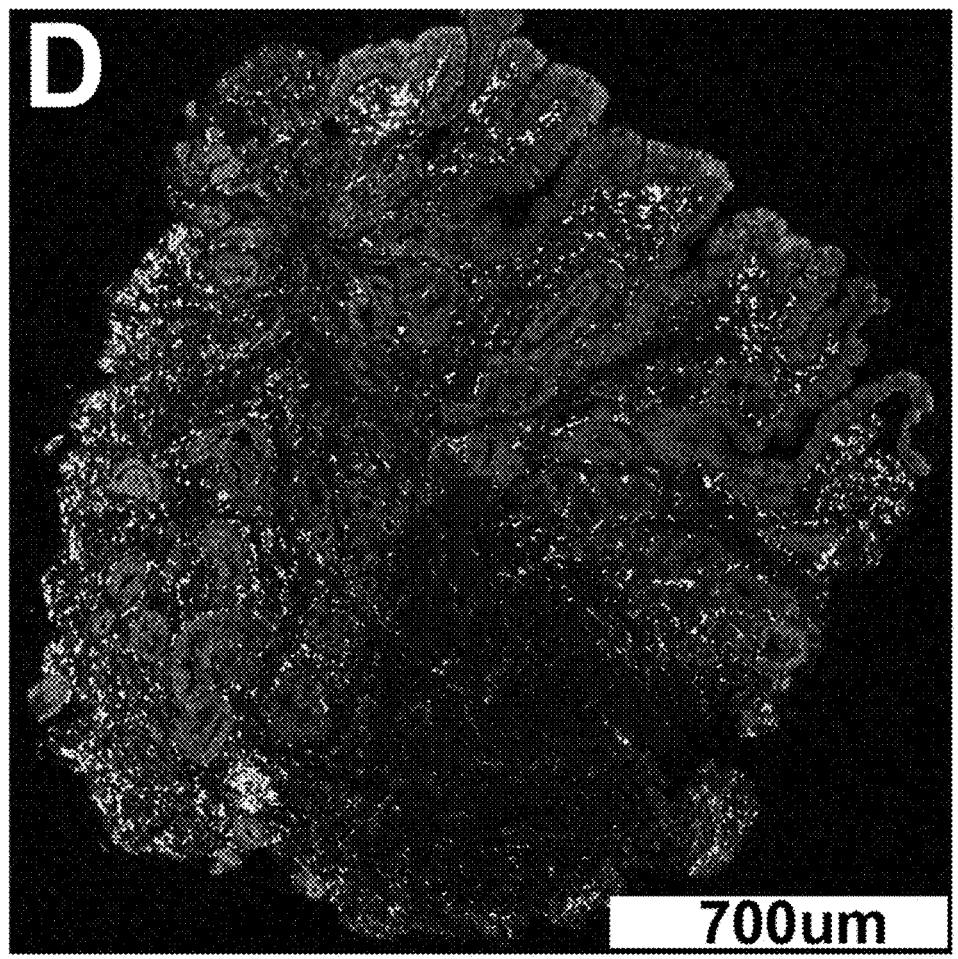
Figure 1E:
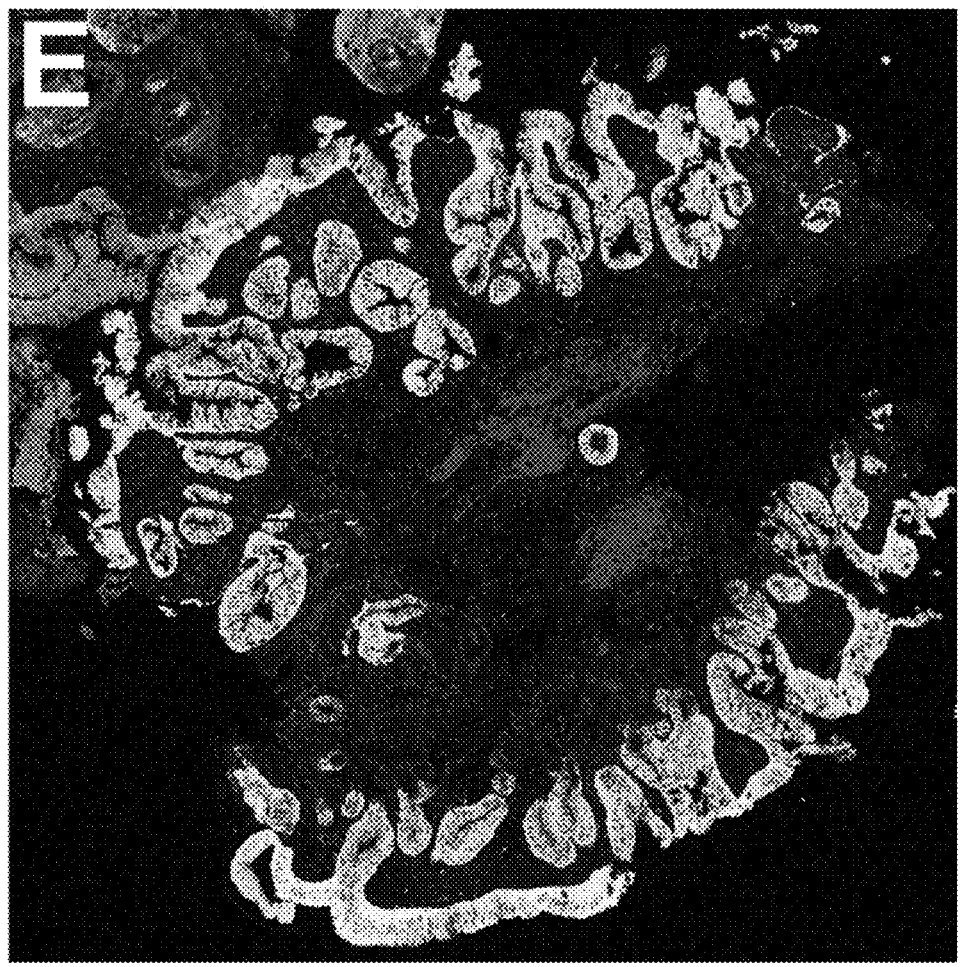
Figure 1F:
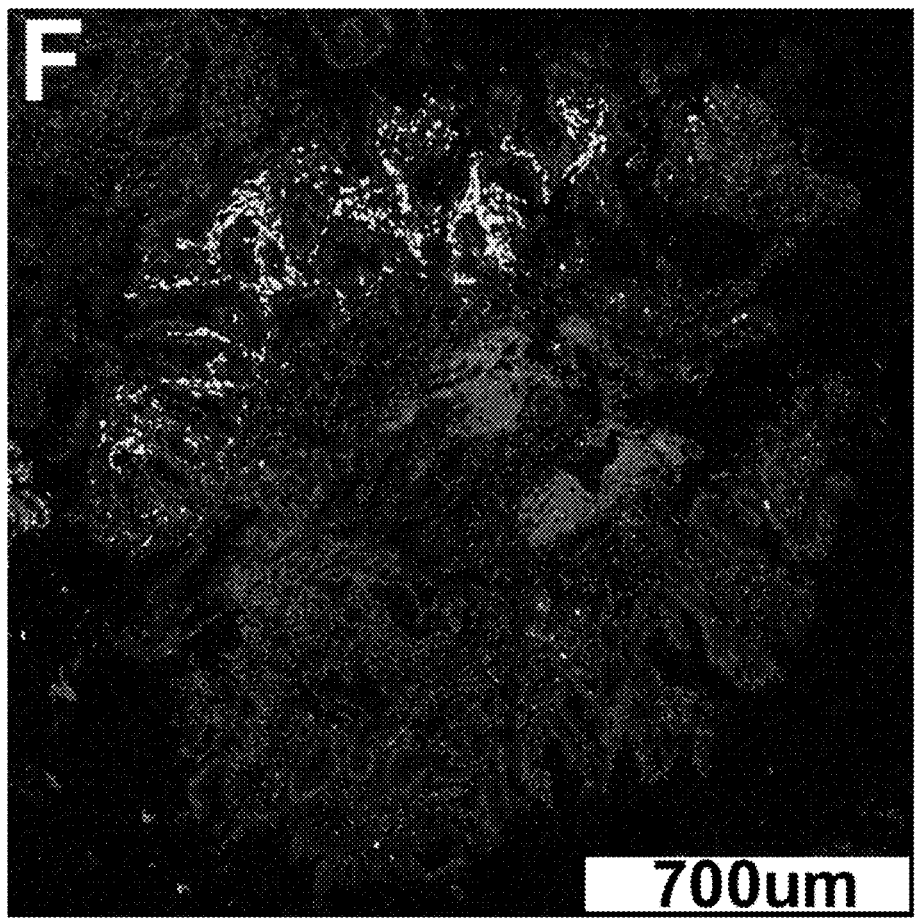

Before the present compositions and methods are described, it is to be understood that these embodiments are not limited to the particular processes, compositions, or methodologies described, as these may vary. It is also to be understood that the terminology used in the description is for the purpose of describing the particular versions or embodiments only, and is not intended to limit the scope unless explicitly stated. Unless defined otherwise, all technical and scientific terms used herein have the same meanings as commonly understood by one of ordinary skill in the art. All publications mentioned herein are incorporated by reference in their entirety.

It must also be noted that as used herein and in the appended claims, the singular forms "a", "an", and "the" include plural reference unless the context clearly dictates otherwise.

As used in this document, terms "comprise," "have," and "include" and their conjugates, as used herein, mean "including but not limited to." While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

Acronyms of Biomarkers used herein are defined in Table 1. Other acronyms not specifically defined herein have their meaning known to one of skill in the art.

TABLE 1

List of Biomarkers

| | |
|---|---|
| p53 | Cellular tumor antigen p53, tumor suppressor p53 |
| HIF-1α | Hypoxia-inducible factor-1 alpha |
| COX2 | Cyclooxygenase-2 |
| p16 | Cyclin-dependent kinase inhibitor 2A, multiple tumor suppressor 1 |
| AMACR | Alpha-methylacyl-CoA racemase |
| CD68 | Cluster of Differentiation 68 |
| CD45RO | Cluster of differentiation 45 antigen located in memory T cells |
| K20 | Keratin 20 |
| HER2/neu | Human epidermal growth factor receptor 2 |

As used herein, the term "biomarker" means any analyte, metabolite, nucleic acid, amino acid sequence or fragments thereof, polyprotein, protein complex, molecule, or chemical compound that is produced, metabolized, catabolized, secreted, phagocytosed, or expressed by a cell or tissue and that provides a useful measure of the presence, absence, or quantity of a certain cell type or descriptive feature indicative of, characteristic of, or suggestive of a diagnosis of a particular disease or disorder. In some embodiments, the biomarker is chosen from one or more of the molecules identified in Table 1. The biomarkers may be the measure of receptor expression levels, transcription factor activation; location or amount or activity of a protein, polynucleotide, organelle, and the like; the phosphorylation status of a protein, ratio of a protein between cellular compartments and tissue compartments, ratio of one protein to another protein, co-localization or co-expression of at least two proteins, etc. The biomarker may be a nucleic acid (e.g., DNA, RNA, including micro RNAs, snRNAs, mRNA, rRNA, etc.), a receptor, a cell membrane antigen, an intracellular antigen, and extracellular antigen, a signaling molecule, a protein, and the like without limitation, lipids, lipoproteins, proteins, cytokines, chemokines, growth factors, peptides, nucleic acids, genes, and oligonucleotides, together with their related complexes, metabolites, mutations, variants, polymorphisms, modifications, fragments, subunits, degradation products, elements, and other analytes or sample-derived measures. A biomarker may also include a mutated protein or proteins, a mutated nucleic acid or mutated nucleic acids, variations in copy numbers, and/or transcript variants, in circumstances in which such mutations, variations in copy number and/or transcript variants are useful for generating a predictive model, or are useful in predictive models developed using related markers (e.g., non-mutated versions of the proteins or nucleic acids, alternative transcripts, etc.).

As used herein, the disease is a gastrointestinal disorder. As used herein, the term "gastrointestinal disorder" refers to any disease or abnormality related to the alimentary canal including, but not necessarily limited to one or more of the following conditions: abdominal pain, gastroesophageal reflux disease (GERD), constipation, diarrhea, diverticulosis, gastrointestinal bleeding, stomach cancer, esophageal cancer, intestinal cancer, colon cancer, Barrett's esophagus, irritable bowel disease, infectious colitis, ulcerative colitis, Crohn's disease, ischemic colitis, radiation colitis, irritable bowel syndrome, acute perforation, ileus, appendicitis, intra-abdominal abscesses, intestinal obstruction, gastritis, autoimmune metaplastic atrophic gastritis, ulcers in the stomach, peptic ulcer disease, dyspepsia, gastrointestinal stromal tumors, small bowel tumors, levator syndrome, pilonidal disease, proctits, fistulkas, fissures, incontinence.

The term "subclass of Barrett's esophagus" refers to any presentation of Barrett's esophagus classified as having any common combination of one or more descriptive features. A subclass of Barrett's esophagus may refer to one of the following conditions: Barrett's esophagus, no dysplasia, no progression in 5 years; Barrett's esophagus, no dysplasia, progression to low/high grade dysplasia in 5 years; Barrett's esophagus, indefinite for dysplasia, no progression in 5 years; Barrett's esophagus, indefinite for dysplasia, progression to low/high grade dysplasia or adenocarcinoma in 5 years; Barrett's esophagus, reactive atypia; Barrett's esophagus, low grade dysplasia, no progression in 5 years; Barrett's esophagus, low grade dysplasia, progression to high grade dysplasia or adenocarcinoma in 5 years; Barrett's esophagus, high grade dysplasia; Esophageal adenocarcinoma arising in a background of Barrett's esophagus. The subclass of Barrett's esophagus may refer to one of the following conditions: low-grade dysplasia, high-grade dysplasia, reactive atypia, indefinite for dysplasia, or indeterminate Barrett's esophagus. The subclass of Barrett's esophagus may refer to any one of the following conditions: gastric fundic-type columnar epithelium, cardia-type columnar epithelium, or intestinal-type columnar epithelium with or without goblet cells present above the gastroesophageal junction.

As used herein, the terms "cell sample," "tissue sample," or "sample" mean a composition comprising an isolated cell or plurality of cells. The sample may comprise an individual cell, a composition comprising a plurality of cells, a tissue sample taken from a subject with a gastrointestinal disorder, a tissue sample, a plurality of cells from the gastrointestinal tract, or a plurality of esophageal cells. The sample may be freshly obtained, formalin fixed, alcohol-fixed and/or paraffin embedded. The cell sample may be a biopsy isolated from a subject who has been diagnosed with, is suspected of having, or identified as having one or more gastrointestinal disorders, gastric fundic-type columnar epithelium, cardia-type columnar epithelium, or intestinal-type columnar epithelium with or without goblet cells present above the gastroesophageal junction or Barrett's esophagus. The sample may comprise a tissue from a brushing, scraping, punch biopsy, pinch biopsy, or surgical resection of a subject. The sample may be isolated from a human patient at one or more time points, such that at least one tissue sample is isolated from each time point from the same patient. The sample may be isolated from multiple spatial locations from the same patient at the same time point, including different endoscopic levels. The sample may be isolated by random sampling of areas affected by gastrointestinal disorders or Barrett's esophagus or by image-guided techniques. The sample may include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art. The sample can be obtained by the subject or by a third party, e.g., a medical professional. Examples of medical professionals include physicians, emergency medical technicians, nurses, first responders, psychologists, medical physics personnel, nurse practitioners, surgeons, dentists, and any other obvious medical professional as would be known to one skilled in the art. A sample can include peripheral blood cells, isolated leukocytes, or RNA extracted from peripheral blood cells or isolated leukocytes. In some embodiments, the sample is a plurality of samples taken at multiple discrete endoscopic levels. For example, different samples are taken from a subject at different endoscopic levels and a score is prepared based upon the totality of the samples as opposed to just one sample.

As used herein, the term "image analysis features" refers to the quantitative measurements of biomarkers and morphology within image objects, including: pixel intensity features of biomarkers (mean, sum, standard deviation, moment); percentages of objects exhibiting altered expression (overexpression, reduced expression or loss of expression of biomarkers); pixel intensity ratio features (ratio of one biomarker between different subcellular compartments, ratio of one biomarker to another in the same or a different subcellular compartment); coexpression or colocalization of two or more biomarkers within the same cell or within the same subcellular compartment; texture of biomarker signals as assessed by co-occurrence matrices; morphometrics including object area, equivalent diameter, solidity, eccentricity. Features can be localized to segmented cell-based objects, tissue structural objects, specific cell types including epithelial cells, endothelial cells, and stromal cells, specific populations defined by expression levels of 1, 2 or 3 biomarkers, and to image microenvironments or image regions. The quantitative measure can then be transformed using the equations described herein using the coefficients that are described herein, for example in Table 2. One of skill in the art would understand how to transform the measurements into the raw score based upon the disclosure herein and the knowledge of the skilled artisan.

As used herein, the term "control" means healthy esophageal tissue, Barrett's esophagus tissue with no dysplasia, Barrett's esophagus tissue from a subject that did not progress to low grade or high grade dysplasia, or esophageal carcinoma.

As used herein, the term "converting" means subjecting the features to an interpretation function or algorithm for a predictive model of disease. The interpretation function can also be produced by a plurality of predictive models, such as a regression model, a Bayesian classifier or score. The interpretation function may comprise one or more terms associated with one or more biomarker or sets of biomarkers, one or more terms associated with the presence or absence or spatial distribution of the specific cell types disclosed herein. The interpretation function comprises one or more terms associated with the presence, absence, quantity, intensity, or spatial distribution of the morphological features of a cell in a sample.

As used herein, the term "location" refers to a subcellular compartment, whole cell, or tissue compartment. Subcellular compartments include the nucleus, cytoplasm, plasma membrane, and nuclear membrane. Tissue compartments include the surface epithelium, glands, lamina propria, stroma, muscularis mucosa, and tumor.

As used herein, the term "probe" refers to any molecule that binds or intercalates to a biomarker, either covalently or non-covalently, i.e. antibodies, DNA or RNA molecules. The probes may include probe sets which include one or more probes that bind a single biomarker. The term "probe set" is sometime interchangeable for a panel of two or more probes that allow the detection of one or more biomarkers. The probe or probes may be fluorescently labeled. The fluorescently labeled probe may be specific for at least one biomarker. The panel of fluorescently labeled probes may detect at least about two different biomarkers. Each fluorescently labeled probe may have different fluorescent properties, which are sufficient to distinguish the different fluorescently labeled probes in the panel.

The terms "reagents" or "panel of reagents" refers to any substance or mixture for use in chemical analysis or other reaction known to those skilled in the art; i.e. stains, solvents, catalysts, enzymes, standards, organic or inorganic molecules.

The term "optical scanner" is used throughout the specification to describe any device or series of devices that generates image data from a cell sample or set of cell samples, or tissue samples. Optical scanner is used to describe any optical device or series of devices that generates digital image data from a sample or set of samples. The optical scanner may be a microscope attached to an optical device that generates digital image data, which, when sent to image forming apparatus such as a laser printer, a barcode reader, a confocal scanning laser microscope, or an imaging display (monitor), can produce an image visible to a user.

As used herein, the term "ratio" means the ratio of one biomarker's quantity to a different biomarker's quantity in the same or different subcellular compartment or tissue compartment. It can also mean the ratio of one biomarker's quantity in a subcellular compartment to quantity of same biomarker in another subcellular compartment within the same cell. It can also mean the ratio of one biomarker's quantity in a tissue compartment to quantity of same biomarker in another tissue compartment within the same biopsy.

As used herein, the term "p53 nuclear sum intensity" is the sum or total p53 signal within segmented nuclei within a digital image of a tissue labeled with reagents including an anti-p53 antibody and a nuclear label.

As used herein, the term "p53 nuclear mean intensity" is the mean of p53 signal intensity within segmented nuclei within a digital image of a tissue labeled with reagents including an anti-p53 antibody and a nuclear label.

As used herein, the term "ratio of mean HER2/neu intensity:mean K20 intensity in nuclei clusters" refers to the ratio of the mean HER2/neu signal intensity to mean cytokeratin-20 intensity within segmented nuclei clusters within a digital image of a tissue labeled with reagents including an anti-HER2 antibody, an anti-cytokeratin-20 antibody and a nuclear label.

As used herein, the term "ratio of 95th quantile HER2/neu intensity:95th quantile K20 intensity in nuclei clusters" refers to the ratio of 95th percentile of HER2/neu signal intensity to 95th percentile of cytokeratin-20 signal intensity within segmented nuclei clusters within a digital image of a tissue labeled with reagents including an anti-HER2 antibody, an anti-cytokeratin-20 antibody and a nuclear label.

As used herein, the term "coexpression cellular COX2 and CD68" refers to the colocalized COX2 signal and CD68 signal within segmented cell objects within a digital image of a tissue labeled with reagents including an anti-COX2 antibody, an anti-CD68 antibody and a nuclear label.

As used herein, the term "p53 mean intensity in nuclei clusters" is the mean of p53 signal intensity within segmented nuclei clusters within a digital image of a tissue labeled with reagents including an anti-p53 antibody and nuclear label.

As used herein, the term "nuclear solidity in p53-overexpressing p16-negative cells" refers to the solidity of segmented nuclei object borders in cells exhibiting overexpression of p53 (above threshold for positivity) and concomitant reduced expression or loss of expression of p16 (below threshold for p16-positivity) with a digital image of a tissue labeled with reagents including an anti-p53 antibody, an anti-p16 antibody and a nuclear label. For example, solidity of segmented nuclei object borders is calculated in a population of segmented cell-based objects passing through two Boolean filters: nuclei p53 mean intensity greater than 95 and cell p16 mean intensity less than 100, on a scale of 0-1023 in 10-bit tissue images, or equivalent scale in lower or higher bit tissue images.

As used herein, the term "CD45RO plasma membrane sum intensity" is the sum or total CD45RO signal within segmented plasma membrane objects within a digital image of a tissue labeled with reagents including an anti-CD45RO antibody and a nuclear label.

As used herein, the term "AMACR microenvironment standard deviation" is the standard deviation of AMACR signal intensity in segmented cell-based objects localized to microenvironment rectangles of 161×161 pixels within a digital image of tissue labeled with reagents including an anti-AMACR antibody and a nuclear label.

As used herein, the term "COX2 texture in cytoplasm" refers to the contrast textural feature extracted from a co-occurrence matrix (described by Haralick R M, Shanmugam K, Dinstein I. Textural Features for Image Classification. IEEE Trans Syst Man Cybern B Cybern 1973; SMC-3: 610-21) and a measure of the COX2 intensity contrast between a pixel and its neighbor in segmented cytoplasm objects in a whole digital image of a tissue labeled with reagents including an anti-COX2 antibody and a nuclear label.

As used herein, the term "HIF-1α microenvironment cell mean intensity" is the mean of HIF1alpha signal intensity in segmented cell-based objects localized to microenvironment rectangles of 161×161 pixels within a digital image of tissue labeled with reagents including an anti-HIF1alpha antibody and a nuclear label.

As used herein, the term "HIF-1α microenvironment cell moment (product of mean and standard deviation)" is the mean of HIF1alpha signal intensity multiplied by the standard deviation of HIF1alpha signal intensity in segmented cell-based objects localized to microenvironment rectangles of 161×161 pixels within a digital image of tissue labeled with reagents including an anti-HIF1alpha antibody and a nuclear label.

As used herein, the term "p16 cytoplasm mean intensity" is the mean of p16 signal intensity within segmented cytoplasm compartments within a digital image of a tissue labeled with reagents including an anti-p16 antibody and a nuclear label.

As used herein, the term "nuclear area in p53-overexpressing p16-negative cells" refers to the area of, or number of pixels within, segmented nuclei objects in cells exhibiting overexpression of p53 (above threshold for positivity) and concomitant reduced expression or loss of expression of p16 (below threshold for p16-positivity) with a digital image of a tissue labeled with reagents including an anti-p53 antibody, an anti-p16 antibody and a nuclear label. For example, area of segmented nuclei objects is calculated in a population of segmented cell-based objects passing through two Boolean filters: nuclei p53 mean intensity greater than 95 and cell p16 mean intensity less than 100, on a scale of 0-1023 in 10-bit images of samples, or equivalent scale in lower or higher bit images.

As used herein, the term "Hoechst nuclear 95th quantile intensity" is the 95th percentile of Hoechst signal intensity within segmented nuclei objects within a digital image of a tissue labeled reagents including a nuclear label.

As used herein, the term "nuclear label" refers to the fluorescent or histological chemical that binds to or stains components of nuclei such as DNA, which when imaged can be utilized to segment nuclei as individual objects with digital images.

As used herein, the term "nuclei clusters" refers to the image analysis mask that segments clusters of nuclei within a digital image of a tissue labeled with reagents including a nuclear label. For example, a nuclei cluster mask is based on Gaussian smoothing in the Hoechst channel of a digital image of a tissue labeled with reagents including Hoechst, followed by rank order filter, image threshold using Otsu's method, morphological operations to remove small objects (image open (erosion followed by a dilation using the same structuring element), close (dilation followed by an erosion using the same structuring element) and dilate using a flat, disk-shaped structuring element)) and finally connected components labeling.

As used herein, the term "nuclear solidity" is a measure of nuclear membrane contour regularity, and can be calculated as the ratio of the area of the nuclear object and of the convex hull of the nuclear object.

As used herein, the term "score" refers to the numerical value generated from the analysis of a sample from a subject using the 15-feature risk prediction model. Score may refer to a single value that can be used as a component in a predictive model for the diagnosis, prognosis, or clinical treatment plan for a subject, wherein the single value is calculated by combining the values of descriptive features through an interpretation function or algorithm.

The "15-feature risk prediction model" is defined as the scaling of the 15 features using defined center and scale parameters, then weighted by coefficients derived from univariate Cox regression analysis of the features and progression outcomes that was performed in a nested case-control training study (see Table 2). The coefficient-weighted (see, for example, Table 2) sum of the 15 scaled features produces an unscaled risk score, which is scaled as follows:

$$\text{Risk Score} = \begin{cases} 0 & \text{if raw score} < -10 \\ \dfrac{\text{raw score} + 10}{2} & \text{if } -10 < \text{raw score} < 10 \\ 10 & \text{if raw score} > 10 \end{cases}$$

Cutoffs are applied to the risk score to classify patients for risk of progression. For example, in some embodiments, risk class is considered low if scaled score falls between 0 and less than 5.5, intermediate if scaled score is greater than or equal to 5.5 and less than 6.4, and high if scaled score is between greater than or equal to 6.4 and 10. The scaled scores can also be assigned to a different scale and the different cutoffs can be scaled according to the different scale.

TABLE 2

15 Features Utilized by Risk Classifier

| Biomarker | Image Analysis Feature | Measure | Center | Scale | Coefficient |
|---|---|---|---|---|---|
| p53 | p53 nuclear sum intensity | $75^{th}$ percentile | 0.219043 | 0.102888 | −8.04439 |
| p53 | p53 nuclear mean intensity | $15^{th}$ percentile | −0.72326 | 0.136933 | 6.358257 |
| HER2/neu and K20 | Ratio of mean HER2/neu intensity:mean K20 intensity in nuclei clusters | $25^{th}$ percentile | −0.60261 | 0.202539 | 4.547325 |
| HER2/neu and K20 | Ratio of 95th quantile HER2/neu intensity:95th quantile K20 intensity in nuclei clusters | $25^{th}$ percentile | −0.61577 | 0.200684 | 4.286031 |
| COX2 and CD68 | Coexpression cellular COX2 mean intensity and cellular CD68 mean intensity | $85^{th}$ percentile | 76.6323 | 48.9231 | −0.02203 |
| p53 | p53 mean intensity in nuclei clusters | $5^{th}$ percentile | −1.03016 | 0.225405 | 3.099642 |
| p53, p16 and nuclear morphology (solidity) | Nuclear solidity in p53+ p16− cells | IQR | 0.130652 | 0.051562 | 15.62477 |
| CD45RO | CD45RO plasma membrane sum intensity | $75^{th}$ percentile | −0.02231 | 0.186223 | −3.76449 |
| AMACR | AMACR microenvironment standard deviation | Mean standard deviation in top 5 or less microenvironments | 1889.148 | 961.4859 | 0.000789 |
| COX2 | COX2 texture in cytoplasm | $75^{th}$ percentile | 0.031565 | 0.081008 | 10.39816 |
| HIF1alpha | HIF-1alpha microenvironment cell mean intensity | Mean HIF-1alpha intensity in the top 5 percent of microenvironments (filtered based on mean HIF-1alpha intensity) multiplied by the number of objects in the filtered microenvironments | 3385.765 | 1743.198 | 0.000349 |
| HIF1alpha | HIF-1alpha microenvironment cell moment (product of mean and standard deviation) | $95^{th}$ percentile of HIF-1alpha intensity moment in the top 5 percent of microenvironments (filtered based on mean HIF-1alpha intensity moment) multiplied by the number of objects in the filtered microenvironments | 603055.9 | 585971.8 | 1.02E−06 |
| p16 | p16 cytoplasm mean intensity | $15^{th}$ percentile | −0.79388 | 0.127974 | −4.98699 |
| p53, p16 and nuclear morphology (area) | Nuclear area in p53+ p16− cells | IQR | 116.8669 | 44.74047 | 0.014368 |
| Nuclear morphology | Hoechst nuclear 95th quantile intensity | $25^{th}$ percentile | −0.69377 | 0.039071 | 10.78732 |

As used herein, the term "determining risk of progression of Barrett's esophagus" means the probability of progressing to low grade dysplasia, high grade dysplasia, or esophageal adenocarcinoma/cancer.

As used herein, the term "classifying Barrett's esophagus" means assigning a diagnostic subcategory of Barrett's esophagus to a subject, including, no dysplasia, reactive atypia, indefinite for dysplasia, low grade dysplasia, high grade dysplasia, or esophageal adenocarcinoma/cancer.

As used herein, the term "detecting a field effect associated with malignant transformation in an esophagus" means acquiring features and calculating a score that are correlated with presence of molecular and cellular changes in the preneoplastic field surrounding dysplastic and/or cancerous lesions in an esophagus. The areas surrounding dysplastic and/or cancerous lesions may appear histologically non-dysplastic or only low grade dysplasia, but may exhibit molecular and cellular changes or abnormalities associated with malignant transformation to high grade dysplasia and/or cancer. These changes/abnormalities can occur within epithelial and stromal cells and can be quantified by features and converted into a score. Detection of molecular and cellular abnormalities in this expanded field may overcome the limitations of random sampling and subjective diagnoses, enabling earlier diagnosis and treatment of HGD and EAC.

As used herein, the term "instructions" refers to materials and methods for labeling and staining tissue slides with probes and reagents, imaging the probes on the tissue samples, analyzing the images to extract the biomarker data, and processing the data into a score.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 50% means in the range of 45%-55%.

Generally speaking, the term "tissue" refers to any aggregation of similarly specialized cells which are united in the performance of a particular function.

The term "antibody" refers to an immunoglobulin molecule or fragment thereof having a specific structure that interacts or binds specifically with a molecule comprising an antigen. As used herein, the term "antibody" broadly includes full-length antibodies and may include certain antibody fragments thereof. Also included are monoclonal and polyclonal antibodies, multivalent and monovalent antibodies, multispecific antibodies (for example bi-specific antibodies), chimeric antibodies, human antibodies, humanized antibodies and antibodies that have been affinity matured. An antibody binds selectively or specifically to a biomarker of a gastrointestinal disorder if the antibody binds preferentially to an antigen expressed by a cell and has less than 25%, or less than 10%, or less than 1% or less than 0.1% cross-reactivity with a polypeptide expressed by a cell within the gastrointestinal tissue or cells derived from another tissue that migrates from one tissue to the gastrointestinal tissue. Usually, the antibody will have a binding affinity (dissociation constant (Kd) value), for the antigen or epitope of about $10^{-6}$M, $10^{-7}$M, $10^{-8}$M, $10^{-9}$M, $10^{-10}$M, $10^{-11}$M, or $10^{-12}$M. Binding affinity may be assessed using any method known by one of ordinary skill in the art, such as surface plasma resonance, immunoaffinity assays, or ELISAs.

The term "subject" is used throughout the specification to describe an animal from which a sample is taken. The animal may be human. For diagnosis of those conditions which are specific for a specific subject, such as a human being, the term "patient" may be interchangeably used. In some instances in the description, the term "patient" will refer to human patients suffering from a particular disease or disorder. The subject may be a human suspected of having or being identified as at risk to develop a gastrointestinal disorder or Barrett's esophagus. The subject may be a non-human animal from which a sample is isolated or provided. The term "mammal" encompasses both humans and non-humans and includes but is not limited to humans, non-human primates, canines, felines, murines, bovines, equines, and porcines.

The terms "treating" and "to treat," mean to alleviate symptoms, eliminate the causation either on a temporary or permanent basis, or to prevent or slow the appearance of symptoms. The term "treatment" includes alleviation, elimination of causation (temporary or permanent) of, or prevention of symptoms and disorders associated with any condition. The treatment may be a pre-treatment as well as a treatment at the onset of symptoms.

In some embodiments, the kits and methods disclosed herein can be utilized with or on a subject in need of such treatment, which can also be referred to as "in need thereof." As used herein, the phrase "in need thereof" means that the subject has been identified as having a need for the particular method or treatment and that the treatment has been given to the subject for that particular purpose.

In some embodiments, the method of determining a risk of progression of Barrett's esophagus in a subject, comprises: a) obtaining an upper gastrointestinal sample from the subject; b) labeling cell nuclei in the sample with a panel of reagents; c) labeling a plurality of biomarkers in the sample, wherein the plurality of biomarkers are p53, HIF-1α, COX2, p16, alpha-methylacyl-CoA racemase (AMACR), CD68, CD45RO, K20, and HER2/neu; d) detecting the labeled plurality of biomarkers and cell nuclei with an optical scanner; e) generating digital image data from the detected labeled plurality of biomarkers and cell nuclei; f) analyzing the labeled sample using a digital image platform for multi-channel fluorescence whole slide imaging to produce high dimensional quantitative image analysis features; g) analyzing the image analysis features associated with the plurality of biomarkers and cell nuclei, wherein the image analysis features are p53 nuclear sum intensity, p53 nuclear mean intensity, ratio of mean HER2/neu intensity: mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity; h) determining a score using the combination of the image analysis features; and i) correlating the score to the risk of progression of Barrett's esophagus in the subject.

In some embodiments, the subject has an increased risk of progression to non-dysplastic intestinal metaplasia, reactive atypia, indefinite for dysplasia, low grade dysplasia, high grade dysplasia, or esophageal cancer.

In some embodiments, the subject that is identified as an increased risk of progression to non-dysplastic intestinal metaplasia, reactive atypia, indefinite for dysplasia, low grade dysplasia, high grade dysplasia, or esophageal cancer is treated with a therapeutic intervention. In some embodiments, the treatment is an endoscopic ablation therapy, endoscopic photodynamic therapy, endoscopic cryotherapy, endoscopic mucosal resection, a surgical resection therapy, a non-endoscopic surgical therapy, or systemic therapy.

In some embodiments, the subject has received a diagnosis of non-dysplastic intestinal metaplasia, reactive atypia, indefinite for dysplasia, low grade dysplasia, high grade dysplasia, or esophageal cancer. In some embodiments, the method further comprises treating the subject has received the diagnosis. In some embodiments, the treatment is an endoscopic ablation therapy, endoscopic photodynamic therapy, endoscopic cryotherapy, endoscopic mucosal resection, a surgical resection therapy, a non-endoscopic surgical therapy, or systemic therapy.

In some embodiments, the plurality of biomarkers may be detected using probes that specifically bind to each of the biomarkers. The probes may be fluorescent, contain a fluorescent tag, or may be detected via a secondary fluorescent probe or a secondary fluorescently tagged probe. Further, each probe may be labeled with a different fluorophore.

In some embodiments, the labeled plurality of biomarkers and cell nuclei may be imaged to produce fields of view that are analyzed to extract features associated with the biomarkers and morphology.

In some embodiments, the detection of the plurality of biomarkers may be determined simultaneously.

In some embodiments, the cell nuclei may be labeled with a panel of reagents selected from the group consisting of Hoechst 33258, Hoechst 33342, Hoechst 34580, 4',6'-diamidino-2-phenylindole (DAPI), cyanine nucleic acid stains, and hematoxylin.

In some embodiments, the score is used to determine the frequency of endoscopic surveillance in a subject with Barrett's esophagus or whether a patient is a candidate for therapeutic intervention to prevent progression of Barrett's esophagus. The therapeutic intervention may be an endoscopic ablation therapy, endoscopic photodynamic therapy, endoscopic cryotherapy, endoscopic mucosal resection, a surgical resection therapy, a non-endoscopic surgical therapy, or systemic therapy.

In some embodiments, the sample comprises a brushing, scraping, biopsy, or surgical resection of cells from the subject. The sample may be collected via random endoscopic sampling, computer-assisted endoscopic sampling, image-guided endoscopic sampling, or non-endoscopic sampling via brushing, abrasion or scraping.

In some embodiments, the sample may be at room temperature or frozen. The sample may be freshly obtained, formalin fixed, alcohol fixed, or paraffin embedded.

In certain embodiments, the method of classifying Barrett's esophagus in a subject, comprises: a) obtaining an upper gastrointestinal sample from the subject; b) labeling cell nuclei in the sample with a panel of reagents; c) labeling a plurality of biomarkers in the sample, wherein the plurality of biomarkers are p53, HIF-1α, COX2, p16, alpha-methylacyl-CoA racemase (AMACR), CD68, CD45RO, K20, and HER2/neu; d) detecting the labeled plurality of biomarkers and cell nuclei with an optical scanner; e) generating digital image data from the detected labeled plurality of biomarkers and cell nuclei; f) analyzing the labeled sample using a digital image platform for multi-channel fluorescence whole slide imaging to produce high dimensional quantitative image analysis features; g) analyzing the image analysis features associated with the plurality of biomarkers and cell nuclei, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity; h) determining a score using the combination of the image analysis features; and i) correlating the score to a classification of Barrett's.

In some embodiments, the classification of Barrett's esophagus comprises non-dysplastic intestinal metaplasia, reactive atypia, indefinite for dysplasia, low grade dysplasia, high grade dysplasia, or esophageal cancer.

In some embodiments, the subject has received a diagnosis of non-dysplastic intestinal metaplasia, reactive atypia, indefinite for dysplasia, low grade dysplasia, high grade dysplasia, or esophageal cancer.

In some embodiments, the plurality of biomarkers may be detected using probes that specifically bind to each of the biomarkers. The probes may be fluorescent, contain a fluorescent tag, or may be detected via a secondary fluorescent probe or a secondary fluorescently tagged probe. Further, each probe may be labeled with a different fluorophore.

In some embodiments, the labeled plurality of biomarkers and cell nuclei may be imaged to produce fields of view that are analyzed to extract features associated with the biomarkers and morphology.

In some embodiments, the detection of the plurality of biomarkers may be determined simultaneously.

In some embodiments, the cell nuclei may be labeled with a panel of reagents selected from the group consisting of Hoechst 33258, Hoechst 33342, Hoechst 34580, 4',6'-diamidino-2-phenylindole (DAPI), cyanine nucleic acid stains, and hematoxylin.

In some embodiments, the score is used to determine the frequency of endoscopic surveillance in a subject with Barrett's esophagus or whether a patient is a candidate for therapeutic intervention to prevent progression of Barrett's esophagus. The therapeutic intervention may be an endoscopic ablation therapy, endoscopic photodynamic therapy, endoscopic cryotherapy, endoscopic mucosal resection, a surgical resection therapy, a non-endoscopic surgical therapy, or systemic therapy.

In some embodiments, the sample comprises a brushing, scraping, biopsy, or surgical resection of cells from the subject. The sample may be collected via random endoscopic sampling, computer-assisted endoscopic sampling, image-guided endoscopic sampling, or non-endoscopic sampling via brushing, abrasion or scraping.

In some embodiments, the sample may be at room temperature or frozen. The sample may be freshly obtained, formalin fixed, alcohol fixed, or paraffin embedded.

In certain embodiments, the method of detecting a field effect associated with malignant transformation of Barrett's esophagus in a subject, comprises: a) obtaining an upper gastrointestinal sample from the subject; b) labeling cell nuclei in the sample with a panel of reagents; c) labeling a plurality of biomarkers in the sample, wherein the plurality of biomarkers are p53, HIF-1α, COX2, p16, alpha-methylacyl-CoA racemase (AMACR), CD68, CD45RO, K20, and HER2/neu; d) detecting the labeled plurality of biomarkers and cell nuclei with an optical scanner; e) generating digital image data from the detected labeled plurality of biomarkers and cell nuclei; f) analyzing the labeled sample using a digital image platform for multi-channel fluorescence whole slide imaging to produce high dimensional quantitative image analysis features; g) analyzing the image analysis features associated with the plurality of biomarkers and cell nuclei, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity; h) determining a score using the combination of the image analysis features; and i) correlating the score to the probability of high grade dysplasia or esophageal cancer being present in the subject In some embodiments, the subject has an increased risk of progression to non-dysplastic intestinal metaplasia, reactive atypia, indefinite for dysplasia, low grade dysplasia, high grade dysplasia, or esophageal cancer.

In some embodiments, the subject has received a diagnosis of non-dysplastic intestinal metaplasia, reactive atypia, indefinite for dysplasia, low grade dysplasia, high grade dysplasia, or esophageal cancer.

In some embodiments, the plurality of biomarkers are detected using probes that specifically bind to each of the biomarkers. The probes may be fluorescent, contain a fluorescent tag, or may be detected via a secondary fluorescent probe or a secondary fluorescently tagged probe. Further, each probe may be labeled with a different fluorophore.

In some embodiments, the labeled plurality of biomarkers and cell nuclei may be imaged to produce fields of view that are analyzed to extract features associated with the biomarkers and morphology.

In some embodiments, the detection of the plurality of biomarkers may be determined simultaneously.

In some embodiments, the cell nuclei may be labeled with a panel of reagents selected from the group consisting of Hoechst 33258, Hoechst 33342, Hoechst 34580, 4',6'-diamidino-2-phenylindole (DAPI), cyanine nucleic acid stains, and hematoxylin.

In some embodiments, the score is used to determine the frequency of endoscopic surveillance in a subject with Barrett's esophagus or whether a patient is a candidate for therapeutic intervention to prevent progression of Barrett's esophagus. The therapeutic intervention may be an endoscopic ablation therapy, endoscopic photodynamic therapy, endoscopic cryotherapy, endoscopic mucosal resection, a surgical resection therapy, a non-endoscopic surgical therapy, or systemic therapy.

In some embodiments, the sample comprises a brushing, scraping, biopsy, or surgical resection of cells from the subject. The sample may be collected via random endoscopic sampling, computer-assisted endoscopic sampling, image-guided endoscopic sampling, or non-endoscopic sampling via brushing, abrasion or scraping.

In some embodiments, the sample may be at room temperature or frozen. The sample may be freshly obtained, formalin fixed, alcohol fixed, or paraffin embedded.

In certain embodiments, a kit for determining a risk of progression of Barrett's esophagus in a subject comprises: a) one or more reagents to label cell nuclei in a sample; b) one or more probes capable of detecting a plurality of biomarkers in the sample, wherein the plurality of biomarkers are p53, HIF-1α, COX2, p16, alpha-methylacyl-CoA racemase (AMACR), CD68, CD45RO, K20, and HER2/neu; and c) instructions for analyzing image analysis features associated with the plurality of biomarkers and cell nuclei, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, to generate a score from the sample of the subject.

In some embodiments, the score may be predictive of the clinical outcome of Barrett's esophagus in the subject, the risk of progression, or determinative of the preneoplastic stage of Barrett's esophagus in the subject and/or determinative of the presence of high grade dysplasia or esophageal cancer.

In some embodiments, the plurality of biomarkers are detected using probes that specifically bind to each of the biomarkers. The probes may be fluorescent, contain a fluorescent tag, or may be detected via a secondary fluorescent probe or a secondary fluorescently tagged probe. Further, each probe may be labeled with a different fluorophore.

In some embodiments, the cell nuclei may be labeled with a panel of reagents selected from the group consisting of Hoechst 33258, Hoechst 33342, Hoechst 34580, 4',6'-diamidino-2-phenylindole (DAPI), cyanine nucleic acid stains, and hematoxylin.

In certain embodiments, a kit for classifying Barrett's esophagus in a subject, comprises: a) one or more reagents to label cell nuclei in a sample; b) one or more probes capable of detecting a plurality of biomarkers in the sample, wherein the plurality of biomarkers are p53, HIF-1α, COX2, p16, alpha-methylacyl-CoA racemase (AMACR), CD68, CD45RO, K20, and HER2/neu; and c) instructions for analyzing image analysis features associated with the plurality of biomarkers and cell nuclei, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity, to generate a score from the sample of the subject.

In some embodiments, the score may be predictive of the clinical outcome of Barrett's esophagus in the subject, the risk of progression, or determinative of the preneoplastic stage of Barrett's esophagus in the subject and/or determinative of the presence of high grade dysplasia or esophageal cancer.

In some embodiments, the plurality of biomarkers are detected using probes that specifically bind to each of the biomarkers. The probes may be fluorescent, contain a fluorescent tag, or may be detected via a secondary fluorescent probe or a secondary fluorescently tagged probe. Further, each probe may be labeled with a different fluorophore.

In some embodiments, the cell nuclei may be labeled with a panel of reagents selected from the group consisting of Hoechst, 33258, Hoechst 33342, Hoechst 34580, 4',6'-diamidino-2-phenylindole (DAPI), cyanine nucleic acid stains, and hematoxylin.

In some embodiments of the methods described herein, the image data obtained using the optical scanner is analyzed as described in Prichard J W et al. TissueCypher: A Systems Biology Approach to Anatomic Pathology. Journal of Pathology Informatics. 2015; 6:48, which is hereby incorporated by reference in its entirety.

For example, in some embodiments, sections of formalin-fixed paraffin-embedded (FFPE) Barrett's biopsies were stained with H&E by standard histology methods. Additional sections can be labeled by multiplexed immunofluorescence for cytokeratin 20 (CK-20), Ki-67, b-catenin, p16, alpha-methylacyl-coenzyme A racemase (AMACR), p53, human epidermal growth factor receptor-2/neu (HER2/neu), CDX-2, CD68, nuclear factor kappa-B (NF-kB) p65, cyclooxygenase-2 (COX-2), hypoxia-inducible factor-1alpha (HIF-1a), CD45RO, CD1a plus Hoechst to label nuclei. The panel of biomarkers can also include biomarkers of stromal processes such as angiogenesis and specific immune cell subsets, e.g., macrophages. The biomarkers can, for example, be multiplexed in four-channel fluorescence sub-panels consisting of Hoechst and three biomarkers per slide. In some embodiments, slides are baked for 30 min at 60° C., dewaxed by immersion in Aqua DePar (Biocare Medical, Concord, Calif.), followed by epitope retrieval in Tris-ethylenediaminetetraacetic acid pH 9 buffer at 97-99° C. for 30 min then room temperature for 20 min. In some embodiments, slides are then washed, blocked first with Image-iT FX Signal Enhancer (Life Technologies, Carlsbad, Calif.) and then with 5% goat serum blocking buffer followed by incubation with a primary antibody cocktail containing (i) anti-CK-20, anti-Ki-67, and anti-b-catenin; (ii) anti-p16, anti-AMACR, and anti-p53; (iii) anti-HER2/neu, anti-CK-20, and anti-CDX-2; (iv) CD68, NF-kB p65, and anti-COX2; or (v) anti-HIF-1α, anti-CD45RO and anti-CD1a antibodies for about 1 h at room temperature. The antibodies can be any suitable antibody. In some embodiments, slides are washed and incubated for about 1 h at room temperature with a secondary antibody cocktail containing, for example, Alexa Fluors 488-, 555- and 647-conjugated goat-anti isotype-specific mouse and goat anti-rabbit IgG antibodies (Life Technologies), which are specific to each primary antibody cocktail. In some embodiments, slides are washed, labeled with Hoechst 33342 (Life Technologies) for about 3 min, washed again, and mounted with a glass coverslip using Prolong Gold Antifade (Life Technologies).

In some embodiments, H&E-stained slides are imaged at ×20 magnification. Fluorescently-labeled slides can, for example, be imaged by whole slide 4-channel fluorescence scanning at ×20 magnification on, for example, a ScanScope FL (Aperio Technologies/Leica BioSystems, Vista, Calif.) utilizing a BrightLine® Pinkel quadband filter set optimized for 4',6-diamidino-2-phenylindole, fluorescein isothiocyanate, tetramethylrhodamine, and Cy5 (FF01-440/521/607/700-25), and BrightLine® single-band bandpass excitation filters FF01-387/11-25, FF01-485/20-25, FF01-560/25-25, and FF01-650/13-25 (Semrock, Rochester, N.Y., USA). In some embodiments, a light source calibration device can be utilized to ensure the consistent illumination necessary for quantitative image analysis (Lumen Dynamics/Excelitas Technologies Corp., Waltham, Mass.).

The imaging analysis, can then include, for example, whole slide fluorescence image analysis. This method can include a high performance file reading mechanism based on BigTiff format to decode raw image data, MatLab algorithms for segmenting low level tissues objects such as nuclei, cytoplasm, plasma membrane, and whole cells to allow feature collection at the cellular and sub-cellular level and also higher order computer vision models for spatial quantification of biomarkers in tissue compartments, such as epithelium, metaplastic areas, and lamina propria. Further analysis can be performed as described in Prichard J W et al. TissueCypher: A Systems Biology Approach to Anatomic Pathology. Journal of Pathology Informatics. 2015; 6:48, which is hereby incorporated by reference in its entirety. Other methods of analysis can also be performed, which are similar to the methods described herein.

Although embodiments herein have been described in considerable detail with reference to certain preferred embodiments thereof, other versions are possible. Therefore the spirit and scope of the appended claims should not be limited to the description and the preferred versions contained within this specification.

EXAMPLES

Example 1

Background: Better methods are needed to predict risk of progression for Barrett's esophagus (BE). We aimed to determine whether a tissue systems pathology approach could predict progression in patients with non-dysplastic BE, indefinite for dysplasia, or low-grade dysplasia.

Methods: We performed a nested case-control study to develop and validate a classifying system that predicts progression of BE to high-grade dysplasia (HGD) or esophageal adenocarcinoma (EAC), based upon quantification of epithelial and stromal variables in baseline biopsies. Data were collected from patients in endoscopic surveillance programs at 4 institutions. Patients whose BE progressed to HGD or EAC in ≥1 year (n=79) were matched with patients whose BE did not progress (controls, n=287). Biopsies were assigned randomly to training or validation sets. Immunofluorescence analyses were performed for 14 biomarkers and quantitative biomarker and morphometric features were analyzed. Prognostic features were selected in the training set and combined into classifiers. The top-performing classifier was assessed in the validation set.

Results: A 3-tier, 15-feature classifier was selected in the training set and tested in the validation set. The classifier stratified patients into low-, intermediate- and high-risk classes (hazard ratio, 9.42; 95% confidence interval, 4.6-19.24 (high-risk vs low-risk); P<0.0001). It also provided independent prognostic information that outperformed predictions made based on pathology analysis, segment length, age, sex, or p53 overexpression.

Conclusion: We developed a tissue systems pathology test that better predicts risk of progression in BE than clinicopathologic variables.

Impact: The test has the potential to improve upon histologic analysis as an objective, quantitative method to risk stratify BE patients.

Study Design and Patients: A nested case-control study was constructed that utilized a multi-center cohort of BE patients in endoscopic surveillance programs with clinical outcome data from four institutions. BE cases with a diagnosis of metaplasia only or no dysplasia (ND), indefinite for dysplasia (IND) or low-grade dysplasia (LGD) were retrieved from Geisinger Health System, University of Pittsburgh, University of Pennsylvania and Academic Medical Center (AMC), Amsterdam, Netherlands. The diagnoses were confirmed by a single gastrointestinal (GI) subspecialist pathologist at each US institution (J. M. D. (University of Pittsburgh cases), N. C. J. (University of Pennsylvania cases), J. L. (Geisinger and AMC cases). Inclusion criteria were availability of tissue blocks and clinicopathologic data and confirmation of intestinal metaplasia. Exclusion criteria were prior history of HGD/EAC, diagnosis of HGD/EAC in less than 1 year of follow up, insufficient tissue quality as assessed by a pathologist, and preparation of tissue with Bouin's fixative or methylene blue. The earliest surveillance biopsy that satisfied inclusion/exclusion criteria was selected for each patient. Patients who progressed to HGD/EAC in ≥1 year (incident progressors/cases, n=41 training, n=38 validation) were matched to non-progressor controls with median HGD/EAC-free surveillance time of 5.6 years (n=142 training, n=145 validation) based on gender, segment length and age where possible. Case-control sets from the US and European institutions were randomly assigned to training or validation sets (Table 3). In the training set 33/41 progressor patients progressed to HGD and 8/41 to EAC and in the independent validation set, 29/38 progressor patients progressed to HGD and 9/38 to EAC (Table 4). Data elements collected were: case collection date, original pathologic diagnosis provided by a generalist pathologist and GI subspecialist pathologist review diagnosis for the case tested, date and original diagnosis of every surveillance biopsy, progression endpoint (HGD/EAC), HGD/EAC-free surveillance time (time between case tested and HGD/EAC diagnosis or last follow-up), age, sex, race and segment length (cm) and segment class (short ≤3 cm, long >3 cm). Segment length data was missing for 24 patients. Age and gender were complete for all patients. The original pathologic diagnosis extracted from the medical records was provided by a generalist pathologist for 304/366 patients and by a GI subspecialist pathologist for 62/366 patients.

TABLE 3

Patient Cases and Matched Controls

| | Training Set | | | | | | |
|---|---|---|---|---|---|---|---|
| | Non-Progressors | | | Incident Progressors | | | |
| # patients | 142 | | | 41 | | | |
| HGD/EAC-free surveillance time (Median years (IQR)) | 5.9 (4.5, 8.2) | | | 2.9 (2.3, 3.7) | | | |
| Age (mean years ± S.D.) | 56.5 ± 11.6 | | | 60.9 ± 12.2 | | | |
| Segment Length (%) | | | | | | | |
| Short (≤3 cm) | 63 (44.4) | | | 16 (39.0) | | | |
| Long (>3 cm) | 71 (50) | | | 24 (58.5) | | | |
| Unknown | 8 (5.6) | | | 1 (2.4) | | | |
| Gender (%) | | | | | | | |
| Male | 119 (83.8) | | | 32 (78) | | | |
| Female | 23 (16.2) | | | 9 (22) | | | |
| Patients in each diagnostic class based on GI subspecialist diagnosis (%) | ND 134 (94.4) | IND 3 (2.1) | LGD 5 (3.5) | ND 26 (63.4) | IND 1 (2.4) | LGD 14 (34.1) | |

| | Each Institution | | | | | | | |
|---|---|---|---|---|---|---|---|---|
| | AMC | Gei | UPenn | UPitt | AMC | Gei | UPenn | UPitt |
| # patients (%) | 46 (32.4) | 71 (50) | 16 (11.3) | 9 (6.3) | 25 (61.0) | 9 (22.0) | 1 (2.4) | 6 (14.6) |
| HGD/EAC-free surveillance time (median years (IQR) | 4.8 (4.2, 5.4) | 7.2 (5.9, 8.9) | 4.6 (3.2, 5.5) | 11.6 (7.3, 12.0) | 3.2 (2.9, 4.0) | 2.2 (1.4, 3.0) | 2.0 (N/A) | 2.5 (1.6, 3.3) |

| | Independent Validation Set | |
|---|---|---|
| | Non-Progressors | Incident Progressors |
| # patients | 145 | 38 |
| HGD/EAC-free surveillance time (Median years (IQR)) | 5.5 (4.1, 8.5) | 2.8 (2.0, 4.2) |
| Age (mean years ± S.D.) | 61.0 ± 12.1 | 60.1 ± 11.3 |
| Segment Length (%) | | |
| Short (≤3 cm) | 58 (40.0) | 10 (26.3) |
| Long (>3 cm) | 73 (50.3) | 27 (71.1) |
| Unknown | 14 (9.7) | 1 (2.6) |

TABLE 3-continued

Patient Cases and Matched Controls

Gender (%)

| | | | | | | | |
|---|---|---|---|---|---|---|---|
| Male | | 114 (78.6) | | | | 33 (86.8) | |
| Female | | 31 (21.4) | | | | 5 (13.2) | |
| Patients in each diagnostic class based on GI subspecialist diagnosis (%) | ND 138 (95.2) | IND 2 (1.4) | LGD 5 (3.4) | | ND 31 (81.6) | IND 2 (5.3) | LGD 5 (13.2) |

Each Institution

| | AMC | Gei | UPenn | UPitt | AMC | Gei | UPenn | UPitt |
|---|---|---|---|---|---|---|---|---|
| # patients (%) | 46 (31.7) | 63 (43.5) | 15 (10.3) | 21 (14.5) | 28 (73.7) | 4 (10.5) | 3 (7.9) | 3 (7.9) |
| HGD/EAC-free surveillance time (median years (IQR) | 5.0 (4.0, 7.8) | 6.5 (4.2, 10.1) | 4.1 (3.5, 4.8) | 6.3 (5.6, 8.6) | 2.8 (2.3, 4.3) | 2.1 (1.4, 4.7) | 1.7 (1.0, 3.9) | 3.1 (1.5, 5.5) |

*surveillance time: number of days between biopsy tested and last endoscopy with ND, IND or LGD (non-progressors) or endoscopy with diagnosis HGD or EAC (incident progressors). Diagnosis provided by GI subspecialist pathologist for all patients. Original diagnosis provided by a generalist pathologist was available for 160 patients in the training set and 144 patients in the validation set.
AMC: Academic Medical Center, Netherlands;
Gei: Geisinger Health System;
UPenn: University of Pennsylvania;
UPitt, University of Pittsburgh.
S.D.: standard deviation,
IQR: interquartile range.

TABLE 4

Summary of Progression Endpoints in Incident Progressor Patients

| | Training Set | | | Independent Validation Set | | |
|---|---|---|---|---|---|---|
| # Incident Progressor Patients (all four institutions combined) | 41 | | | 38 | | |
| # Incident Progressor Patients in each Dx class | ND 26 | IND 1 | LGD 14 | ND 31 | IND 2 | LGD 5 |
| Progression Endpoint (HGD or EAC) | 19 HGD 7 EAC | 1 HGD 0 EAC | 13 HGD 1 EAC | 22 HGD 9 EAC | 2 HGD 0 EAC | 5 HGD 0 EAC |

| | AMC | Gei | UPenn | UPitt | AMC | Gei | UPenn | UPitt |
|---|---|---|---|---|---|---|---|---|
| # Incident Progressor Patients (each institution) | 25 | 9 | 1 | 6 | 28 | 4 | 3 | 3 |
| Progression Endpoint (HGD or EAC) | 19 HGD 6 EAC* | 8 HGD 1 EAC | 1 HGD 0 EAC | 5 HGD 1 EAC | 22 HGD 6 EAC* | 2 HGD 2 EAC | 3 HGD 0 EAC | 2 HGD 1 EAC |

*early stage esophageal adenocarcinomas

Candidate Biomarker Selection: The following candidate panel of 14 protein biomarkers was selected and examined in the study: K20 (cytokeratin-20), Ki-67, β-catenin, p16INK4a, AMACR (alpha-methylacyl-CoA racemase), p53, HER2/neu, CDX-2, CD68, NF-κB-p65, COX-2 (cyclo-oxygenase-2), HIF-1α (hypoxia-inducible factor 1-alpha subunit), CD45RO, and CD1a. The biomarkers included markers of epithelial cell abnormalities that have been described in the progression of BE and also stromal biomarkers known to play a role in carcinogenesis.

Fluorescence Immunolabeling: 5 μm sections of formalin-fixed paraffin-embedded (FFPE) BE biopsies were stained with H&E by standard methods. Additional sections were labeled by multiplexed immunofluorescence for the candidate biomarker panel listed above, plus Hoechst labeling, according to previously described methods. The biomarkers were multiplexed in sub-panels consisting of Hoechst and 3 biomarkers/slide detected via Alexa Fluor-488, -555 and -647-conjugated secondary antibodies (Life Technologies, Carlsbad, Calif.).

Whole Slide Imaging: H&E-stained slides were imaged at 20× magnification on a NanoZoomer Digital Pathology scanner (Hamamatsu Photonics, K.K., Japan). Fluorescently-immunolabeled slides were imaged at 20× on a ScanScope FL (Aperio Technologies/Leica BioSystems, Vista, Calif.) with a calibrated light source as previously described. A standardized imaging procedure was used that included set exposure times.

Image Analysis: Whole slide fluorescence images were analyzed using the TissueCypher™ Image Analysis Platform (Cernostics, Inc., Pittsburgh, Pa.), which produces high dimensional quantitative feature data on biomarkers and morphology. The platform utilizes algorithms for segmenting cell-based objects to allow quantitative biomarker and morphology feature data collection at the cellular and subcellular level. The platform also employs computer vision models to quantify biomarkers in epithelium, metaplasia and lamina propria. Features (continuous, quantitative measurements of biomarkers and/or morphology) included biomarker intensities and coexpression within appropriate subcellular compartments and tissue compartments, morphometrics and microenvironment-based biomarker measurements. Features were extracted from the candidate biomarkers and morphology. 1,184 image analysis features/biopsy were extracted by the software, and summarized as multiple measures, (percentiles, IQR, percent positive, spatial summary statistics) resulting in 13,538 feature/measures per biopsy. The image analysis software was blind to the case-control status of the samples.

Statistical Analyses: A risk prediction classifier was developed within the training set and prospectively defined prior to testing in the validation set. We tested the hypothesis that patients in the predicted low-risk class have significantly lower risk for progression to HGD/EAC than patients in the predicted high-risk class. We also tested the hypothesis that the risk classes would add independent prognostic information beyond that of the pathologic diagnosis and segment length.

Development of Risk Prediction Model: Univariate conditional logistic regression was performed in the training set with the 13,538 feature/measures to compare non-progressors to progressors and enable feature selection for multivariable model building. Selected features were combined into classifiers and leave-one-out cross validation (LOOCV) was performed to estimate prognostic performance of the classifiers. In each iteration of LOOCV, 1 case-control group (progressor and matched non-progressors) was set aside and the remaining case-control groups were used as the training set. The prediction model was built in the training set by the sum of the features weighted by the univariate Cox coefficients, and then this model was applied on the testing cases to calculate a score. The LOOCV process was repeated until all case-control groups were treated as the testing case once. The end result of the LOOCV process was a risk score for each patient ranging from 0-10. Survival time for Cox proportional hazards regression was defined as the time between the case tested in this study and the diagnosis of HGD/EAC for progressors or last follow-up for non-progressors. Cox regression was only used after the features had been selected (by conditional logistic regression) in order to derive the weights for these selected features to compute a risk score for the prediction model, and there are striking similarities between the conditional logistic likelihood function and the partial likelihood function used to fit a Cox proportional hazards model. Concordance-indices (C-indices) were calculated and Receiver Operating Characteristic (ROC) curves based on the binary outcome of low/high for 5-year risk of progressing to HGD/EAC were plotted. Cutoffs were determined to stratify patients into low-, intermediate- and high-risk classes. The cutoffs were chosen to achieve negative predictive value (NPV) and positive predictive value (PPV) of greater than 95% and 65%, respectively, unadjusted for disease prevalence in the training set. Kaplan-Meier (KM) curves were used to represent the probability of progression to HGD/EAC in the 3 risk classes. Hazard ratios (HRs) with 95% confidence intervals (C.I.) were calculated from Cox proportional hazards regression and odds ratios (ORs) with 95% C.I. were calculated from the conditional logistic regression. Log-rank test was used to assess the equality of probability of progression curves of the risk groups from KM analysis, while score test was performed with conditional logistic regression to examine the significance of association of the risk groups with incidence of HGD/EAC.

Independent Validation of Risk Prediction Model: The independent validation set was quarantined during the training phase. Sample size calculations indicated that a total of 43 patients were required in the validation set to ensure 80% power to detect a significant difference of 50% in the 5-year risk of progression to HGD/EAC between those classified as high-risk vs those as low-risk, at 0.05 significance level. All assay parameters were pre-specified, including the 15 feature/measures, coefficients and classifier cutoffs prior to testing on the validation set. The risk score for each patient was calculated and risk classes were assigned based on the established cutoffs. Prevalence-adjusted NPV and PPV were calculated for the predicted low- and high-risk groups based on previously reported yearly progression rates for BE patients with GI subspecialist diagnosis of ND, IND and LGD of 0.6%, 0.9% and 9.1%, respectively.

Comparison of Classifier Performance versus Clinical Variables: Multivariate Cox models were performed to assess whether the test, both as categorical classes and a continuous variable, would add independent prognostic information beyond traditional clinical factors. The following variables were dichotomized: diagnosis ((LGD versus ND/IND combined, sex (0 for F, 1 for M), segment length (0 for short, 1 for long). Percent cells overexpressing p53 (determined by the image analysis) and age were evaluated as continuous variables. Patients with missing segment length and/or original generalist pathologist diagnosis were excluded from the multivariate Cox models.

Results: The nested case-control cohort included pre-progression samples from 79 (n=41 in training set, n=38 in validation set) BE patients with ND, IND or LGD who progressed to HGD or EAC at least 1 year later and 287 samples from matched control patients who did not show progression (n=142 in training set, n=145 in validation set). Case-control sets from the US and European institutions were randomly assigned to either the training or validation set. The non-progressor patients had a median HGD/EAC-free surveillance time of 5.9 (IQR 4.5, 8.2) and 5.5 years (IQR 4.1, 8.5) in the training and validation sets, respectively. The median time-to-progression was 2.9 (IQR 2.3, 3.7) and 2.8 (IQR 2.0, 4.2) years in the training and validation sets, respectively. The clinical characteristics of the patients are summarized in Table 3.

Development of 15-Feature Classifier in the Training Set: Whole slide fluorescence images of multiplexed biomarker labeling were analyzed by image analysis software to generate 13,538 feature/measures per biopsy in the training set. A set of 17 image analysis features derived from p53, HER2, Ki-67, K20, COX2, CD68, HIF-1α, p16INK4A, AMACR, CD45RO and nuclear morphology were selected based on p-values from univariate conditional logistic regression comparing cases versus controls (Table 5).

TABLE 5

17 Candidate Image Analysis Features (Including Top 15 Features Utilized by Risk Classifier)

| Biomarker | Image Analysis Feature | P value | P value Adjusted by Diagnosis | Coefficient | Utilized by 15-Feature Risk Classifier |
|---|---|---|---|---|---|
| p53 | p53 nuclear sum intensity | 3.81E−05 | 5.81E−05 | −8.04439 | ✓ |
| p53 | p53 nuclear mean intensity | 7.48E−05 | 0.000116779 | 6.358257 | ✓ |
| HER2/neu and K20 | Ratio of mean HER2/neu intensity:mean K20 intensity in nuclei clusters | 0.000155084 | 0.000312461 | 4.547325 | ✓ |
| HER2/neu and K20 | Ratio of 95th quantile HER2/neu intensity:95th quantile K20 intensity in nuclei clusters | 0.000318651 | 0.00064884 | 4.286031 | ✓ |
| COX2 and CD68 | Coexpression cellular COX2 mean intensity and cellular CD68 mean intensity | 0.00046706 | 0.000911804 | −0.02203 | ✓ |
| p53 | p53 mean intensity in nuclei clusters | 0.000501393 | 0.000498535 | 3.099642 | ✓ |
| p53, p16 and nuclear morphology (solidity) | Nuclear solidity in p53+ p16− cells | 0.000866951 | 0.00126554 | 15.62477 | ✓ |
| CD45RO | CD45RO plasma membrane sum intensity | 0.000873155 | 0.002141764 | −3.76449 | ✓ |
| AMACR | AMACR microenvironment standard deviation | 0.000924663 | 0.001502611 | 0.000789 | ✓ |
| COX2 | COX2 texture in cytoplasm* | 0.001318862 | 0.001909437 | 10.39816 | ✓ |
| HIF1alpha | HIF-1α microenvironment cell mean intensity | 0.001758646 | 0.001040583 | 0.000349 | ✓ |
| HIF1alpha | HIF-1α microenvironment cell moment (product of mean and standard deviation) | 0.002189596 | 0.002420038 | 1.02E−06 | ✓ |
| p16 | p16 cytoplasm mean intensity | 0.00352243 | 0.003240205 | −4.98699 | ✓ |
| p53, p16 and nuclear morphology (area) | Nuclear area in p53+ p16− cells | 0.00386791 | 0.005517011 | 0.014368 | ✓ |
| Nuclear morphology | Hoechst nuclear 95th quantile intensity | 0.022822291 | 0.03429373 | 10.78732 | ✓ |
| Ki-67 and K20 | Ratio of 95th quantile Ki-67 intensity:95th quantile K20 intensity in nuclei clusters | 0.279157 | 0.340456 | 0.95634 | x |
| Ki-67 and K20 | $95^{th}$ quantile Ki-67 intensity in nuclei of metaplastic cells | 0.10297 | 0.053479 | 1.73172 | x |

Univariate conditional logistic regression was performed with the 13,538 feature/measures extracted by the image analysis to compare non-progressors (controls) versus incident progressors (cases) in the training set of BE patients. The table lists the selected subset of 17 features derived from 10 biomarkers and nuclear morphology that showed significant differences in incident progressors versus non-progressors. This set of 17 features was entered into the multivariable model building. P-values shown are estimated from the conditional logistic regression. Coefficients were derived from Cox proportional hazards regression of each feature/measure.

*Contrast textural feature is extracted from a co-occurrence matrix and is a measure of the COX2 intensity contrast between a pixel and its neighbor over the whole tissue image, as described by Haralick et al., IEEE Transactions On Systems, Man and Cybernetics, SMC-3: 610-621 (1973).

Features derived from CDX2, β-catenin, CD1a and NF-κB p65 were not selected due to low ranking based on p-values. The false discovery rate (FDR) during the feature selection process was examined to control the potential chance errors due to multiple testing. The FDR for the top 17 features selected during the classifier development process was 0.025%. Therefore, the likelihood that a feature in the set of 17 features was selected by random chance was negligible. The most significant measure for each of the selected 17 image analysis features based on univariate conditional logistic regression was selected and used in building predictive models. The top 3, 6, 9, 12, 15 and 17 image analysis feature/measures based on p-values from conditional logistic regression were scaled using the center and scale parameters derived from the training set. The weighted (by univariate Cox model coefficients) sum was calculated to produce a risk score. 98% of the raw scores ranged from −10 to 10. Scaling was performed to ensure that the risk score ranged from 0-10 using the following formula:

$$\text{score} = \begin{cases} 0 & \text{if raw score} < -10 \\ \dfrac{\text{raw score} + 10}{2} & \text{if } -10 < \text{raw score} < 10 \\ 10 & \text{if raw score} > 10 \end{cases}$$

Figure 2A:
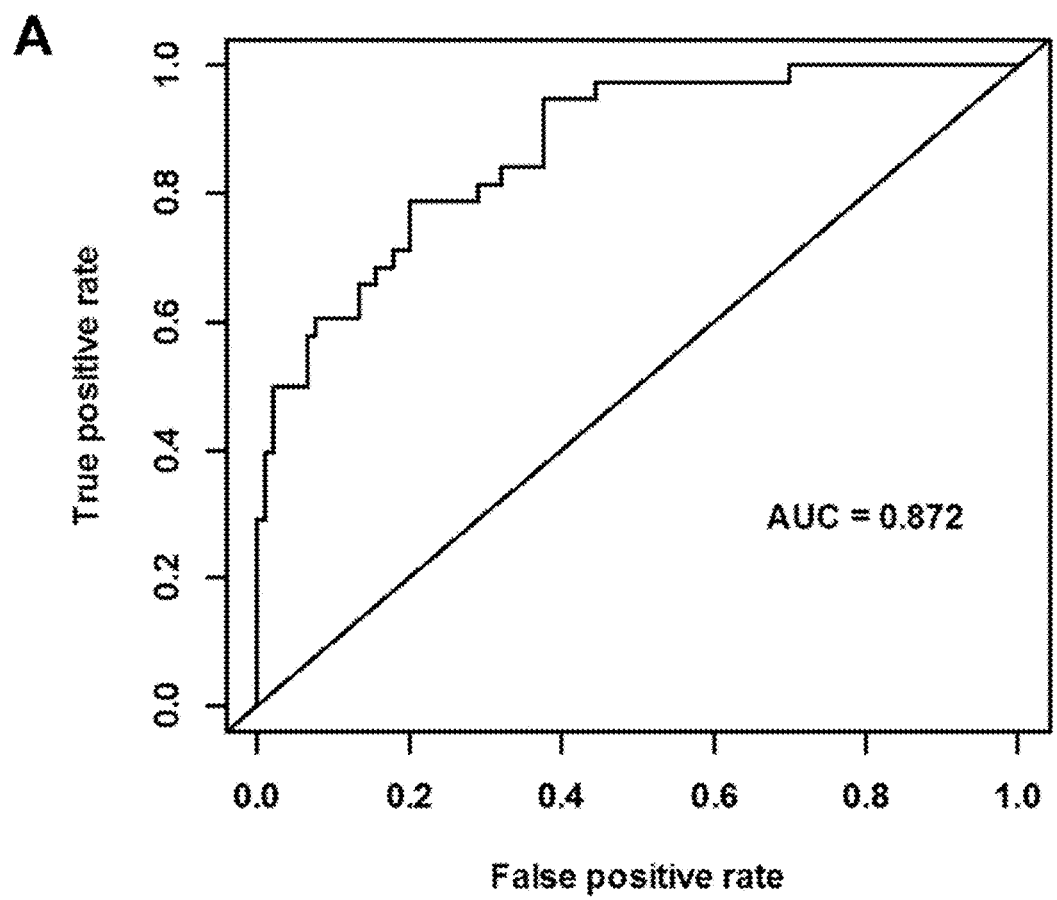
Figure 5:
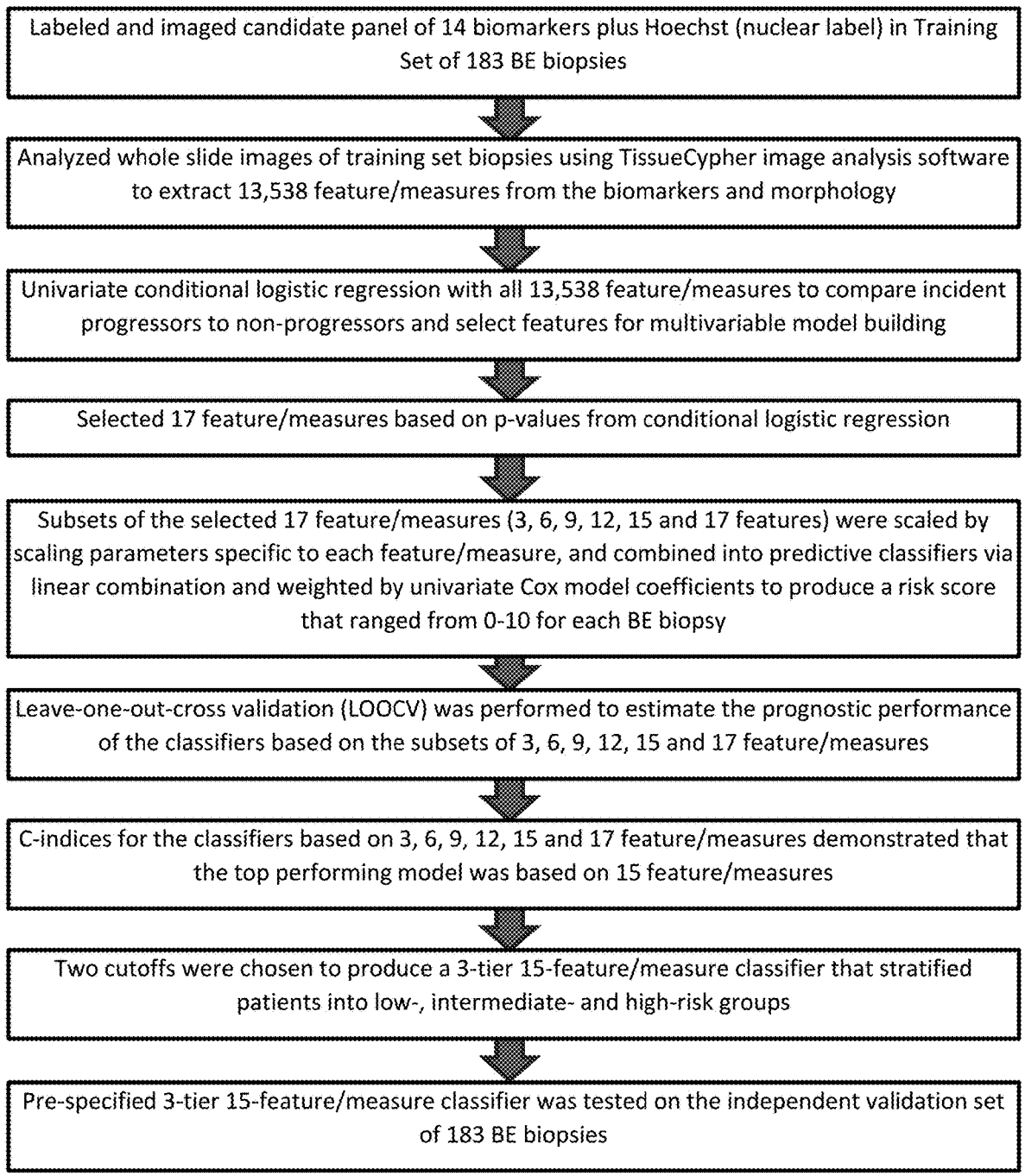
FIG. 5. Flowchart of Steps to Train and Validate 3-Tier 15-Feature/Measure Classifier for Risk Prediction in Barrett's Esophagus Biopsies.

Using the risk scores generated by these classifiers through LOOCV, C-indices for the top 3, 6, 9, 12, 15 and 17 features were 0.674, 0.672, 0.716, 0.755, 0.797 and 0.792, respectively, demonstrating that the top performing model was based on 15 image analysis feature/measures. The 15 feature/measures were derived from p53, HER2, K20, COX2, CD68, HIF-1α, p16INK4A, AMACR, CD45RO and nuclear morphology and included multiple image analysis features derived from individual biomarkers (Table 5). A flowchart detailing the steps to develop the classifier is included (FIG. 5). Expression patterns of the biomarkers on which the 15-feature classifier is based are shown in FIG. 1 for representative progressor patients. AUROC (area under receiver operating characteristic curve) for the 15-feature classifier was 0.872 in patients from all four institutions (FIG. 2A), 0.842 in US patients and 0.870 in AMC patients, indicating high prognostic accuracy.

Figure 2B:
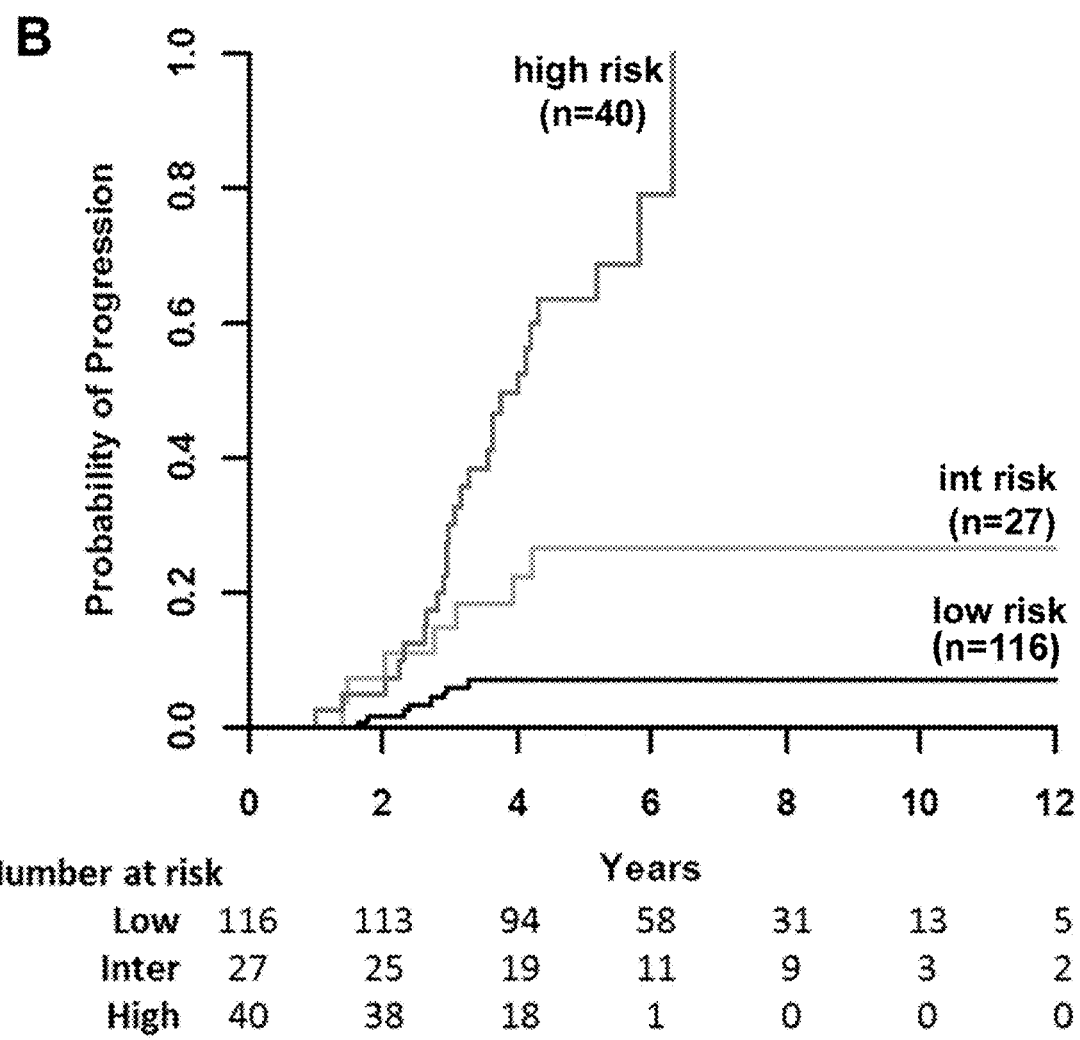
Figure 2C:
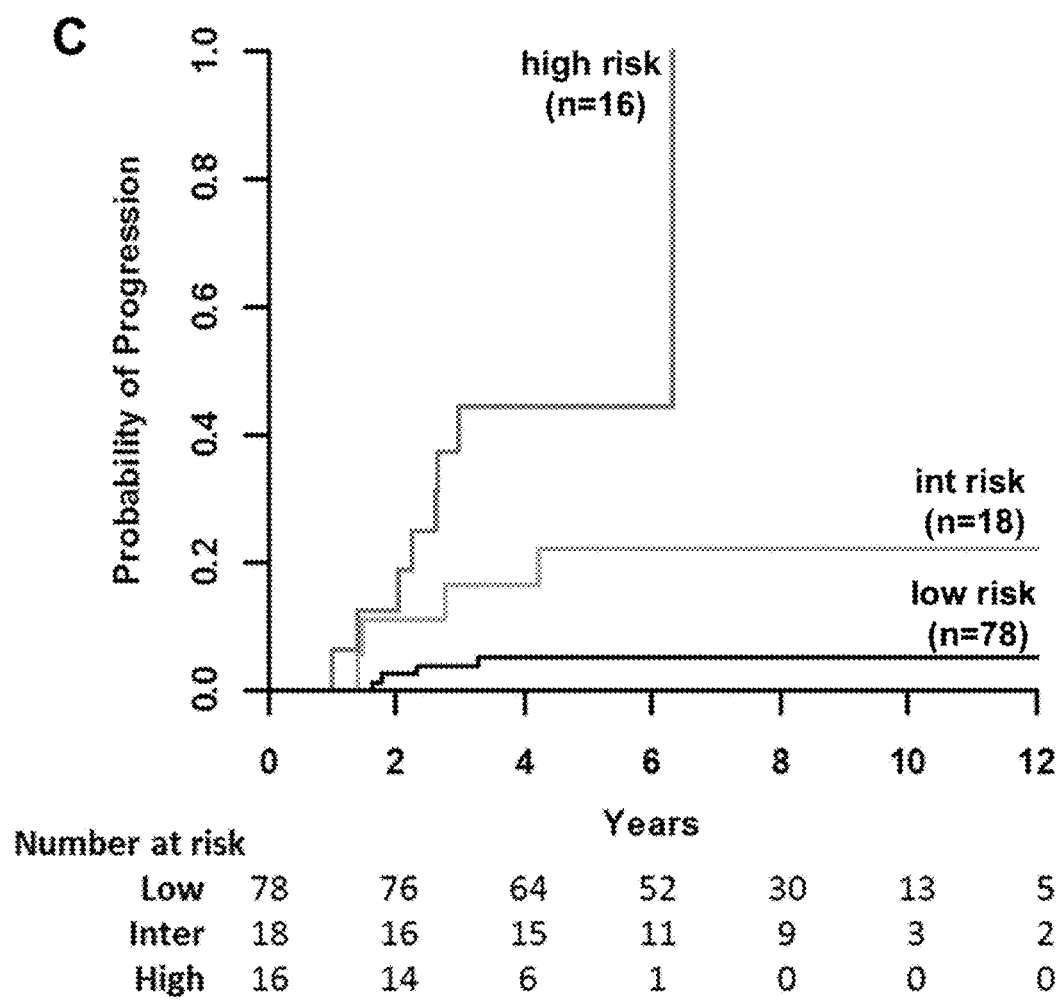
Figure 2D:
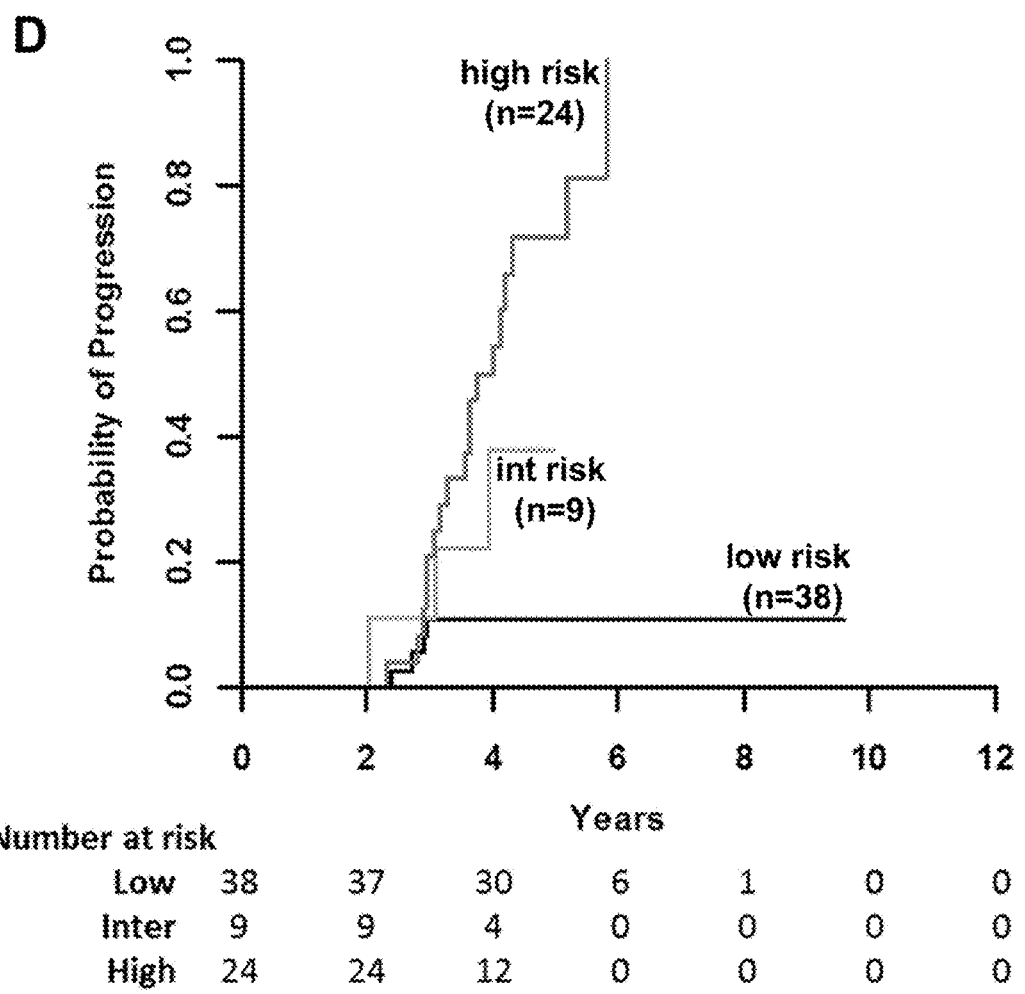

Two cutoffs were chosen to produce a 3-tier classifier that stratified patients into low-, intermediate- and high-risk groups. Kaplan-Meier (KM) plots of the 5-year probability of progression to HGD/EAC in patients scored as low-, intermediate- and high-risk demonstrated that the classifier stratified progressors from non-progressors in all institutions combined and in US and AMC patients separately (FIG. 2B-FIG. 2D). HRs were 4.19 (95% C.I. 1.52, 11.57) for intermediate-vs. low-risk and 14.73 (95% C.I. 6.55, 33.16) for high-vs. low-risk. Both the log-rank and score tests showed that the 3 risk classes predicted by the classifier had different risk for progression to HGD/EAC (p<0.0001).

Figure 3A:
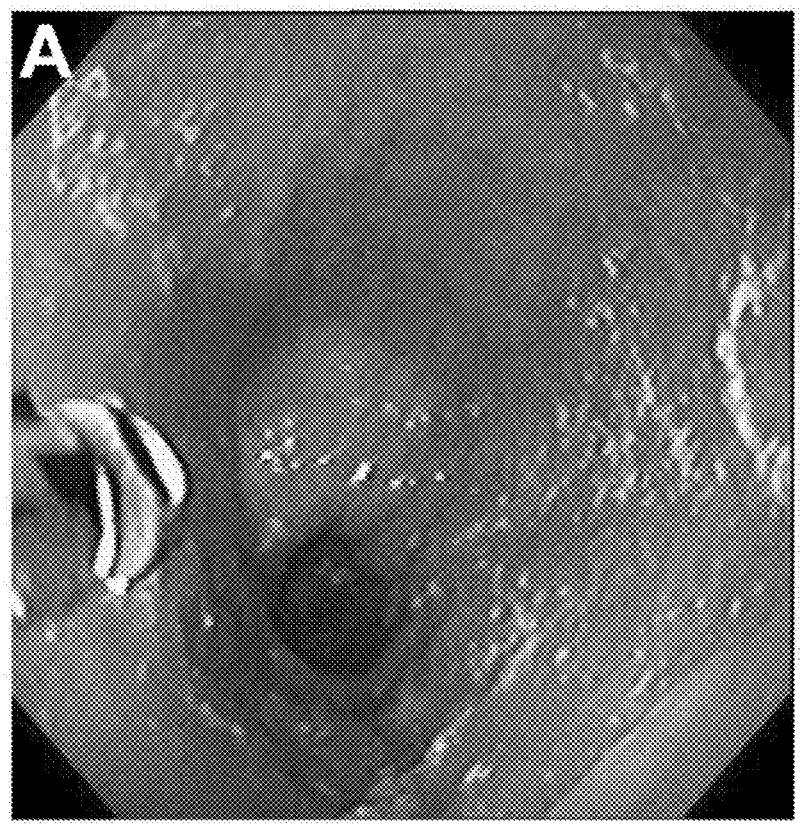
FIG. 3A-FIG. 3F. Detection of High Risk Features that Precede Morphologic Changes in BE. Endoscopy, H&E and multiplexed fluorescence biomarker images are shown for an incident progressor (IP) (FIG. 3A, FIG. 3B, and FIG. 3C) and a non-progressor (NP) (FIG. 3D, FIG. 3E, and FIG. 3F) with GI subspecialist diagnosis of BE ND. The IP patient progressed to HGD (high grade dysplasia) 6.3 years later and was scored high-risk by the 15-feature classifier. The NP patient had 7.8 years of endoscopic surveillance showing no progression to HGD/EAC and was scored low-risk.
Figure 3B:
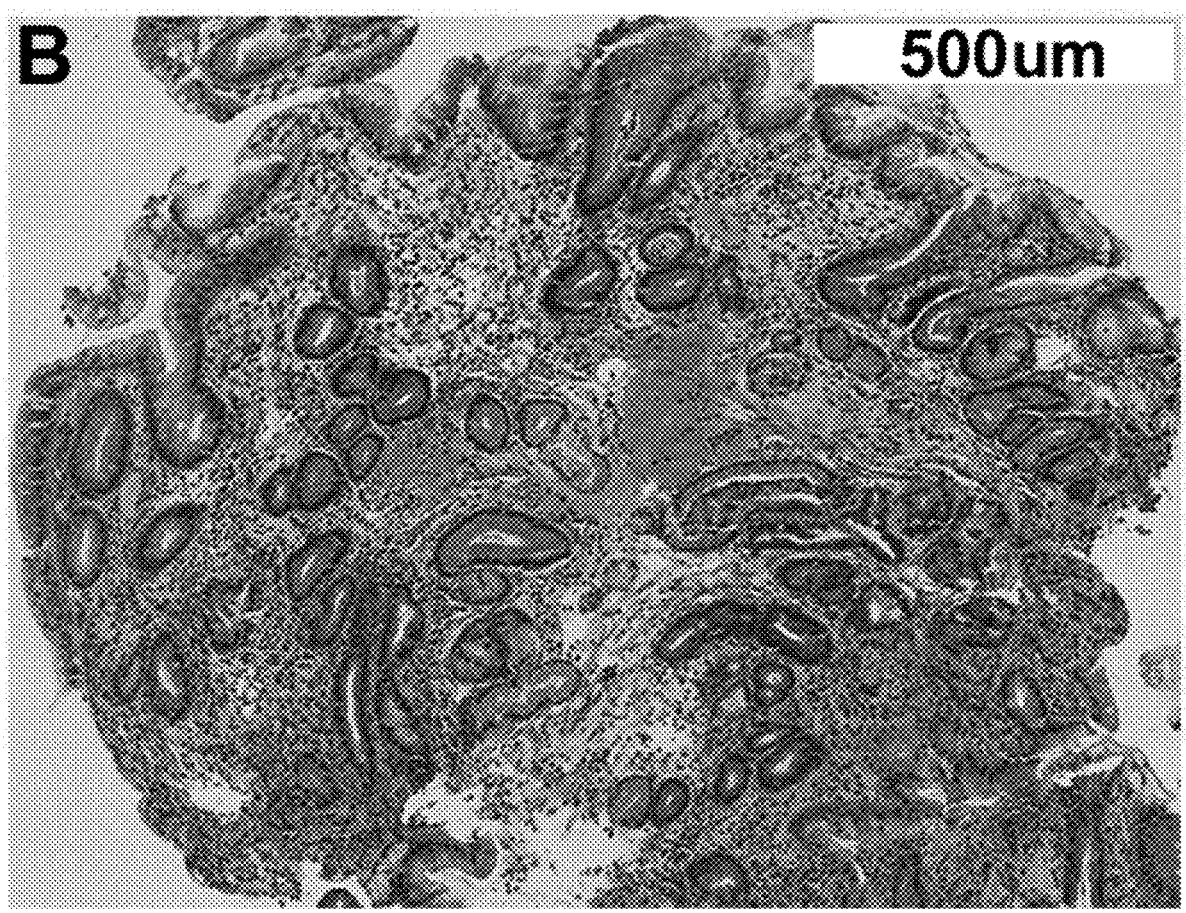
Figure 3C:
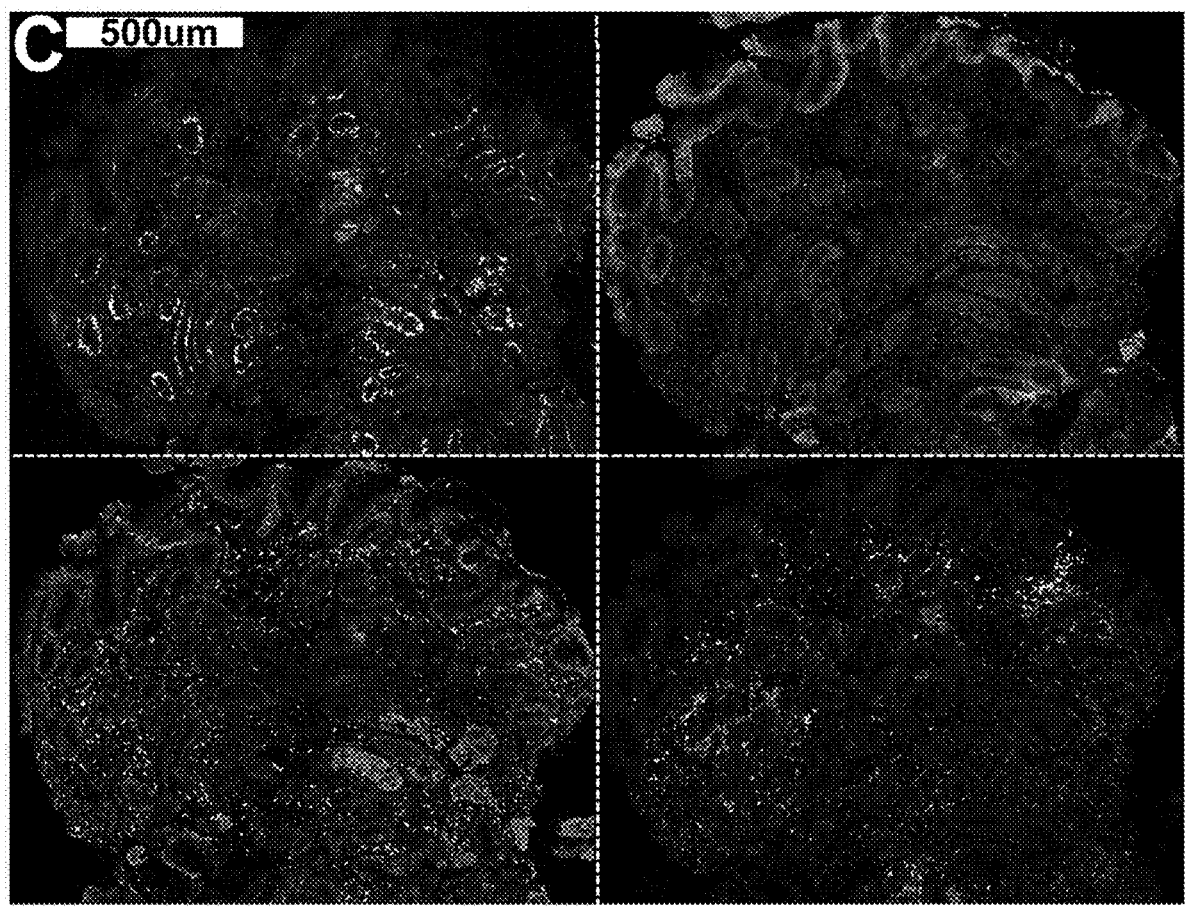
Figure 3D:
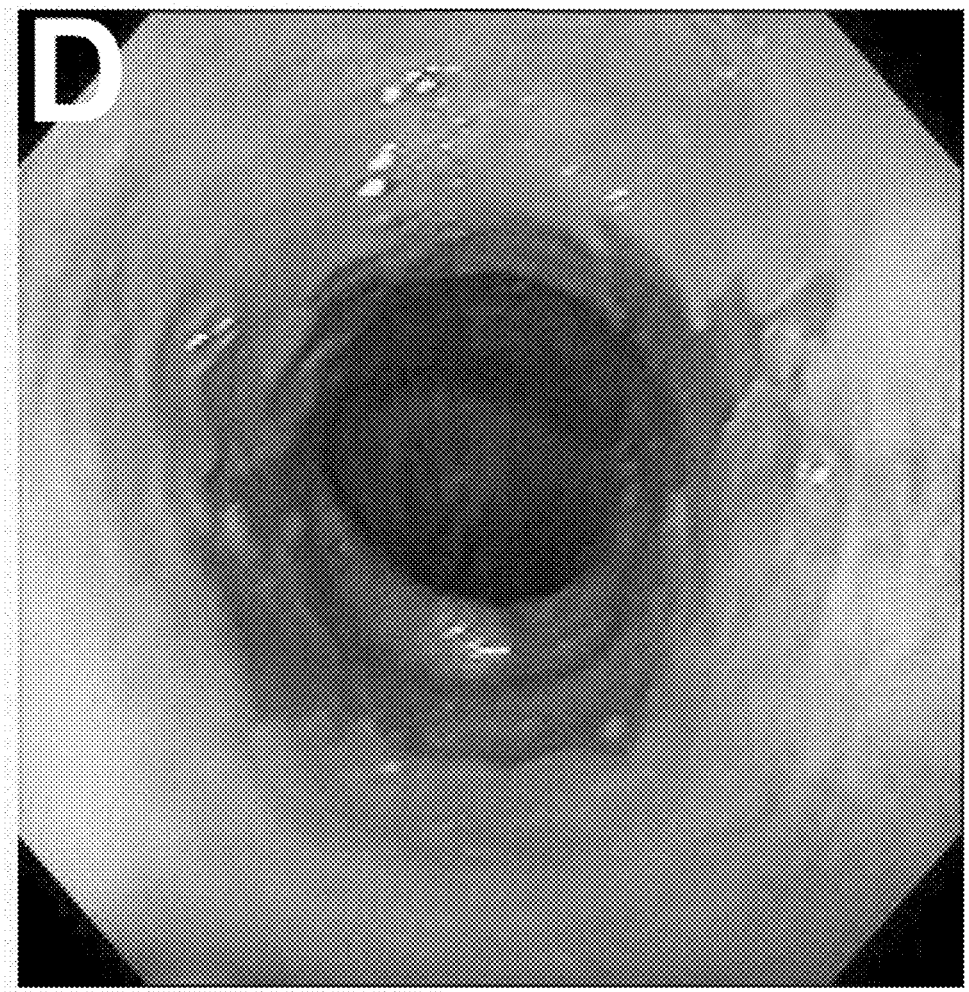
Figure 3E:
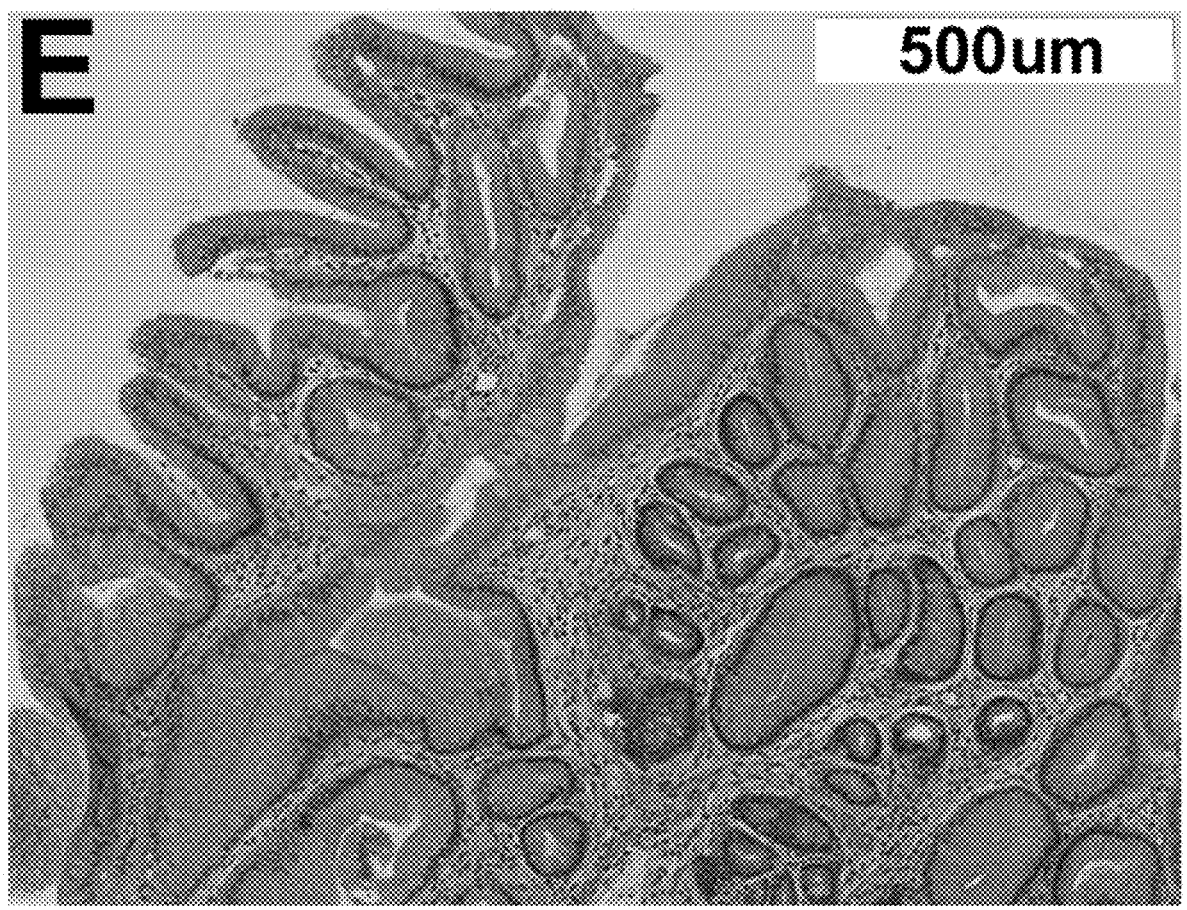
Figure 3F:
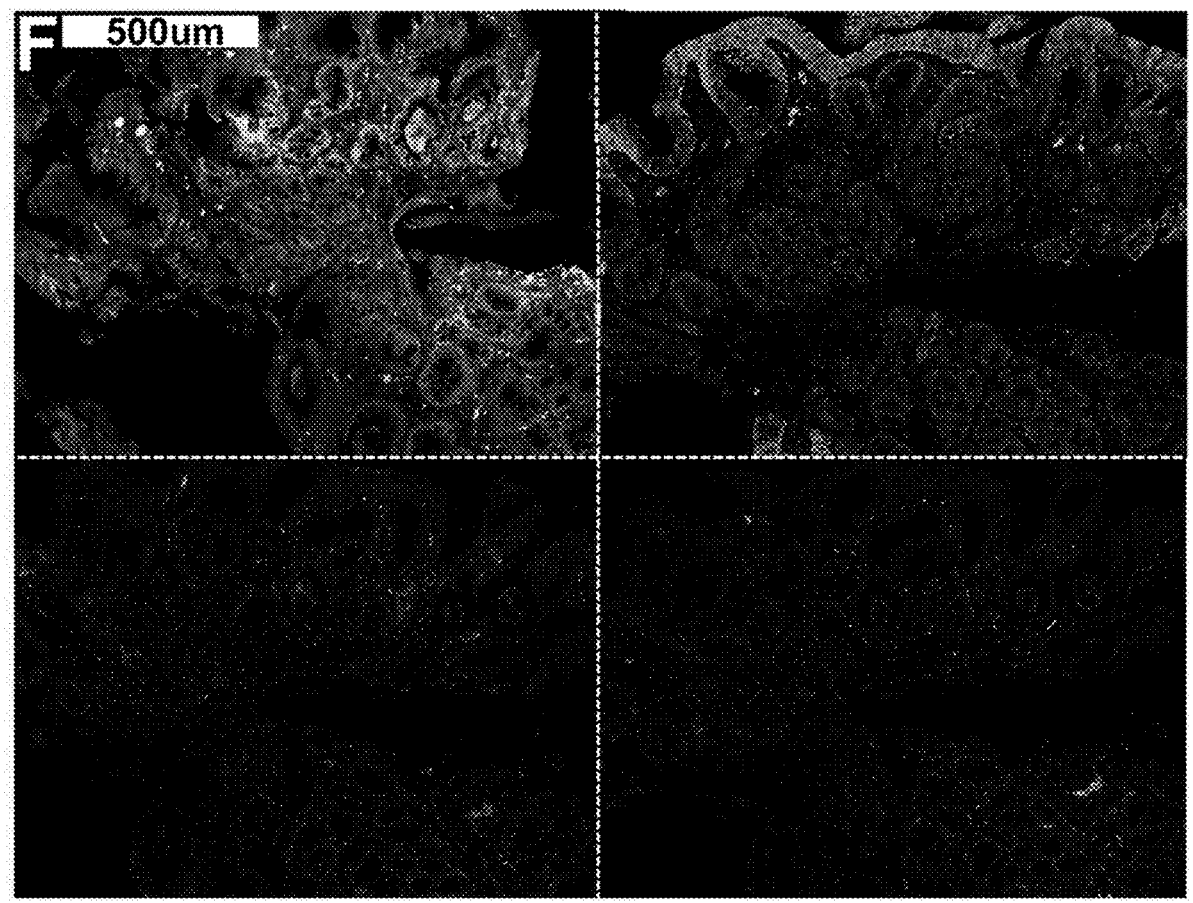

The molecular and cellular changes that are captured by the 15-feature classifier are illustrated in FIG. 3, which compares endoscopy images, H&E-stained BE biopsy images and images of multiplexed fluorescence labeling of the 9 biomarkers on which the classifier is based in a progressor (FIG. 3A-FIG. 3C) and a non-progressor (FIG. 3D-FIG. 3F). Endoscopy images for both patients showed BE with no apparent visible lesions (FIG. 3A and FIG. 3D). Biopsies from both patients were confirmed as ND by a GI subspecialist pathologist (FIG. 3B and FIG. 3E). The 15-feature classifier scored the progressor high-risk due to multiple molecular and cellular changes (FIG. 3C), which included overexpression of p53, HER2/neu and COX-2 and infiltration by macrophages, memory lymphocytes and stromal cells expressing HIF-1α. The non-progressor was scored low-risk due to absence of high-risk features (FIG. 3F).

In multivariate Cox models in which progression to HGD/EAC was evaluated first in relation to clinical variables alone, then in relation to the predicted risk classes added to the clinical variables, the intermediate-risk and high-risk classes provided prognostic power that was independent of the pathologist's diagnosis (both general and GI subspecialist), segment length, age, sex and percent cells overexpressing p53 (Table 6). The subspecialist diagnosis and age were also significant predictors. However, the mean age was higher in progressors than in non-progressors (Table 3). The magnitude of HRs indicated that the predicted risk classes provided stronger prognostic power than the clinical variables (Table 6). Similar results were observed when the 15-feature risk score was evaluated as a continuous variable (Table 7).

TABLE 6

Comparison of Predictive Performance of Risk Classes Predicted by Test vs. Clinical Variables in Training Set of BE Patients

| Variable | Multivariate Hazard Ratio (95% CI) | P Value |
|---|---|---|
| A. Prognostic Performance of Risk Classes vs. Clinical Variables* | | |
| Analysis without Risk Prediction Test | | |
| General Pathologist's Dx (LGD vs. ND/IND) | 2.17 (1.05-4.47) | 0.04 |
| BE segment length (Long vs. Short) | 1.09 (0.55-2.19) | 0.8 |
| Age | 1.03 (0.99-1.06) | 0.12 |
| Gender | 0.85 (0.37-1.97) | 0.71 |
| p53 (% cells overexpressing) | 4.23 (0.09-202.5) | 0.46 |
| Analysis with Risk Prediction Test | | |
| General Pathologist's Dx (LGD vs. ND/IND) | 1.57 (0.74-3.37) | 0.24 |
| BE segment length (Long vs. Short) | 1 (0.49-2.03) | 1 |
| Age | 1.05 (1.02-1.09) | 0.002 |
| Gender | 1.74 (0.68-4.46) | 0.25 |
| p53 (% cells overexpressing[1]) | 0.05 (0-4.18) | 0.19 |
| Risk Classes (predicted by test) | | |
| Intermediate Risk vs. Low Risk | 8.08 (2.65-24.65) | 0.0002 |
| High Risk vs. Low Risk | 33.02 (11.8-92.44) | <0.0001 |
| B. Prognostic Performance of Risk Classes vs GI Subspecialist Diagnosis** | | |
| Analysis without Risk Prediction Test | | |
| GI Subspecialist Pathologist's Dx (LGD vs. | 6.8 (3.54-13.06) | <0.0001 |
| Analysis with Risk Prediction Test | | |
| GI Subspecialist Pathologist's Dx (LGD vs. | 3.25 (1.57-6.75) | 0.002 |
| Risk Classes (predicted by test) | | |
| Intermediate Risk vs. Low Risk | 4.64 (1.67-12.87) | 0.003 |
| High Risk vs. Low Risk | 10.98 (4.67-25.81) | <0.0001 |

Multivariate Cox models were run in which progression to HGD/EAC was evaluated first in relation to clinical variables alone, then in relation to risk classes predicted by the test and clinical variables in non-progressor patients and incident progressor patients. The following clinical variables were dichotomized: pathologist diagnosis (LGD vs. ND or IND), gender (0 for F, 1 for M), BE segment length (0 for short (≤3 cm), 1 for long (>3 cm) and Risk Classes (high vs. low risk and intermediate vs. low risk). Age and p53 were evaluated as continuous variables.
*n = 35 incident progressor patients and n = 116 non-progressor patients with complete data for all evaluated variables.
**n = 41 incident progressor patients and n = 142 non-progressor patients (all training set patients) for analysis in part B.
[1] calculated by the image analysis software (percentage of cells with nuclei p53 mean intensity >95 on a scale of 0-1023 in the 10 bit tissue images).

TABLE 7

Comparison of Predictive Performance of Risk Score as a Continuous Variable vs. Clinical Variables in Training Set

| Variable | Hazard Ratio (95% CI) | P Value |
|---|---|---|
| A. Multivariate Cox Analysis of Risk Score vs. Clinical Variables* | | |
| Analysis without Risk Score | | |
| General Pathologist's Dx (LGD vs. ND/IND) | 2.17 (1.05-4.47) | 0.04 |
| BE segment length (Long vs. Short) | 1.09 (0.55-2.19) | 0.8 |
| Age | 1.03 (0.99-1.06) | 0.12 |
| Gender | 0.85 (0.37-1.97) | 0.71 |
| p53 (% cells overexpressing) | 4.23 (0.09-202.5) | 0.46 |
| Analysis with Risk Score | | |
| General Pathologist's Dx (LGD vs. ND/IND) | 1.59 (0.73-3.47) | 0.25 |
| BE segment length (Long vs. Short) | 0.88 (0.42-1.82) | 0.73 |
| Age | 1.05 (1.02-1.09) | 0.003 |
| Gender | 1.53 (0.6-3.91) | 0.38 |
| p53 (% cells overexpressing) | 0.01 (0-1.66) | 0.08 |
| Continuous Risk Score | 1.94 (1.61-2.35) | <0.0001 |
| B. Multivariate Cox Analysis of Risk Score vs GI Subspecialist Diagnosis** | | |
| Analysis without Risk Score | | |
| GI Subspecialist Pathologist's Dx (LGD vs. | 6.8 (3.54-13.06) | <0.0001 |
| Analysis with Risk Score | | |
| GI Subspecialist Pathologist's Dx (LGD vs. | 2.12 (0.94-4.79) | 0.07 |
| Continuous Risk Score | 1.59 (1.35-1.89) | <0.0001 |

Multivariate Cox models were run in which progression to HGD/EAC was evaluated first in relation to clinical variables alone, then in relation to Risk Score as a continuous variable and clinical variables in non-progressor patients and incident progressor patients. The following clinical variables were dichotomized: pathologist diagnosis (LGD vs ND or IND), sex (0 for F, 1 for M), BE segment length (0 for short (≤3 cm), 1 for long (>3 cm). Age, p53 and Risk Score were evaluated as continuous variables.
*n = 35 incident progressor patients and n = 116 non-progressor patients with complete data for all evaluated variables.
**n = 41 incident progressor patients and n = 142 non-progressor patients (all training set patients) for analysis in part B.

Figure 4A:
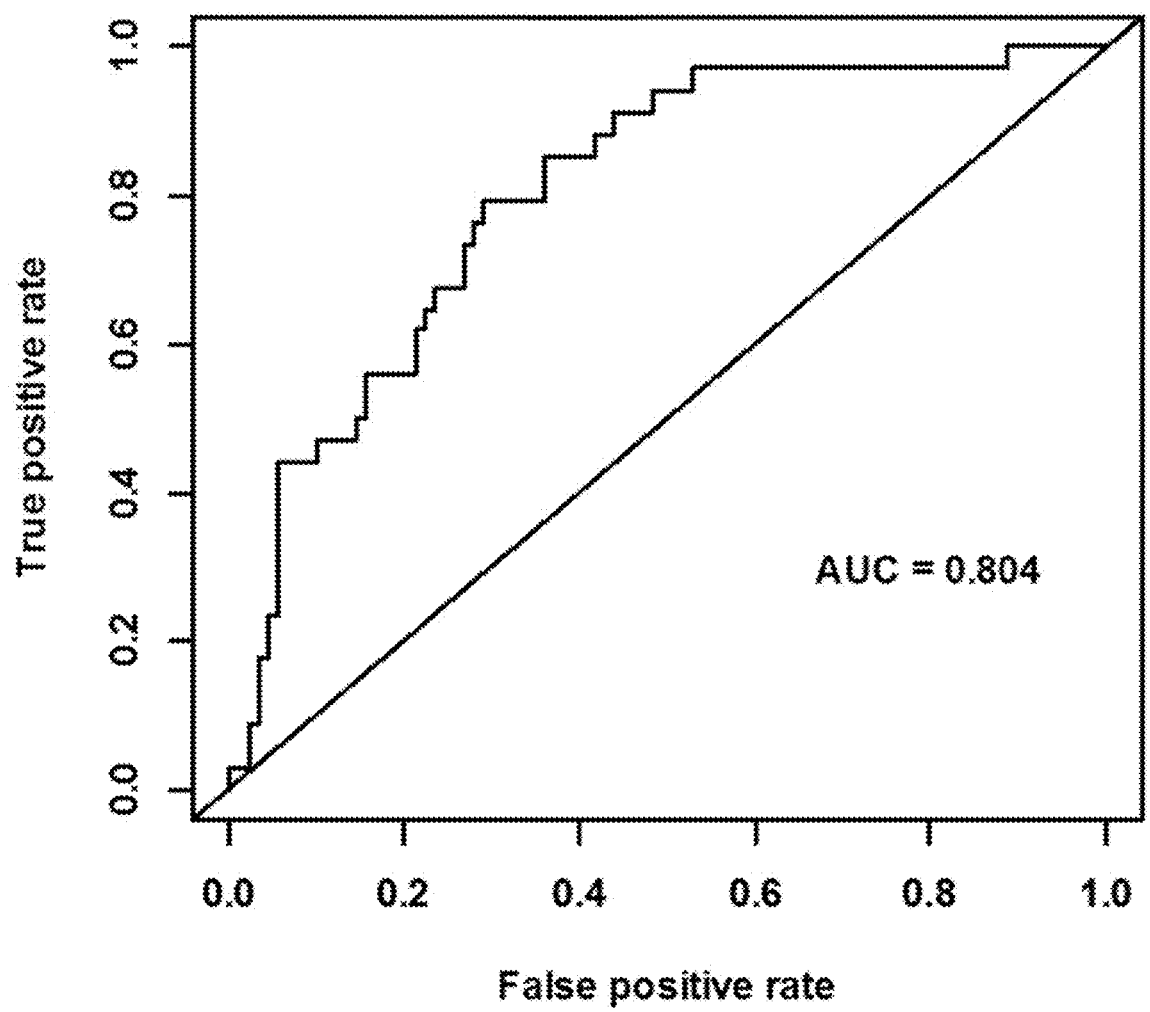
Figure 4B:
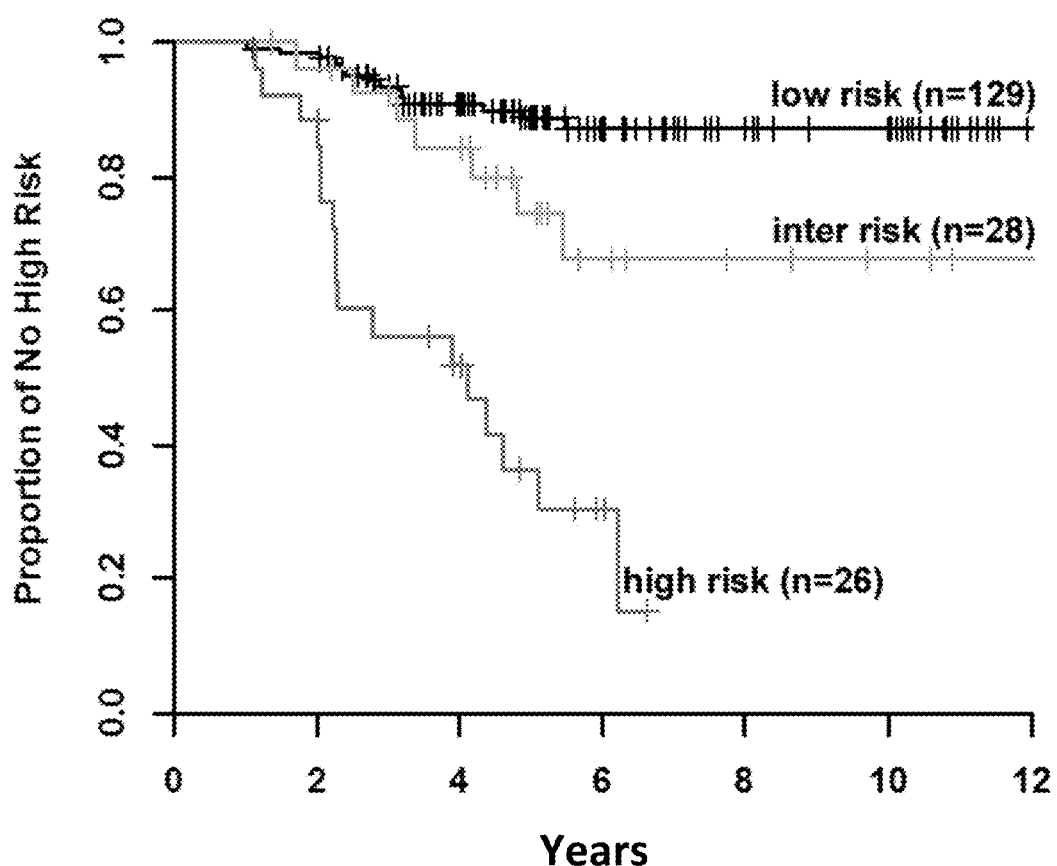
Figure 4C:
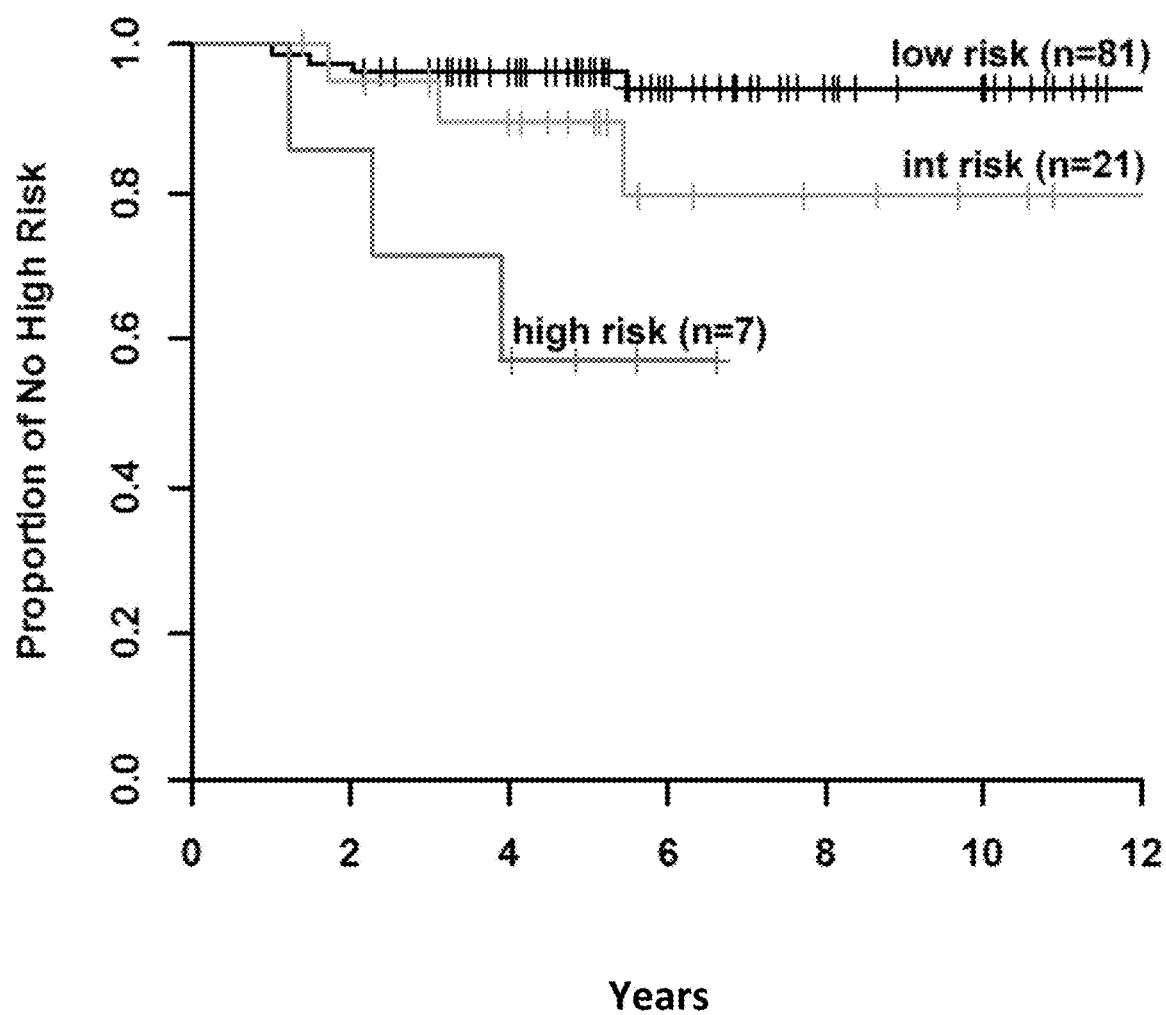
Figure 4D:
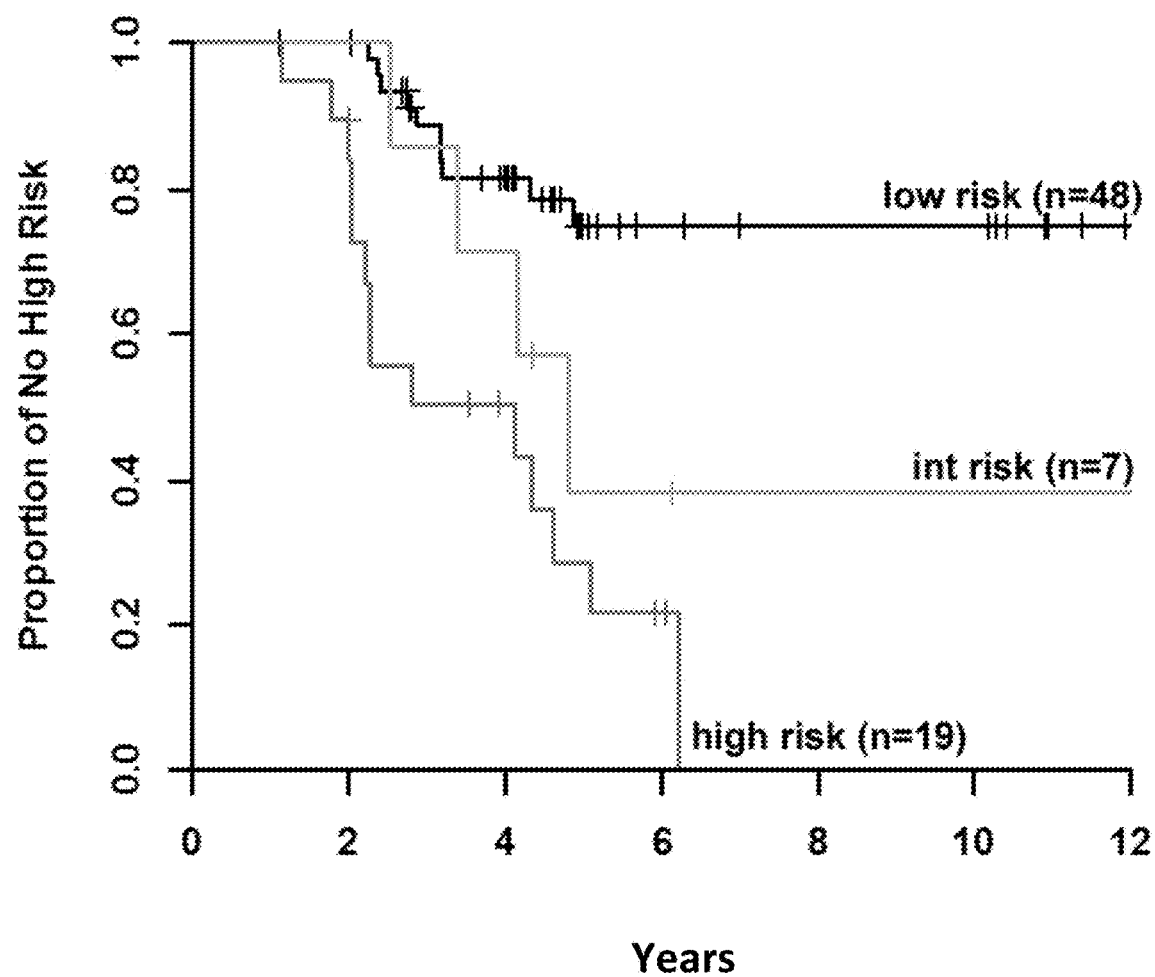
Figure 4F:
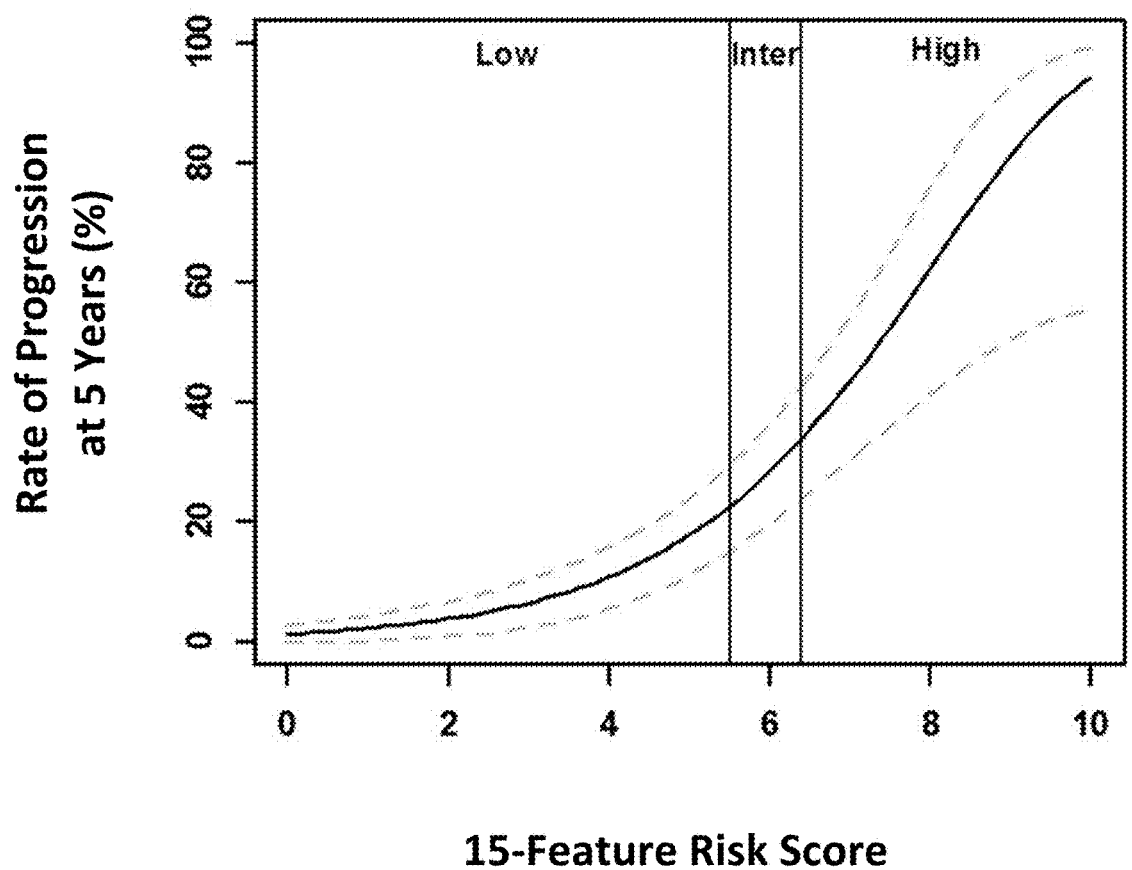

Performance of 15-Feature Classifier in the Independent Validation Set: The prospectively defined test was then evaluated in the independent validation set of BE patients (Table 3). ROC analysis showed that the pre-specified test predicted 5-year risk of progression to HGD/EAC with AUROCs of 0.804 in patients from all four institutions (FIG. 4A), 0.860 in US patients and 0.717 in AMC patients. KM analysis demonstrated that the 15-feature classifier could distinguish incident progressors from non-progressors in the full validation set of patients and in US and AMC patients separately (FIG. 4B-FIG. 4D), independently validating the performance of the 15-feature classifier that was observed in the training set. HRs were 2.45 (95% C.I. 0.99, 6.07) for the comparison of the intermediate-risk versus low-risk group and 9.42 (95% C.I. 4.61, 19.24) (FIG. 4E), for high-risk versus low-risk group (p<0.0001 for both log-rank and score tests). The probability of progression to HGD/EAC by 5 years increased continuously as the 15-feature risk score increased (FIG. 4F). Prevalence-adjusted NPV and PPV based on 5-year progression to HGD/EAC for the 15-feature classifier in the validation set were 0.98 and 0.26 using previously reported progression rates. The prevalence-adjusted proportions of patients scored low-, intermediate- and high-risk by the test were 77%, 15% and 8%, respectively.

Multivariate Cox models evaluating a reduced model with clinical variables only and a full model with the 15-feature classifier added in the validation set showed that the high-risk class provided prognostic power that was independent of the general and GI subspecialist pathologist's diagnosis, segment length, age, gender and percentage of cells overexpressing p53 (Table 8A). Although the hazard ratios suggest an association of the p53 variable with progression risk, the p-values for the p53 variable in the Cox regressions (both without and with the risk prediction test) were not statistically significant, indicating that the effect of the p53 variable cannot be distinguished from random chance regardless of the value of the hazard ratios. The GI subspecialist diagnosis showed prognostic power when evaluated alone; however, it was no longer statistically significant when the predicted risk classes were added to the Cox model (Table 8B). Similar results were observed when the risk score was evaluated as a continuous variable (Table 9).

TABLE 8

Prognostic Performance of Risk Classes vs. Clinical Variables in Independent Validation Set of BE Patients

| Variable | Hazard Ratio (95% CI) | P Value |
|---|---|---|
| A. Prognostic Performance of Risk Classes vs. Clinical Variables* | | |
| Analysis without Risk Prediction Test | | |
| General Pathologist's Dx (LGD vs. ND/IND) | 1.55 (0.67-3.58) | 0.31 |
| Segment length (Long vs. Short) | 2.53 (1.00-6.42) | 0.05 |
| Age | 0.99 (0.96-1.02) | 0.38 |
| Gender | 1.47 (0.51-4.29) | 0.48 |
| p53 (% cells overexpressing)‡ | 6.87 (0.01-4755.13) | 0.56 |
| Analysis with Risk Prediction Test | | |
| General Pathologist's Dx (LGD vs. ND/IND) | 1.27 (0.53-3.01) | 0.59 |
| Segment length (Long vs. Short) | 1.91 (0.75-4.87) | 0.17 |
| Age | 0.99 (0.96-1.02) | 0.4 |
| Gender | 1.01 (0.34-3.05) | 0.98 |
| p53 (% cells overexpressing) | 0.6 (0-728.87) | 0.89 |
| Risk Classes (predicted by the test) | | |
| Intermediate vs. Low Risk | 2.11 (0.66-6.7) | 0.21 |
| High vs. Low Risk | 7.27 (3.2-16.49) | <0.0001 |
| B. Prognostic Performance of Risk Classes vs. GI Subspecialist** | | |
| Analysis without Risk Prediction Test | | |
| GI Subspecialist Pathologist's Dx (LGD vs. | 3.19 (1.24-8.2) | 0.02 |
| Analysis with Risk Prediction Test | | |
| GI Subspecialist Pathologist's Dx (LGD vs. | 1.33 (0.5-3.53) | 0.57 |
| Risk Classes (predicted by the test) | | |
| Intermediate vs. Low Risk | 2.37 (0.95-5.93) | 0.07 |
| High vs. Low Risk | 8.95 (4.27-18.77) | <0.0001 |

Multivariate Cox models were run in which progression to HGD/EAC was evaluated first in relation to clinical variables alone, then in relation to risk classes and clinical variables in non-progressor patients and incident progressor patients in the validation set. Pathologist diagnosis, gender, segment length, and Risk Classes were dichotomized as described in Methods. Age and p53 were evaluated as continuous variables. Mann-Whitney tests showed no statistically significant difference between age, gender or segment length in progressors versus non-progressors (p = 0.72, 0.36, 0.09, respectively).
*n = 30 incident progressor patients and n = 103 non-progressor patients with complete data for all evaluated variables.
**n = 38 incident progressor patients and n = 145 non-progressor patients (all validation set patients) for analysis in part B.
‡ calculated by the image analysis software.

TABLE 9

Comparison of Predictive Performance of Risk Score as a Continuous Variable vs. Clinical Variables in Validation Set

| Variable | Hazard Ratio (95% CI) | P Value |
|---|---|---|
| A. Multivariate Cox Analysis of Risk Score vs. Clinical Variables* | | |
| Analysis without Risk Score | | |
| General Pathologist's Dx (LGD vs. ND/IND) | 1.55 (0.67-3.58) | 0.31 |
| Barrett's segment length (Long vs. Short) | 2.53 (1-6.42) | 0.05 |
| Age | 0.99 (0.96-1.02) | 0.38 |
| Gender | 1.47 (0.51-4.29) | 0.48 |
| p53 (% cells overexpressing) | 6.87 (0.01-4755.13) | 0.56 |
| Analysis with Risk Score | | |
| General Pathologist's Dx (LGD vs. ND/IND) | 1.41 (0.6-3.33) | 0.44 |
| Barrett's segment length (Long vs. Short) | 1.86 (0.73-4.73) | 0.19 |
| Age | 1 (0.97-1.03) | 0.94 |
| Gender | 0.9 (0.3-2.73) | 0.86 |
| p53 (% cells overexpressing) | 0.05 (0-83.69) | 0.42 |
| Continuous Risk Score | 1.65 (1.35-2.03) | <0.0001 |
| B. Multivariate Cox Analysis of Risk Score vs GI Subspecialist** | | |
| Analysis without Risk Score | | |
| GI Subspecialist Pathologist's Dx (LGD vs. | 3.19 (1.24-8.2) | 0.02 |
| Analysis with Risk Score | | |
| GI Subspecialist Pathologist's Dx (LGD vs. | 1.35 (0.5-3.64) | 0.55 |
| Continuous Risk Score | 1.71 (1.44-2.04) | <0.0001 |

Multivariate Cox models were run in which progression to HGD/EAC was evaluated first in relation to clinical variables alone, then in relation to Risk Score and clinical variables in non-progressor patients and incident progressor patients. The following clinical variables were dichotomized: pathologist diagnosis (LGD vs. ND or IND), gender (0 for F, 1 for M), BE segment length (0 for short (≤3 cm), 1 for long (>3 cm) and Risk Score. Age, p53 and Risk Score were evaluated as continuous variables.
*n = 30 incident progressor patients and n = 103 non-progressor patients with complete data for all evaluated variables.
**n = 38 incident progressor patients and n = 145 non-progressor patients (all validation set patients) for analysis in part B.

Discussion: Using a nested case-control study design we have developed and independently validated a novel multi-variable test that predicts future risk of progression to HGD/EAC in BE patients. The test produces a risk score that can be used as a continuous predictor to estimate 5-year risk for progression to HGD/EAC. The test incorporates 3-tier risk stratification to classify patients as low-, intermediate- or high-risk for progression. There was a large difference in the progression rate between patients with low-risk scores and those with high-risk scores. The predicted high-risk group of patients was at 9.4-fold increased risk of developing HGD/EAC compared to the low-risk group. Furthermore, the risk classes provided independent predictive information that outperformed traditional risk factors, including the original general pathologist diagnosis and also the expert GI pathologist diagnosis. Multivariate Cox analyses showed that male gender and segment length did not provide prognostic power. However, the case-controls were matched based on gender and where possible segment length. Importantly, the test demonstrated risk stratification that was independent of traditional clinical variables in an independent cohort of BE patients.

The tissue systems pathology approach developed and validated in this study has the potential to provide pathologists with information that complements histologic analysis and provide gastroenterologists, other providers and patients with an individualized risk score to guide decision-making on surveillance frequency and therapies. The 3-tier classifier identifies patients at very low risk of progressing to HGD/EAC within 5 years. If further validated, this finding suggests that the frequency of endoscopic surveillance in this group of patients can potentially be extended to 5 years. The classifier also identifies patients at very high risk of progression. Current clinical guidelines recommend intervention with endoscopic ablative therapy for confirmed HGD and there is growing evidence to support ablative therapy for confirmed LGD. The patients identified as high-risk by the classifier included patients with LGD, IND and ND confirmed by an expert GI pathologist. The independent validation of this risk prediction approach provides potential support to extend ablative therapy to BE patients with IND and ND by objectively identifying multiple molecular and cellular changes indicative of future progression. Standard pathology is qualitative and prone to inter-observer variation, even among GI subspecialists. The approach described here is quantitative, objective and outperformed both the generalist diagnosis and GI subspecialist diagnosis. While the testing approach described here would initially add cost to the surveillance of patients with BE, there is the compensatory potential to lower future healthcare costs due to reduced frequency of endoscopic surveillance in low-risk patients, and early endoscopic treatment to prevent malignant progression in high-risk patients.

The limitations of this study include the retrospective nature of the cohort, which can result in selection bias and the limited sample size. However, a larger prospective study would not have been feasible for the training and initial validation of the risk classifier due to the very low prevalence of disease progression in BE. The study lacked central pathology review, although all cases were reviewed by a single GI subspecialist pathologist at each of the US institutions. The retrospective cohort included patients in surveillance at multiple centers, which prevented standardization of biopsy fixation and storage protocols. However, the biopsies were all collected during endoscopic surveillance, and thus reflect routine BE samples requiring risk assessment. While digital pathology has gained traction in recent years, the use of imaging and image analysis in anatomic pathology laboratories remains limited. The approach described here could be deployed in a central reference clinical laboratory capable of anatomic pathology services and equipped with the necessary imaging instrumentation, the image analysis software, and technical staff skilled in digital pathology.

Many biomarkers have shown promise for risk prediction in BE, including biomarkers such as p53 and AMACR that were evaluated in this study. Despite extensive efforts no biomarkers for risk prediction have been validated or translated into clinical practice to date. The challenges to risk prediction include genetic and non-genetic heterogeneity in tissues and the resulting need to assess multiple pathways of carcinogenesis. The role of epithelial and stromal components in carcinogenesis suggest that a systems biology approach to anatomic pathology may overcome prior study limitations. Although biomarkers such as p53 have shown promise in risk prediction, not all patients have detectable p53 abnormalities at the pre-progression stage and a subset of non-progressor patients also exhibit p53 abnormalities. While p53 IHC is recommended by the BSG as a diagnostic aid, it is not sufficient as a single biomarker for risk prediction. The methods used to detect and score biomarkers have also hindered implementation. Traditional pathology methods have limited utility in the evaluation of multiple biomarkers due to the difficulties in managing multiple IHC tests on limited BE biopsies, observer variation and the challenges of manually integrating morphologic and biomarker data into a prognosis. The test that was developed and validated in this study represents a considerable improvement over clinical variables and individual biomarkers assessed by IHC to provide individualized risk prediction. This testing approach aids pathology by objectively measuring multiple molecular and cellular abnormalities that can precede the epithelial morphologic changes assessed by pathologists. The risk score validated in this study identifies high-risk BE patients as having loss of tumor suppression, loss of cell cycle control, stromal angiogenesis, altered patterns of infiltrating immune cells, increased inflammation and morphology abnormalities, which are early indicators of progression. The classifier utilizes multiple image analysis features extracted from the same biomarker to capture different expression patterns (Table 5). For example, p53 is frequently mutated in BE and while some mutations lead to p53 protein accumulation, others lead to p53 protein loss. By assessing mean and sum intensities and also intensities in nuclei clusters extracted by image analysis software, the multivariable classifier aims to quantify multiple patterns of p53 abnormalities in a standardized, objective manner. The multivariable classifier also incorporates microenvironment-based image analysis features that capture localized abnormalities such as focal AMACR overexpression and clusters of HIF-1α-overexpressing cells. Gene expression profiling, DNA sequencing approaches and molecular approaches to assess mutations and DNA methylation have also been applied to diagnostic and prognostic testing in BE. While these technologies have aided biomarker discovery and show promise in risk prediction, they have the disadvantage of requiring tissues to be digested, resulting in loss of morphology and spatial relationships between biomarkers, which may be relevant to patient outcomes. Furthermore, specific tests using these genomic technologies have not been independently validated in BE.

In addition to the advantages of the tissue systems testing technology platform, this study was strengthened by the use of a diverse patient cohort from four high-volume institutions. An additional strength of the cohort was the exclusion of patients with prevalent HGD/EAC, enabling development of a test that predicts incident progression. Furthermore, the test was validated on an independent set of BE patients. The assay can be performed on sections from FFPE blocks that are taken for routine endoscopic surveillance.

In summary, the tissue systems pathology approach validated in this study quantifies multiple epithelial and stromal processes and better predicts risk of progression to HGD/EAC in BE patients than clinical variables, including pathologic diagnosis. This tissue systems pathology approach provides opportunity to improve upon current qualitative histology as a quantitative method to risk stratify BE into high-risk patients who may benefit from treatment and low-risk patients in whom surveillance intervals can be extended.

Example 2

Background: There is a need for improved tools to detect prevalent high grade dysplasia (HGD) and esophageal adenocarcinoma (EAC) in patients in endoscopic surveillance programs for Barrett's esophagus (BE).

Aims: In a previous study a multivariable classifier, based on a tissue analysis approach that detects multiple molecular and cellular changes in pre-progression BE biopsies, was developed to predict future risk of progression in BE. This study aimed to determine whether the multivariable classifier could detect a field effect associated with prevalent HGD and EAC in biopsies with diagnoses of non-dysplastic intestinal metaplasia (ND), indefinite for dysplasia (IND) or low-grade dysplasia (LGD) from patients with BE.

Methods: A nested case-control study was conducted to develop and validate a classifier to risk stratify patients with BE based upon an imaging platform that quantifies multiple epithelial, stromal and morphometric variables in BE biopsies. Data were collected from a multi-center cohort of patients in endoscopic surveillance programs at 4 institutions in the United States or Europe. In a prior study a multivariable classifier was developed in a training set of pre-progression ND, IND and LGD BE biopsies from patients who progressed to HGD/EAC in ≥1 year (n=41) and baseline biopsies from matched non-progressor controls (n=142). Biopsy sections were fluorescently-immunolabeled for a panel of 14 epithelial and stromal biomarkers, imaged and analyzed by image analysis software to extract quantitative biomarker and morphometric features. A 3-tier classifier based on 15 quantitative features derived from 9 biomarkers and morphology was selected in the training set. In the study presented here the selected 3-tier classifier was evaluated in an independent validation set of BE biopsies with diagnoses of ND, IND or LGD from patients who had a diagnosis of HGD or EAC in <1 year (prevalent cases, n=30) and matched non-progressor controls (n=145).

Figure 6A:
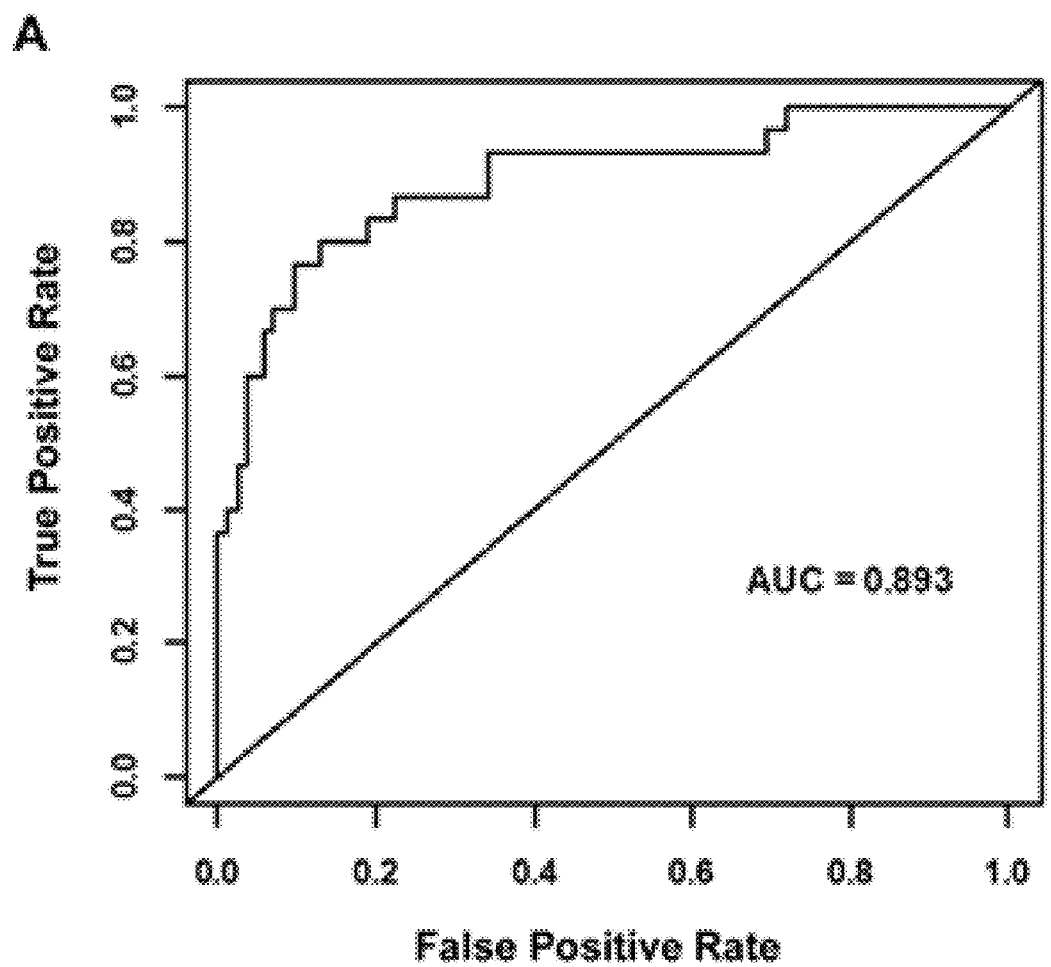
Figure 6B:
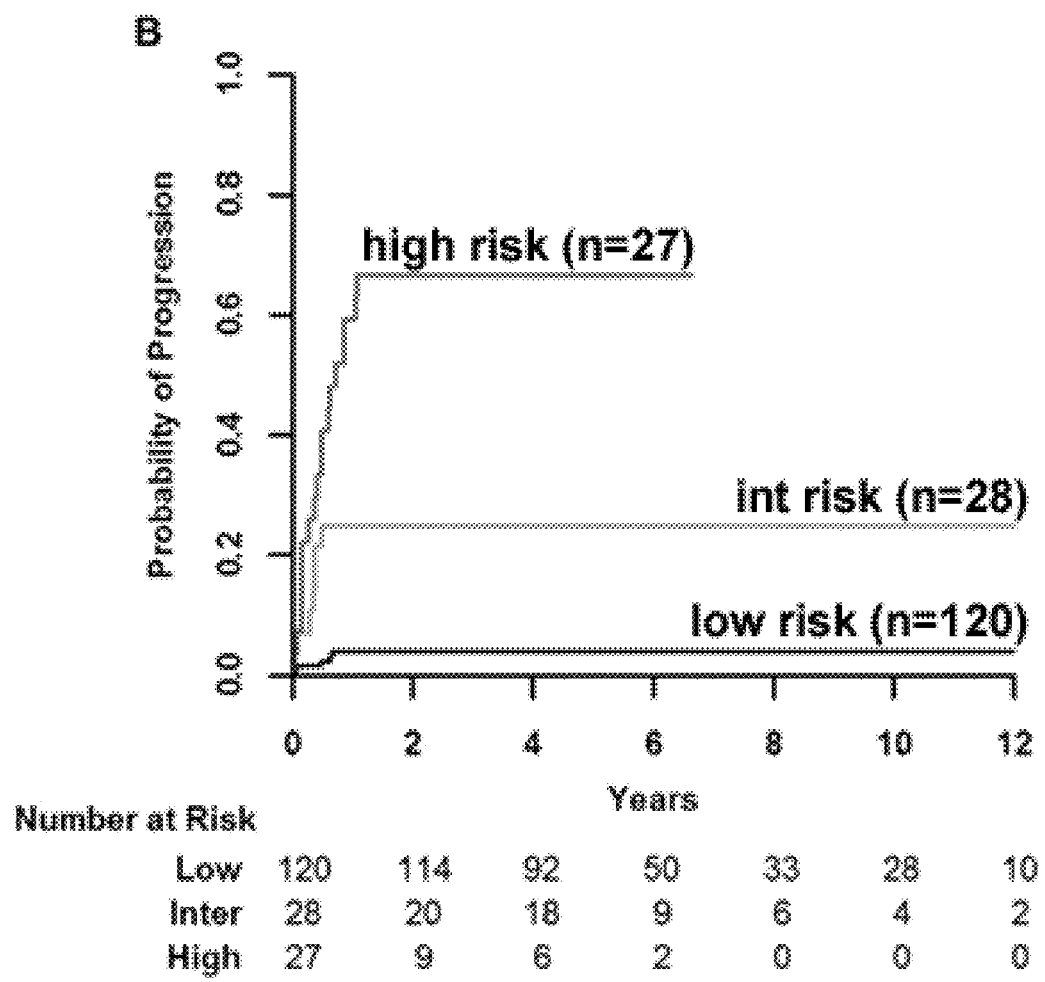

Results: The classifier detected multiple molecular and cellular changes in ND, IND and LGD BE biopsies from patients with prevalent HGD or EAC. The 3-tier classifier stratified patients into low-, intermediate- and high-risk classes in the independent validation set of prevalent cases and non-progressors (hazard ratio 23.18; 95% confidence interval 8.57-62.73 for high-risk vs low-risk BE, p<0.0001 (FIG. 6)). The risk classes predicted by the classifier also provided independent prognostic information that outperformed the pathologic diagnosis provided by generalist and gastrointestinal subspecialist pathologists (Table 10).

TABLE 10

Performance of Risk Classes Predicted by Test vs. Pathologic Diagnosis in Stratifying BE Patients with Prevalent HGD/EAC from Non-Progressor BE Patients.

| Variable | Hazard Ratio (95% CI) | P Value |
|---|---|---|
| A. Predictive Performance of Risk Classes vs. Generalist Pathologist Diagnosis | | |
| Analysis without Risk Prediction Test | | |
| General Pathologist's Dx (LGD vs. ND/IND) | 9.65 (3.39-27.47) | <0.0001 |
| Analysis with Risk Prediction Test | | |
| General Pathologist's Dx (LGD vs. ND/IND) | 3.47 (1.15-10.48) | 0.03 |
| Risk Classes (predicted by the test) | | |
| Intermediate vs. Low Risk | 9.99 (1.84-54.2) | 0.01 |
| High vs. Low Risk | 21.25 (4.26-105.86) | 0.0002 |
| B. Predictive Performance of Risk Classes vs. GI Subspecialist Pathologist Diagnosis | | |
| Analysis without Risk Prediction Test | | |
| GI Subspecialist Pathologist's Dx (LGD vs. | 12.95 (6.24-26.89) | <0.0001 |

TABLE 10-continued

Performance of Risk Classes Predicted by Test vs. Pathologic Diagnosis in Stratifying BE Patients with Prevalent HGD/EAC from Non-Progressor BE Patients.

| Variable | Hazard Ratio (95% CI) | P Value |
| --- | --- | --- |
| Analysis with Risk Prediction Test | | |
| GI Subspecialist Pathologist's Dx (LGD vs. Risk Classes (predicted by the test) | 3.87 (1.71-8.77) | 0.001 |
| Intermediate vs. Low Risk | 5.37 (1.66-17.4) | 0.01 |
| High vs. Low Risk | 12.46 (4.11-37.76) | <0.0001 |

Multivariate Cox models were run in which subsequent diagnosis of HGD/EAC was evaluated first in relation to pathologic diagnosis alone, then in relation to risk classes and pathologic diagnosis in non-progressor patients and patients with prevalent HGD/EAC in the validation set. Variables were dichotomized as follows; diagnosis: LGD vs. ND and IND combined, risk classes predicted by the test: intermediate vs. low risk class and high vs. low risk class.

Conclusions: A tissue systems pathology test better predicts presence of prevalent HGD and EAC in BE than clinicopathologic variables, and has the potential to improve upon histology as an objective diagnostic method to identify patients requiring therapeutic intervention. The results indicate that the molecular and cellular changes associated with malignant transformation in BE may extend beyond areas with definitive HGD or EAC and may be detectable as a field effect by the tissue systems pathology test.

Example 3

Background: There is a need for improved tools to detect high grade dysplasia (HGD) and esophageal adenocarcinoma (EAC) in patients with Barrett's esophagus (BE). In previous work, we demonstrated that a 3-tier classifier predicted risk of incident progression in BE. Our aim was to determine if this risk classifier could detect a field effect in non-dysplastic (ND), indefinite for dysplasia (IND) or low-grade dysplasia (LGD) biopsies from BE patients with prevalent HGD/EAC.

Methods: We performed a multi-institutional case-control study to evaluate a previously developed risk classifier that is based upon quantitative image features derived from 9 biomarkers and morphology, and predicts risk for HGD/EAC in BE patients. The risk classifier was evaluated in ND, IND and LGD biopsies from BE patients diagnosed with HGD/EAC on repeat endoscopy (prevalent cases, n=30, median time to HGD/EAC diagnosis 140.5 days) and non-progressors (controls, n=145, median HGD/EAC-free surveillance time 2,015 days).

Results: The risk classifier stratified prevalent cases and non-progressor patients into low-, intermediate- and high-risk classes (odds ratio, 46.0; 95% confidence interval, 14.86-169 (high-risk vs low-risk); p<0.0001). The classifier also provided independent prognostic information that outperformed the subspecialist and generalist diagnosis.

Conclusion: A tissue systems pathology test better predicts prevalent HGD/EAC in BE patients than pathologic variables. The results indicate that molecular and cellular changes associated with malignant transformation in BE can be detected as a field effect using the test.

Introduction: Barrett's esophagus (BE) is a precursor to esophageal adenocarcinoma (EAC), which is the fastest growing cancer type by incidence in the US with 5 year survival rates of 18%. EAC can be prevented if dysplasia is detected and treated early with endoscopic therapies such as radiofrequency ablation (RFA) and/or endoscopic mucosal resection (EMR). Current guidelines from the American College of Gastroenterology (ACG) recommend surveillance by endoscopy with biopsies at intervals determined by the pathologic diagnosis. The diagnosis of dysplasia in BE is limited by the random nature of endoscopic sampling, which may miss dysplastic areas, and by inter-observer variation. While subtle lesions containing high grade dysplasia (HGD) and EAC can be detected by expert endoscopists at high-volume centers, recognition of subtle lesions is more challenging in the community setting. These limitations can result in repeat endoscopies and delayed diagnoses of HGD and EAC.

A field effect has been described in many different cancer types, including in EAC. Dysplasia and EAC can be multifocal in BE. The same mutations and aberrant DNA methylation have been found at multiple levels and in large fields in BE, indicating field cancerization. A preneoplastic field surrounding HGD or EAC may appear histologically non-dysplastic (ND) or low grade dysplasia (LGD) but exhibit molecular and cellular changes associated with malignant transformation. Detection of abnormalities in this expanded field may overcome the limitations of random sampling and subjective diagnoses, enabling earlier diagnosis of HGD and EAC.

Figure 7:
FIG. 7 illustrates a 15-Feature 3-Tier Risk Classifier Process and the risk score (0-10) and class (low, intermediate or high) are calculated from the scaled and coefficient-weighted sum of 15 quantitative image analysis measurements (features) derived from 9 protein-based biomarkers and morphology as follows: 1) Multiplexed Immunofluorescence Slide Labeling—Serial sections of FFPE BE biopsies are fluorescently immunolabeled for p16, AMACR, p53, HER2, K20, CD68, COX-2, HIF-1α, and CD45RO, plus Hoechst; 2) Whole Slide Fluorescence Scanning—Labeled slides are imaged by whole slide fluorescence scanning that generates image data on each biomarker and nuclei; 3) Automated Image Analysis: Tissue images are analyzed by automated image analysis software to extract 15 features from the 9 protein-based biomarkers and Hoechst; 4) Risk Classification: The 15 features are scaled using center and scale parameters defined in a training study, then weighted by coefficients derived from univariate Cox regression analysis of the features and progression outcomes in the training study as described herein.
Figure 7:
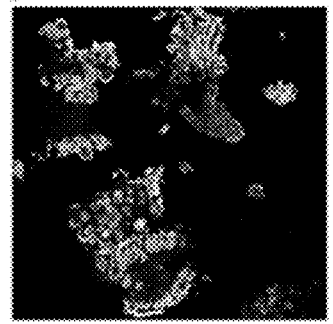
Figure 7:
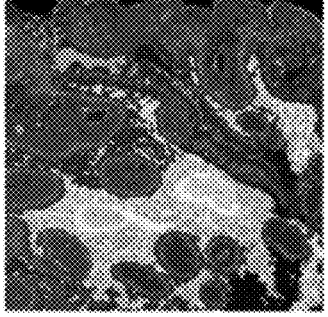

Many biomarkers have been evaluated in BE and the British Society of Gastroenterology (BSG) recommends p53 immunohistochemistry (IHC) to aid diagnosis of dysplasia. However, no biomarkers have been validated to reliably detect the field effect or abnormalities associated with prevalent dysplasia and EAC in BE. A tissue systems pathology approach based upon an imaging platform that quantifies both epithelial and stromal abnormalities has been shown to aid in distinguishing HGD from non-dysplastic BE with reactive atypia. This imaging approach has also been demonstrated to predict incident progression in BE, by objectively quantifying molecular and cellular features that precede definitive morphologic changes (FIG. 7). The assay employs multiplexed immunofluorescence labeling of 9 epithelial and stromal biomarkers in sections from formalin-fixed paraffin-embedded (FFPE) biopsies. The fluorescently-labeled slides are imaged by whole slide fluorescence scanning, and automated image analysis software extracts quantitative expression and localization data on the biomarkers and morphology. The final step utilizes a multivariable classifier to integrate the quantitative image analysis data into individualized scores that are correlated with risk of HGD/EAC (FIG. 7). This may have applications in detecting molecular and cellular changes in the expanded preneoplastic field associated with HGD/EAC. The aim of this study was to determine whether this assay can detect abnormalities indicative of a field effect in ND, indefinite for dysplasia (IND) and LGD biopsies from BE patients with prevalent HGD/EAC.

Materials and Methods

Study Design and Patients: A case-control study was constructed that utilized a multi-center cohort of BE patients with clinical outcome data from four high volume institutions (Geisinger Health System, University of Pittsburgh, University of Pennsylvania and Academic Medical Center (AMC), Amsterdam, Netherlands). BE cases with ND, IND or LGD confirmed by a gastrointestinal (GI) subspecialist pathologist (J. M. D., J. L., N. C. J.) were retrieved. For patients with multiple biopsy levels taken at the same endoscopy, the biopsy with the highest diagnosis determined by a GI subspecialist pathologist was selected (LGD was the highest diagnosis, then IND, and ND was the lowest). For patients with multiple biopsy levels with the same diagnosis, the pathologist at each institution selected a representative block with sufficient tissue for analysis. Inclusion criteria were availability of tissue blocks and clinicopathologic data, and confirmation of intestinal metaplasia by a GI subspecialist. Exclusion criteria were insufficient tissue quality (assessed by a pathologist), and use of Bouin's fixative or methylene blue in sample processing that can interfere with fluorescence immunolabeling. Cases were patients who had HGD/EAC on repeat endoscopy in <1 year (n=23) or had prior history of treated HGD/EAC, returned to ND, IND or LGD and had HGD/EAC on repeat endoscopy (n=7) (prevalent cases, n=30 in total). Prevalent cases with and without a prior history as described above were included since both subsets of patients can harbor HGD or early EAC that can be challenging to recognize during endoscopy. The non-progressor controls did not show HGD/EAC on repeat endoscopy and had median HGD/EAC-free surveillance time of 5.6 years (n=145). Data elements collected were: case collection date, original pathologic diagnosis and GI subspecialist diagnosis for the case tested in this study, date and original diagnosis of every surveillance biopsy, progression endpoint (HGD/EAC), HGD/EAC-free surveillance time (time between case tested and HGD/EAC diagnosis or last follow-up), age, sex, and segment length (cm) and segment class (short ≤3 cm, long >3 cm). The study was approved by the institutional review boards at each institution.

Fluorescence Immunolabeling: 5 μm sections of FFPE BE biopsies were stained with H&E by standard histology methods. K20, p16INK4a, AMACR, p53, HER2/neu, CD68, COX-2, HIF-1α, and CD45RO were labeled by multiplexed immunofluorescence according to previously described methods. The biomarkers were multiplexed in sub-panels of 3 primary antibodies per slide detected via Alexa Fluor-488, -555 and -647-conjugated secondary antibodies and Hoechst-33342 to label DNA (Life Technologies, Carlsbad, Calif.).

Whole Slide Imaging: H&E-stained slides were imaged at 20× magnification on a NanoZoomer Digital Pathology scanner (Hamamatsu Photonics, K.K., Japan). Fluorescently-immunolabeled slides were imaged using a standard operating procedure at 20× magnification on a ScanScope FL (Leica BioSystems, Vista, Calif.) as previously described.

Image Analysis: Whole slide fluorescence images were analyzed using the TissueCypher™ Image Analysis Platform (Cernostics, Inc., Pittsburgh, Pa.), which utilizes automated tissue image analysis algorithms for segmenting cell-based objects and tissue structures (e.g. epithelial and stromal compartments) to allow contextual, quantitative biomarker and morphology feature data collection. The image analysis algorithms have been described in detail previously, which is hereby incorporated by reference in its entirety. The 15 features employed by the risk classifier (Table 2) were extracted from the fluorescence whole slide tissue images.

Statistical Analyses: A risk prediction classifier was developed in a previous study for prediction of incident progression to HGD/EAC (FIG. 7). In this study, we tested the hypothesis that the patients in the predicted high-risk class have significantly higher risk for presence of prevalent HGD/EAC than patients in the predicted low-risk class. We also tested the hypothesis that the risk classes would provide independent and stronger prognostic information beyond that of the pathologic diagnosis (GI subspecialist or generalist pathologist). Sample size calculations indicated that a total of 43 patients (including both prevalent cases and non-progressors) were required to ensure 80% power to detect a significant difference of 50% in the risk of prevalent HGD/EAC between those classified as high-risk vs low-risk, at a 0.05 significance level. All assay parameters were pre-specified, including the 15 image analysis feature/measures, scaling parameters, the classifier model and cutoffs as defined in the previous study. The risk score and risk class (low, intermediate or high) were calculated for each case.

Receiver Operating Characteristic (ROC) curves were plotted based on the binary outcome of the subsequent diagnosis of HGD/EAC (cases) versus no disease progression (control) and the continuous risk scores of the test. ROC curves were also plotted for percentage of cells overexpressing p53 (determined by the image analysis software as described previously). The comparison to p53 was done since the BSG recommends p53 IHC to aid in the diagnosis of dysplasia. Logistic regression was used to evaluate the significance of association of the predicted risk groups as the independent variable with subsequent diagnosis of prevalent HGD/EAC or not as the dependent variable. Odds ratios (ORs) with 95% C.I. measuring the strength of the association between the predicted risk groups and the subsequent diagnosis of HGD/EAC were calculated from the logistic regression.

Comparison of Classifier Performance versus Pathologic Diagnosis: Multivariate logistic regression and multivariate Cox regression were performed to compare the performance of the risk classes produced by the classifier versus the pathologic diagnosis by either generalist or GI subspecialist included as the independent variable, in predicting subsequent diagnosis of HGD/EAC included as the dependent variable. The pathologic diagnosis was dichotomized: LGD versus ND and IND combined. IND and ND cases were combined due to the limited sample size of the IND subset (2 non-progressors and 1 prevalent case had subspecialist diagnosis of IND).

Results

Patients: The case-control cohort included biopsies with diagnoses of ND (n=13), IND (n=1) or LGD (n=16) from 30 BE patients with HGD or EAC (prevalent cases, median time to HGD/EAC diagnosis 140.5 days, IQR 56, 241) and 145 samples from matched control patients with clinical outcome data showing no disease progression (ND n=138, IND n=2, LGD n=5, median HGD/EAC-free surveillance time 2,015 days, IQR 1,498, 3,111). 22/30 prevalent cases were diagnosed with HGD and 8/30 were diagnosed with EAC on repeat endoscopy (Table 11). The control patients were from a cohort evaluated in a previous study, whereas the prevalent cases had not previously been evaluated. The majority of the patients were male, and a higher proportion of patients with HGD/EAC were male (93.3%) and had long segment BE (63.3%) compared to the non-progressors (78.6% were male, 50.3% had long segment), which is consistent with published epidemiology studies in EAC. The clinical characteristics of the patients are summarized in Table 11.

Figure 8A:
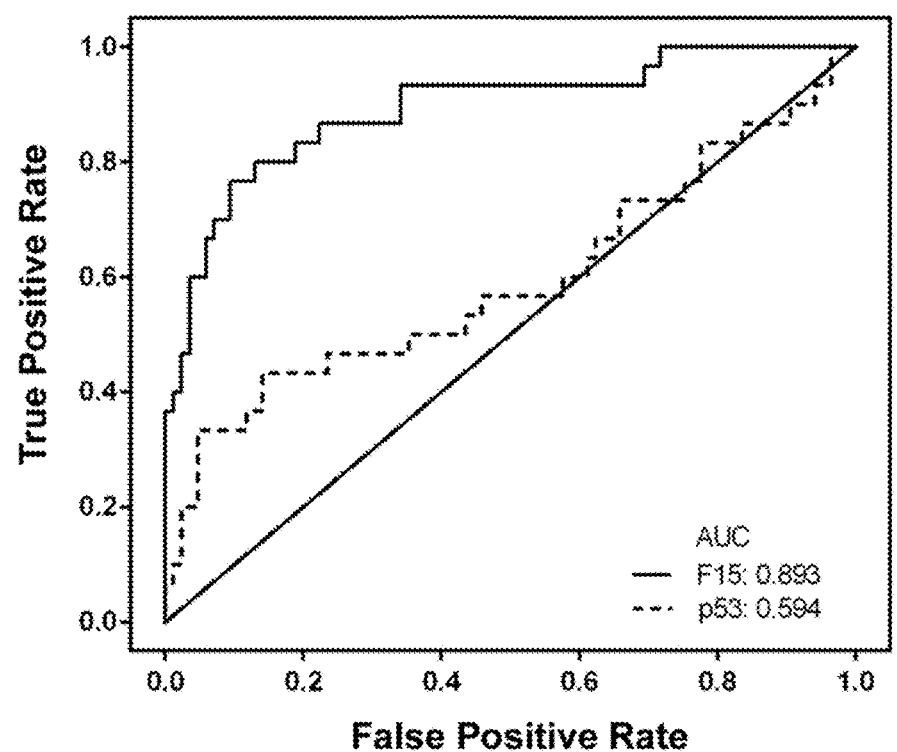
Figure 8B:
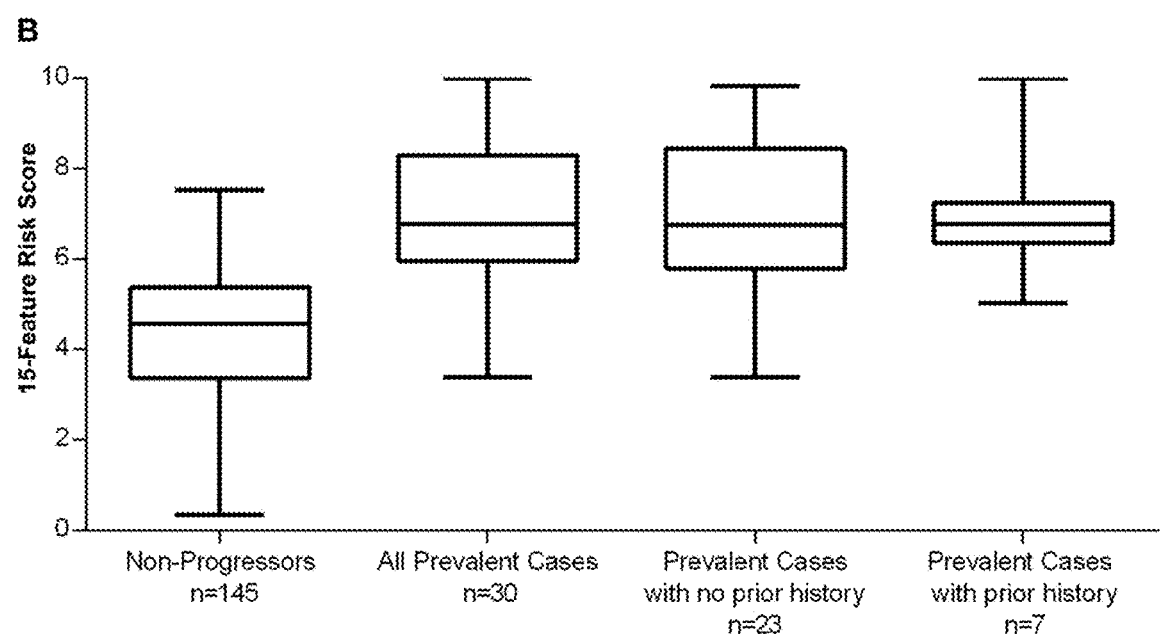
Figure 8E:
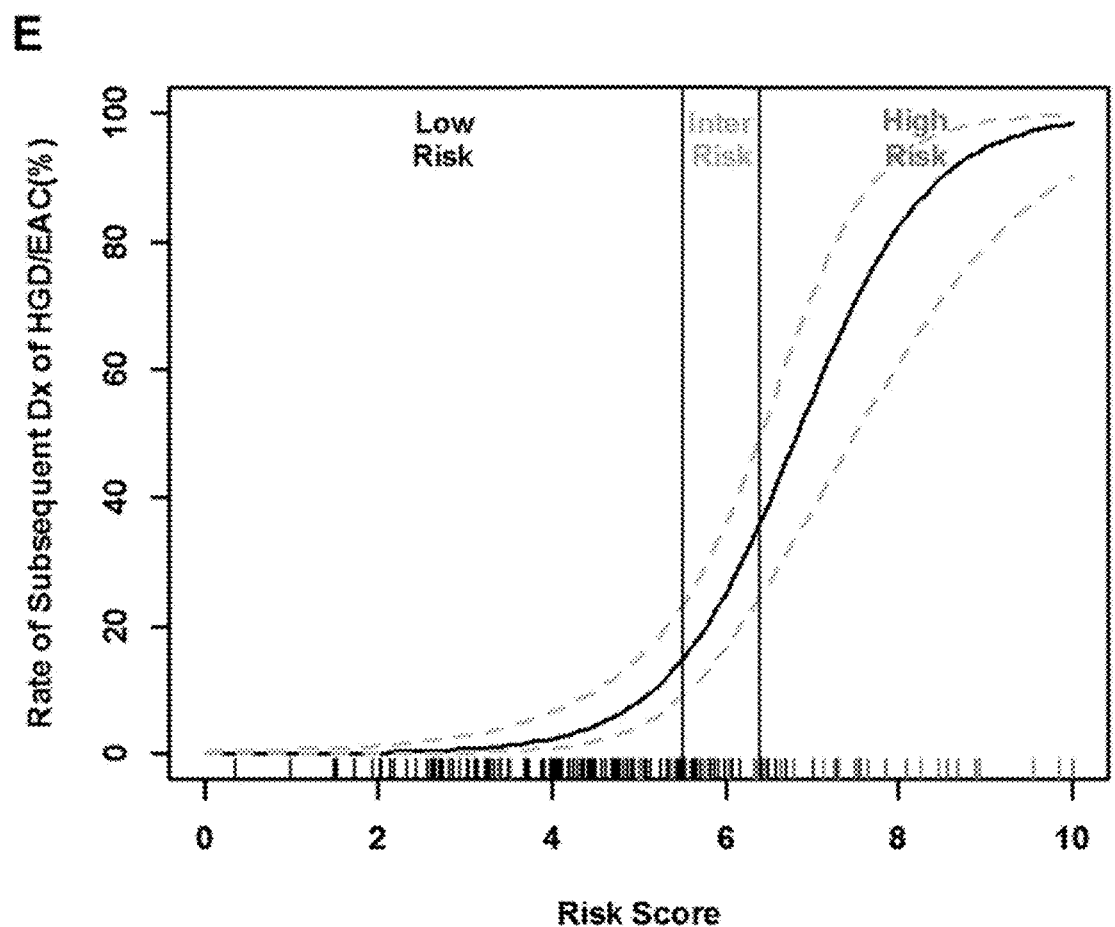

Performance of 15-Feature Risk Classifier in Stratifying Prevalent Cases from Non-Progressor Patients: The pre-specified 15-feature risk classifier was evaluated in the set of BE biopsies from prevalent cases and non-progressor patients. ROC analysis based on the binary outcome (subsequent diagnosis of HGD/EAC versus no disease progression) and the continuous risk scores showed that the classifier had the capability to distinguish prevalent HGD/EAC from non-progressors with AUROC of 0.893, whereas the % cells overexpressing p53 had AUROC 0.594 (FIG. 8A). Sub-analyses were performed on the subsets of prevalent cases with and without a prior history of HGD or EAC, since cases with a prior history of HGD/EAC may harbor greater numbers of mutations and other abnormalities than cases with no prior history. ROC analysis of the subsets of prevalent cases with and without a prior history of HGD or EAC (n=7 and 23, respectively) showed that the classifier had strong predictive performance in distinguishing both subsets from non-progressors (AUROC=0.926 and 0.883, respectively). AUROC for the ND/IND and LGD subclasses were 0.873 and 0.792, respectively. A box and whisker plot showed higher 15-feature risk scores in the prevalent cases versus non-progressors (p<0.0001, FIG. 8B). Logistic regression demonstrated that the 15-feature classifier could stratify patients with significantly different risks for prevalent HGD/EAC; ORs were 46.0 (95% C.I. 14.86-169, p<0.0001) for the comparison of the high-risk versus low-risk group and 7.67 (95% C.I. 2.24-28.14, p=0.001) for intermediate-risk versus low-risk group (FIG. 8C). The classifier identified both non-dysplastic and LGD biopsies from prevalent cases as high-risk (FIG. 8D). The probability of diagnosis of HGD/EAC on repeat endoscopy increased continuously as the 15-feature risk score increased (FIG. 8E). In multivariate logistic regression in which subsequent diagnosis of HGD/EAC was evaluated first in relation to pathologic diagnosis alone, then in relation to the predicted risk classes added to the pathologic diagnosis, the magnitude of ORs indicated that the predicted high-risk class provided independent and stronger predictive power than the generalist or GI subspecialist pathologic diagnosis in this cohort of patients (Table 12). Similar results were obtained with multivariate Cox regression models (data not shown).

Figure 9A:
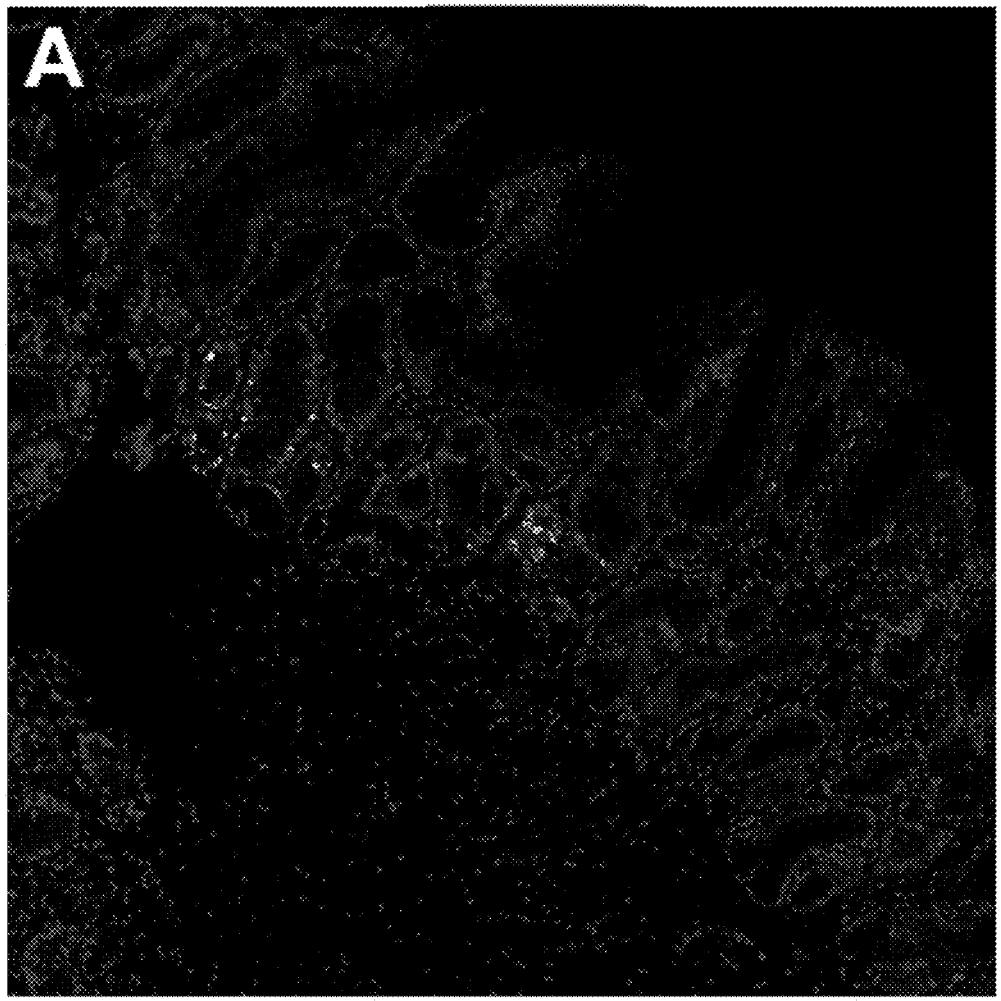
FIG. 9A-FIG. 9P illustrates representative Images of High Risk Biomarkers in BE Biopsies.
Figure 9B:
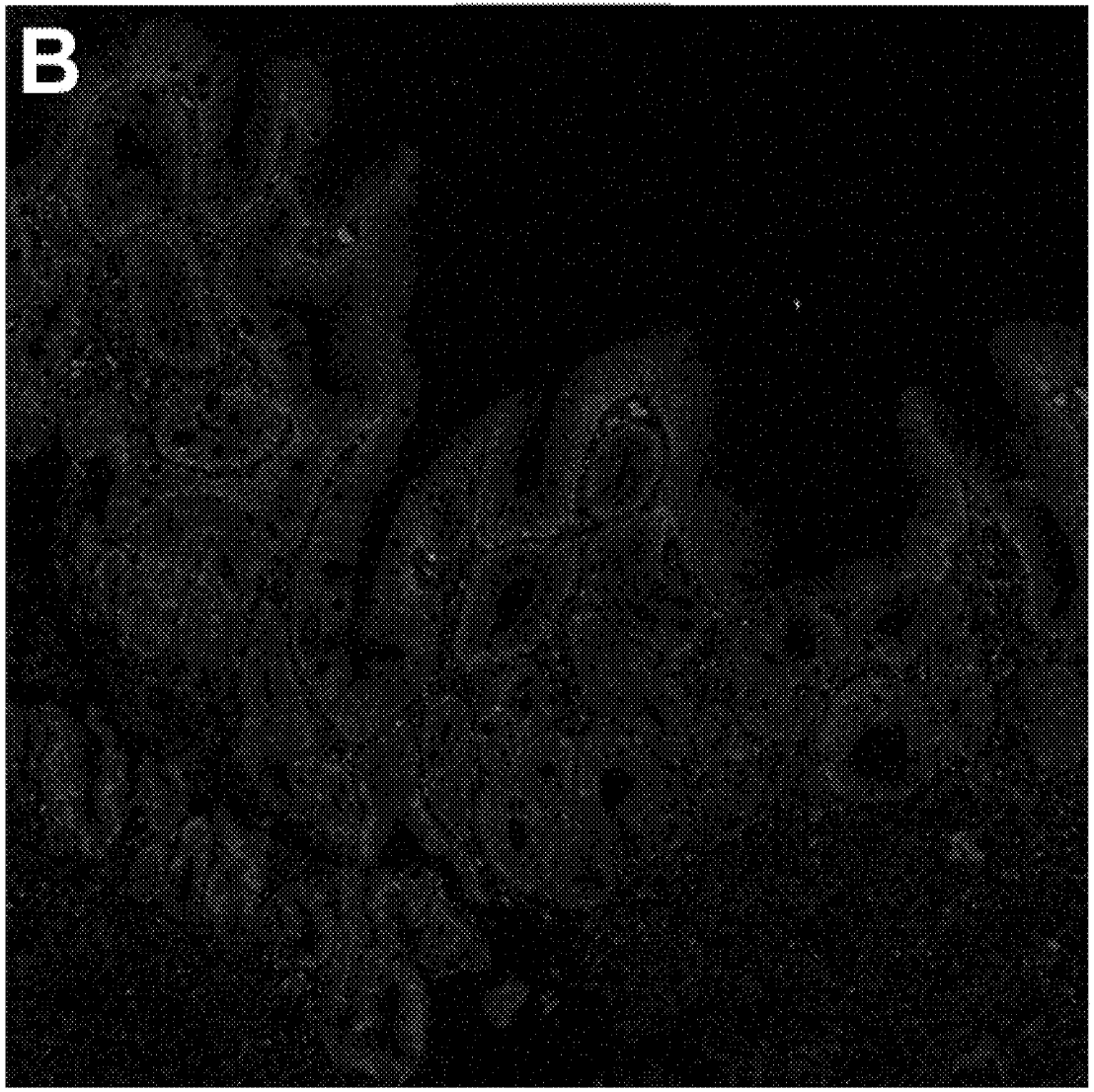
Figure 9C:
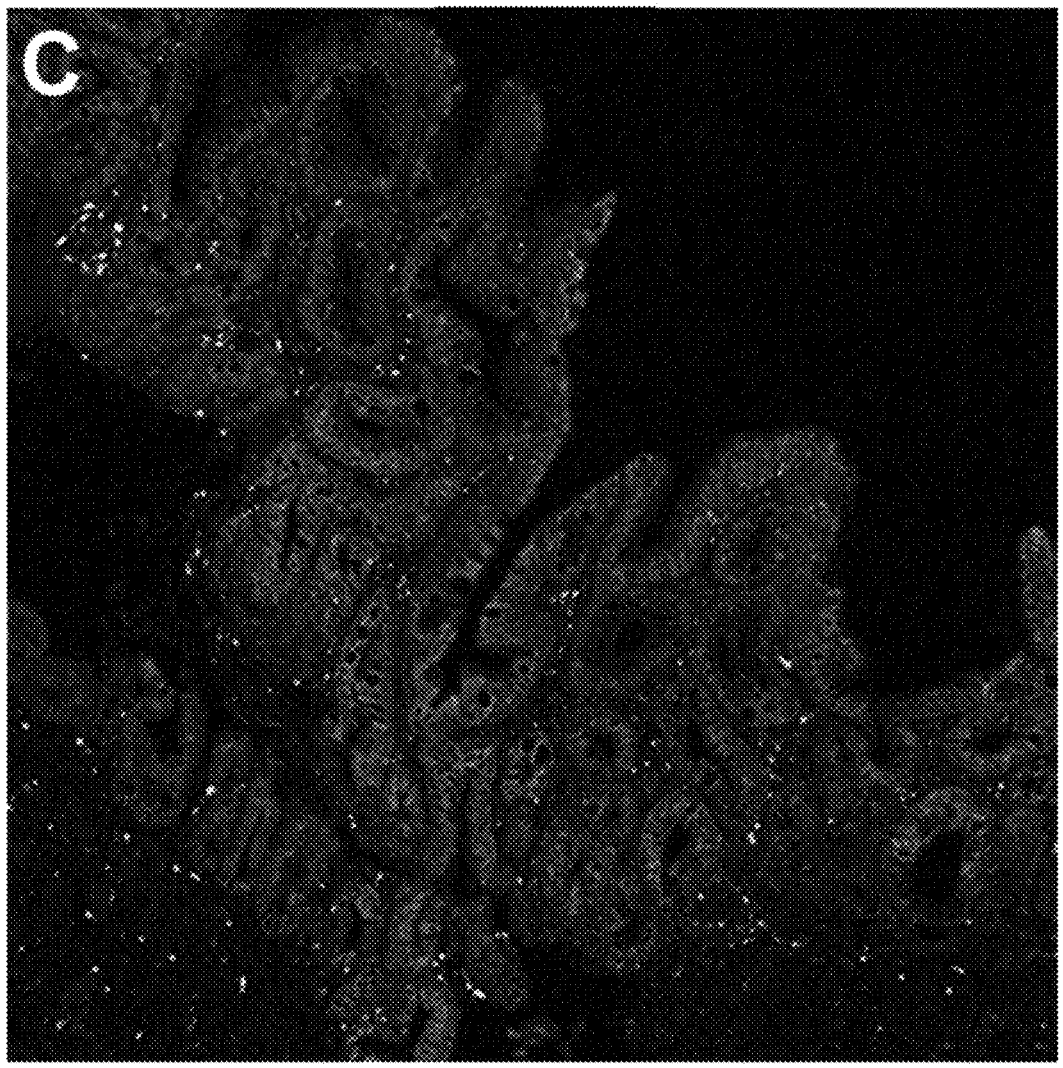
Figure 9D:
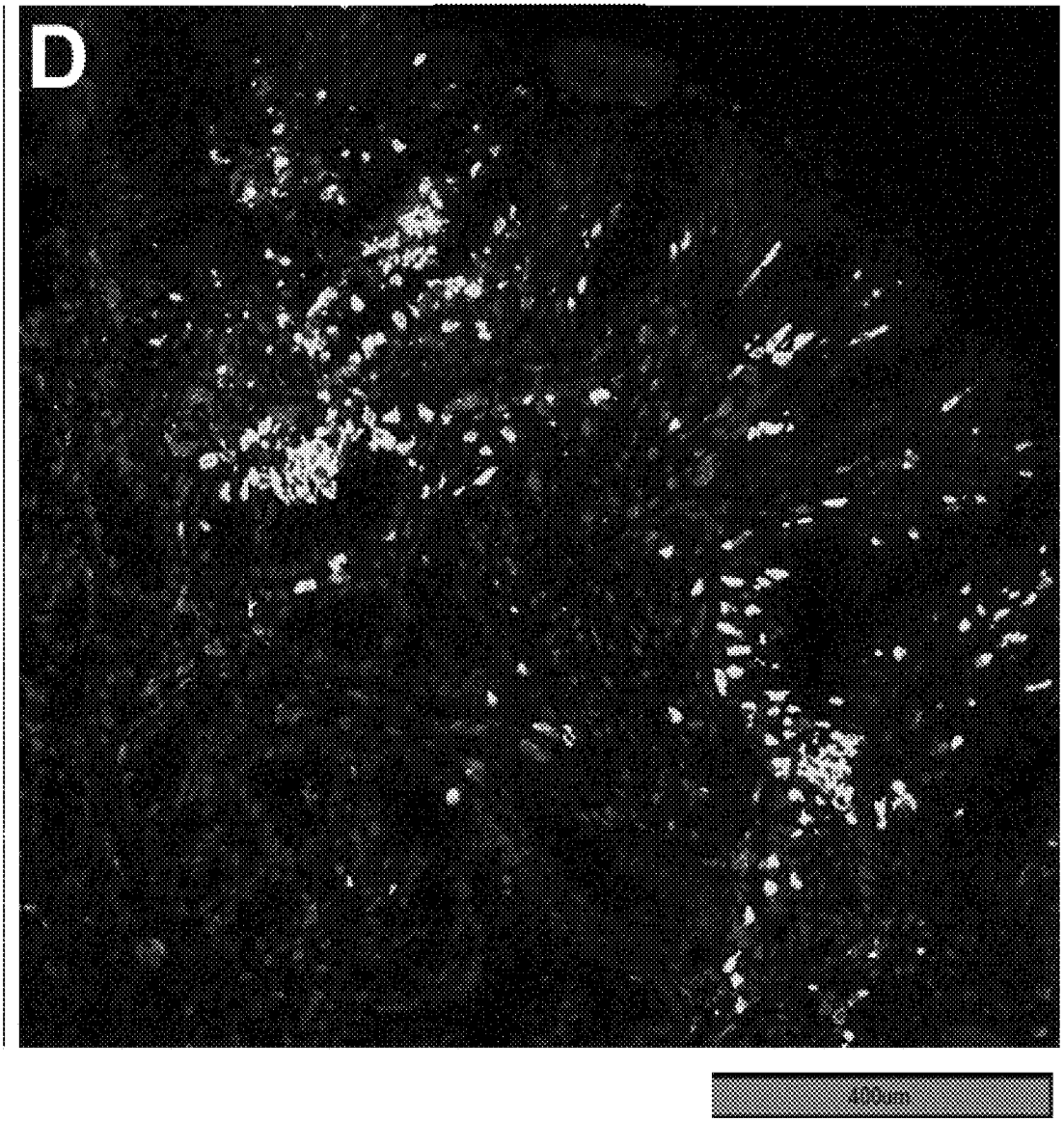
Figure 9E:
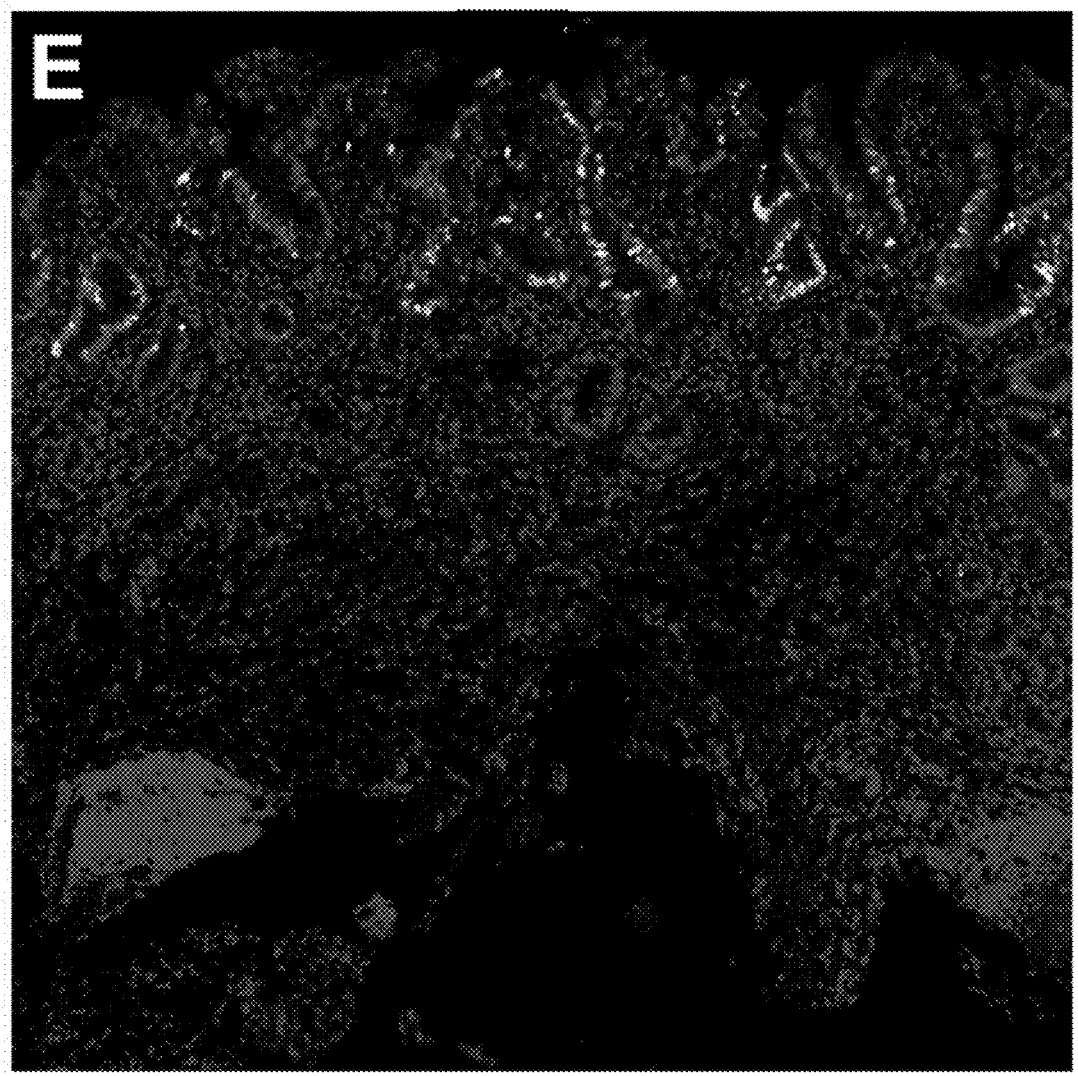
FIG. 9E-FIG. 9H show a LGD biopsy from a patient who had HGD on repeat endoscopy 56 days later.
Figure 9F:
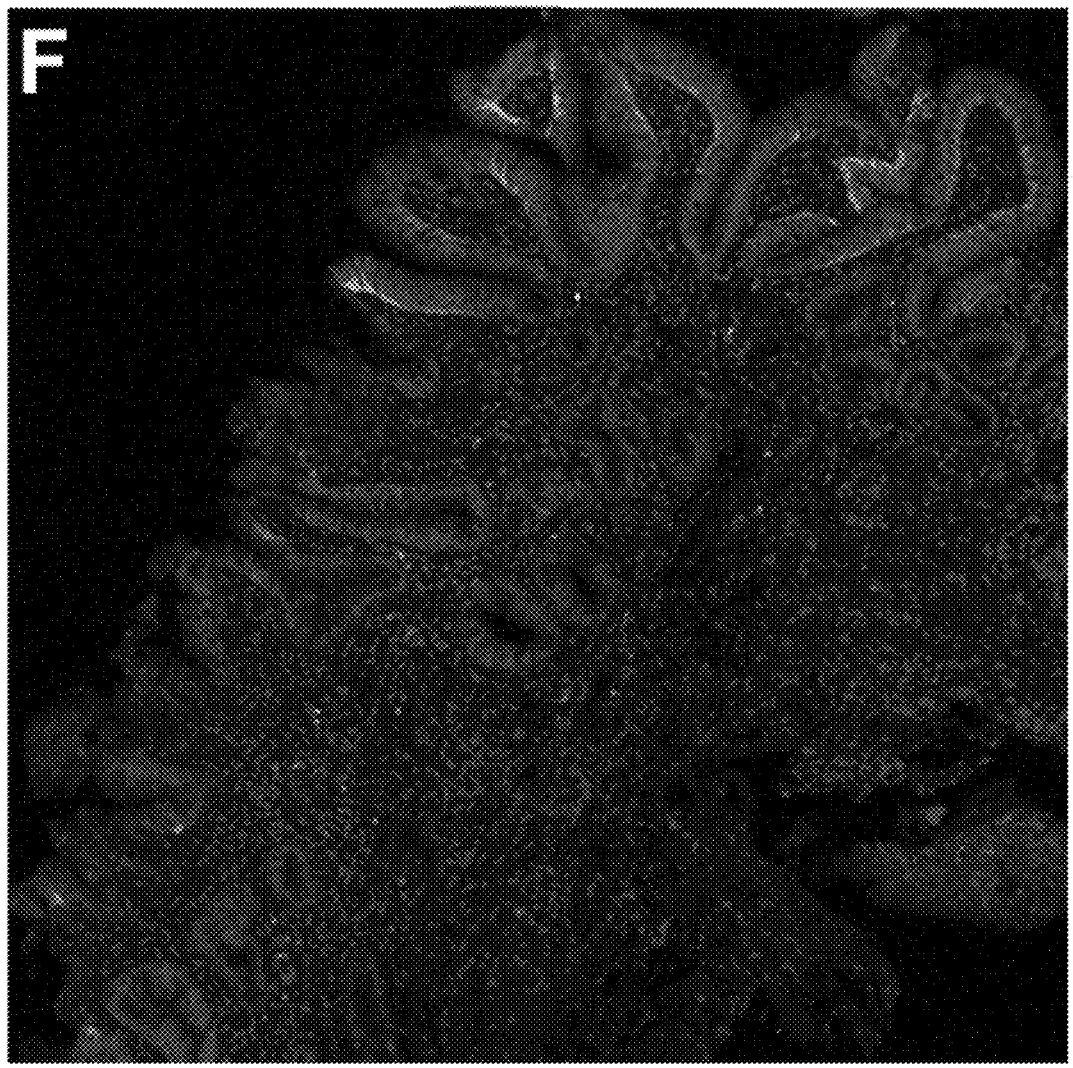
Figure 9G:
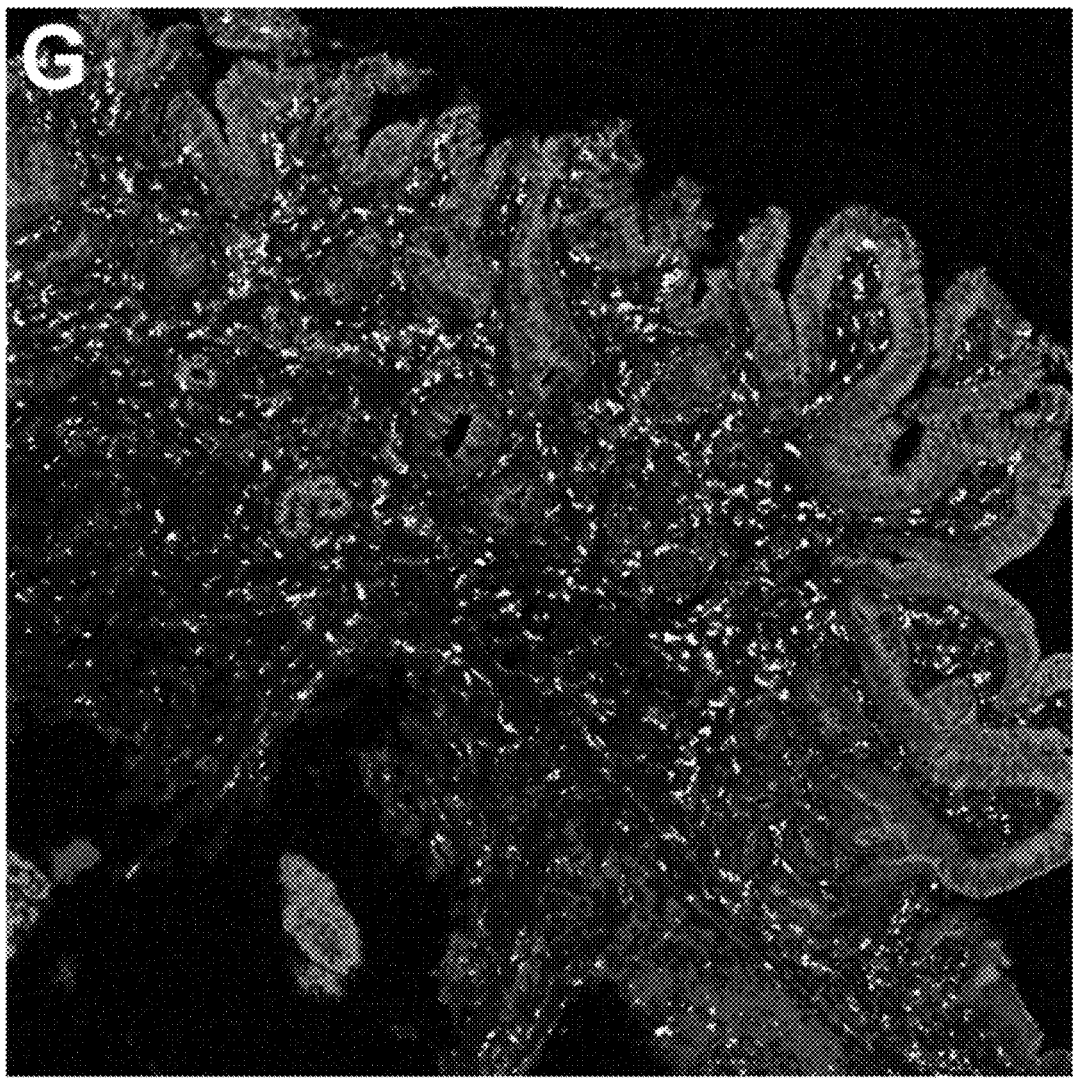
Figure 9H:
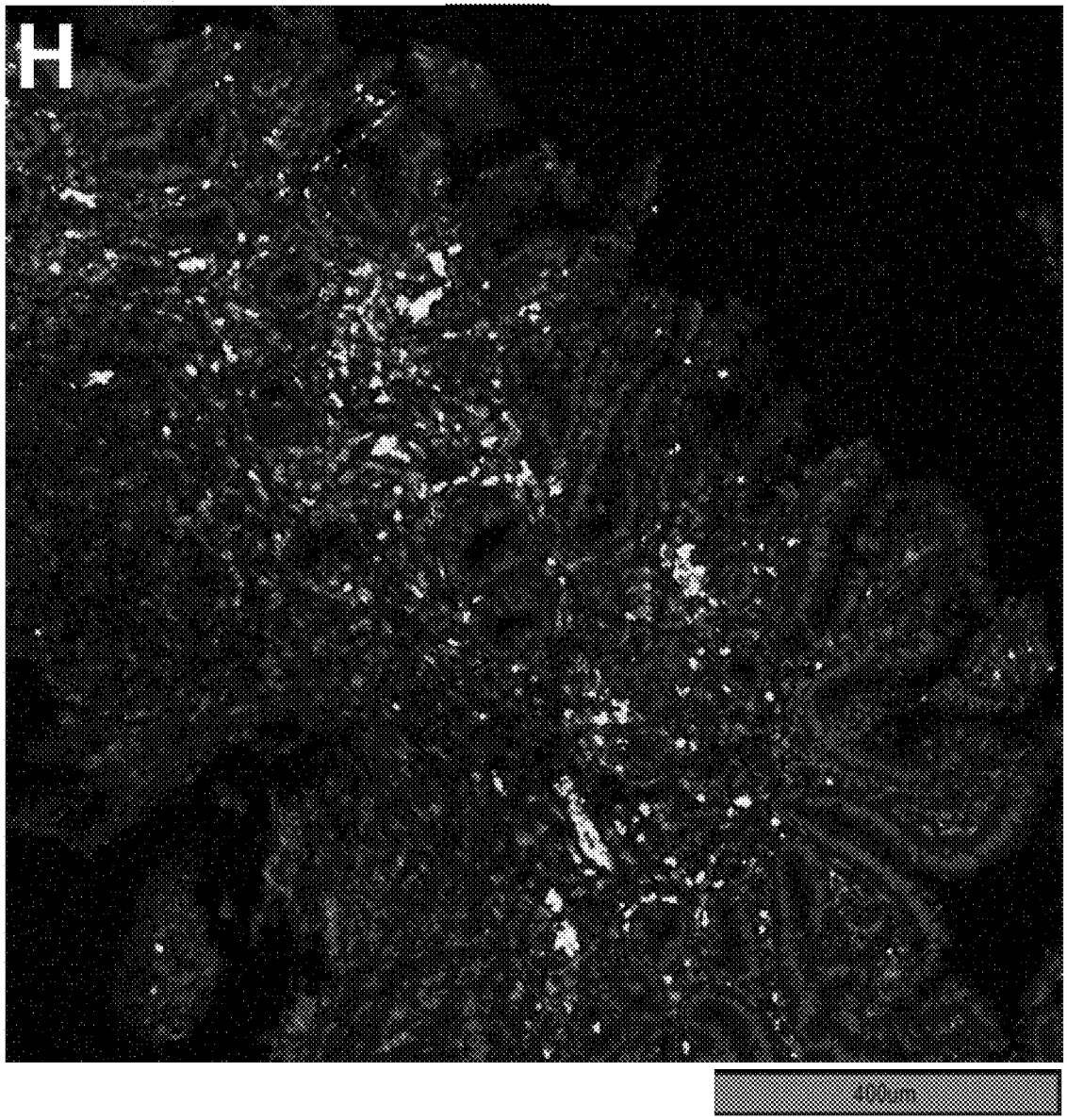
Figure 9I:
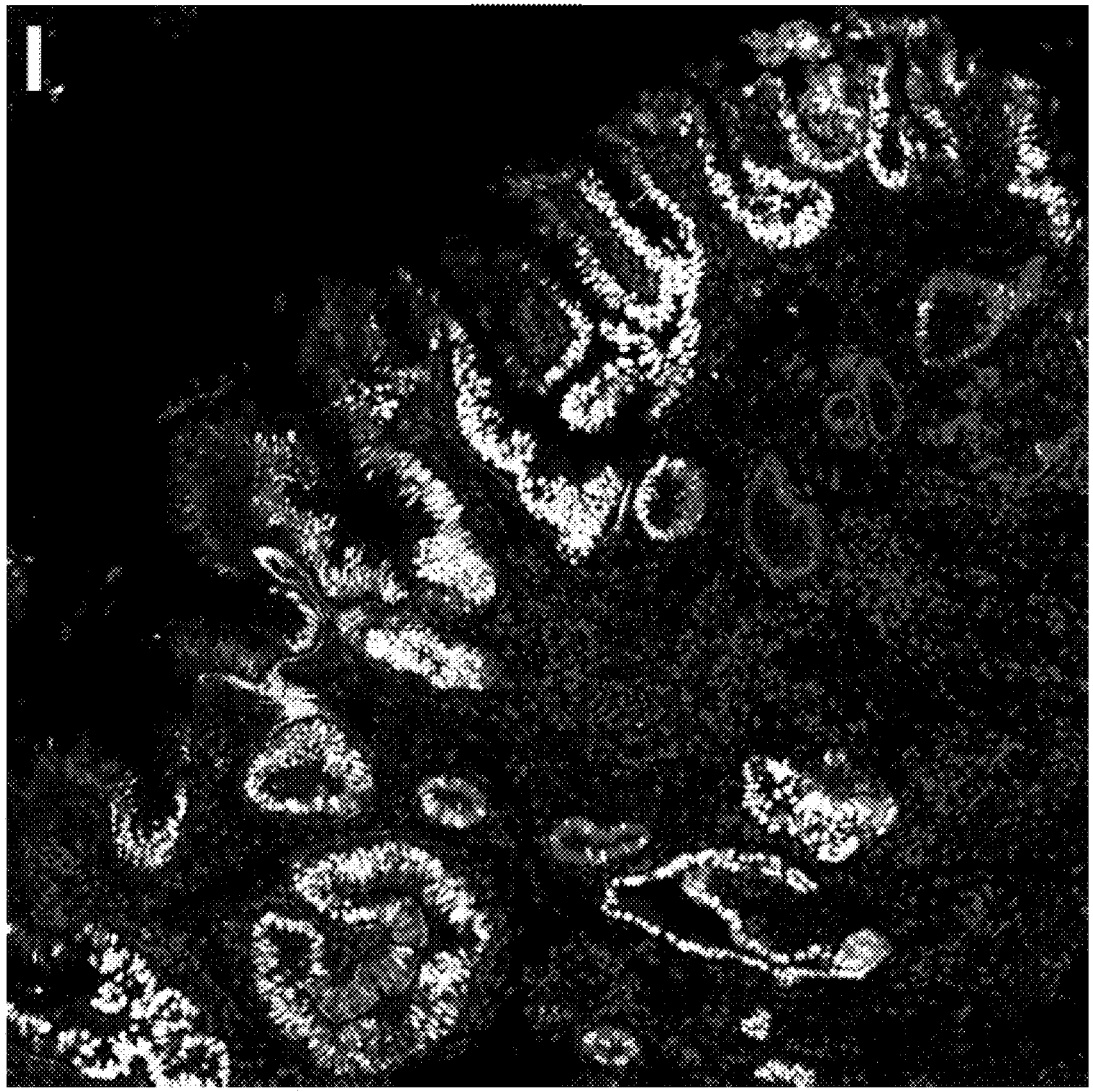
FIG. 9I-FIG. 9L show a LGD biopsy from a patient who had HGD on repeat endoscopy 60 days later.
Figure 9J:
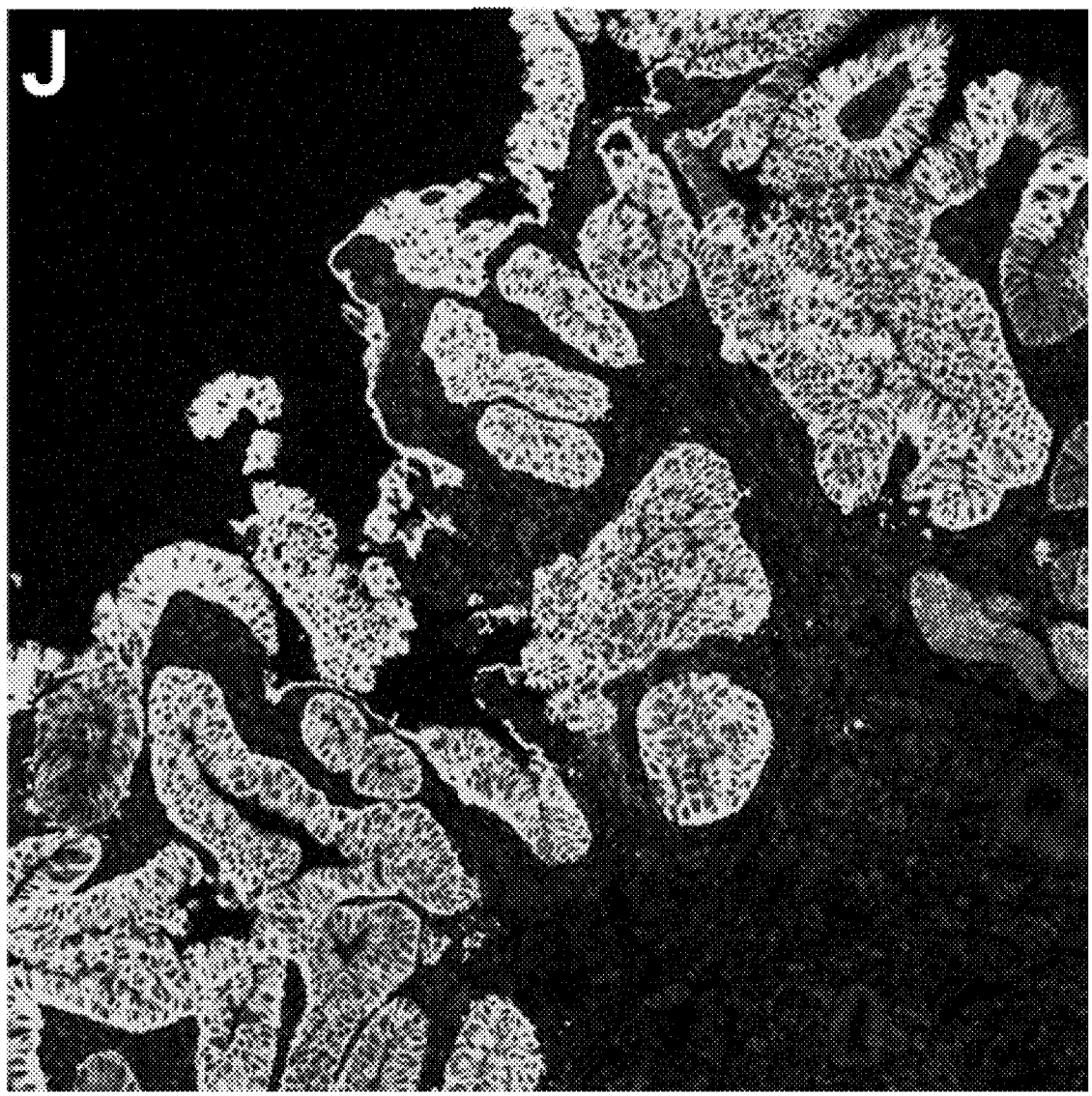
Figure 9K:
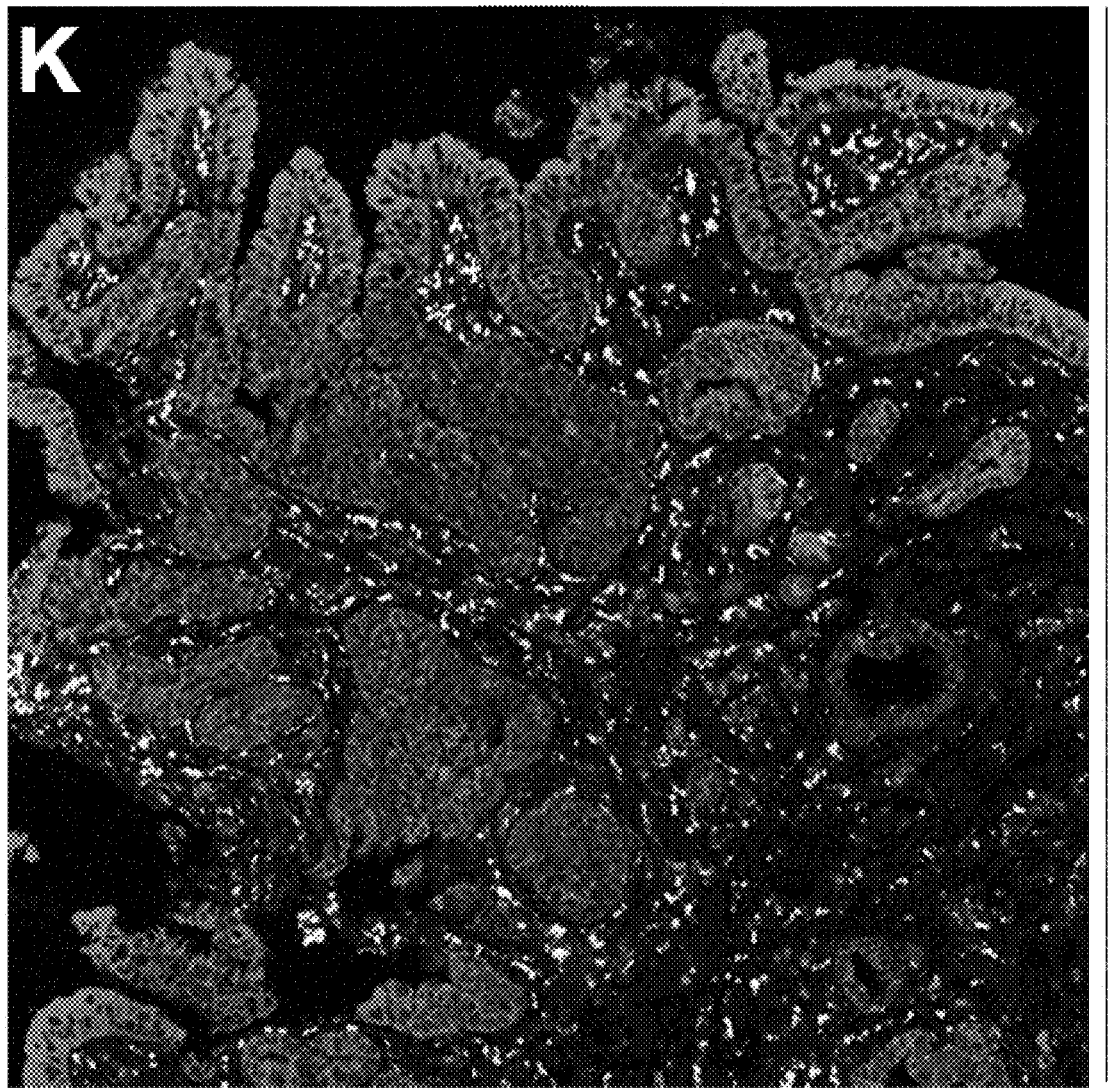
Figure 9L:
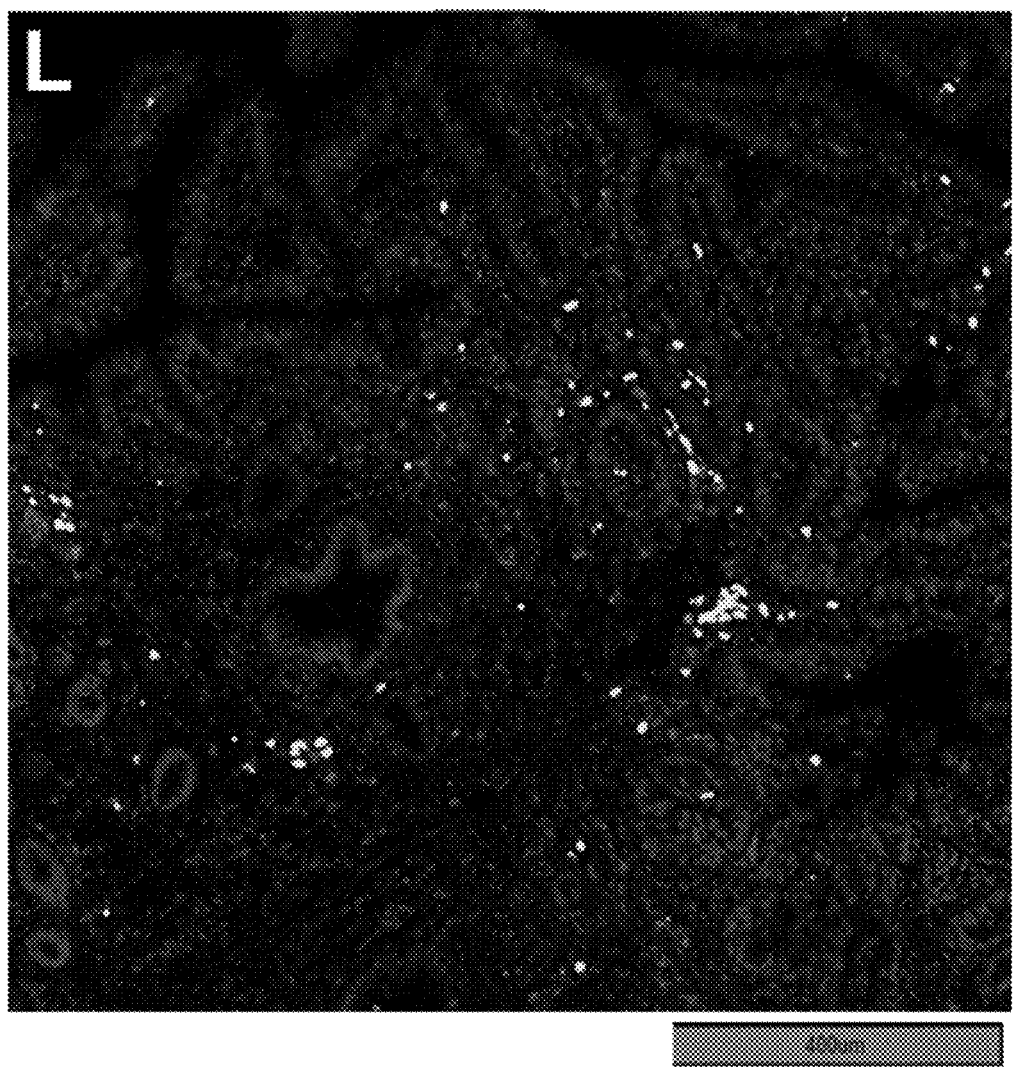
Figure 9M:
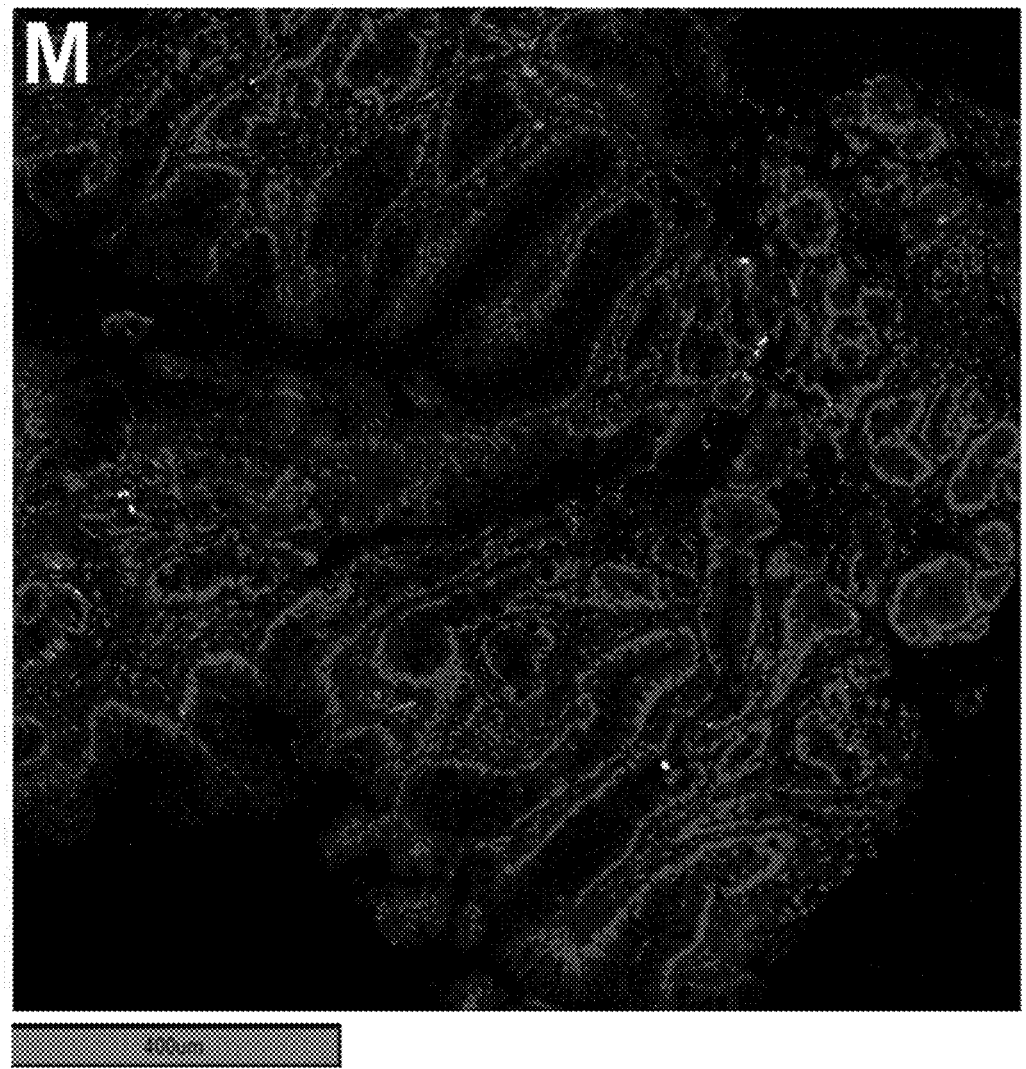
Figure 9N:
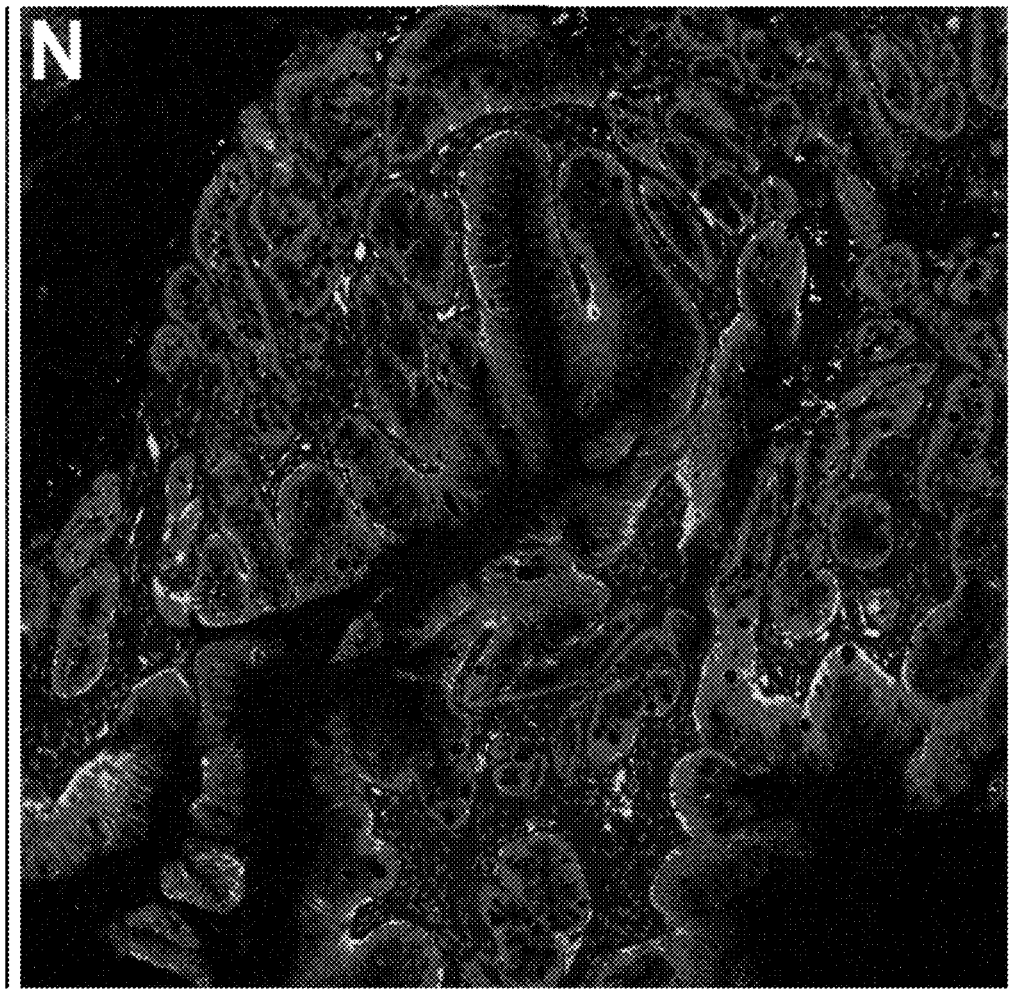
Figure 9O:
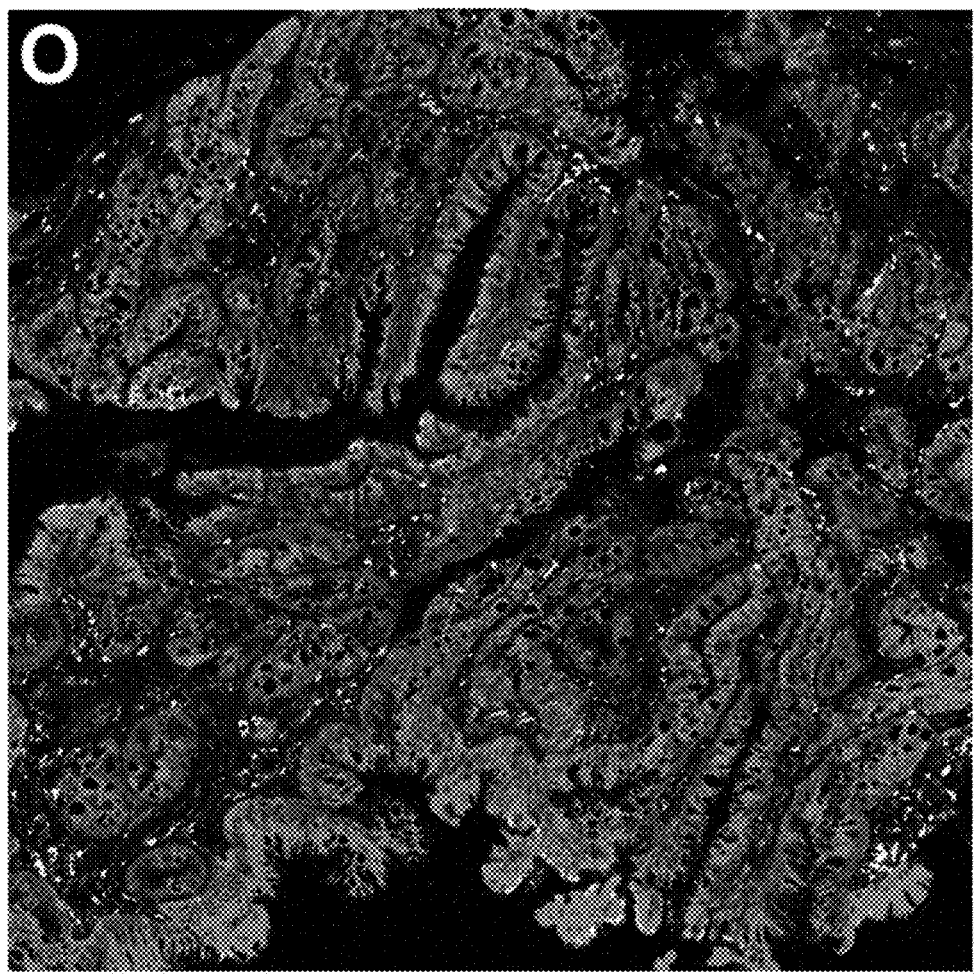
Figure 9P:
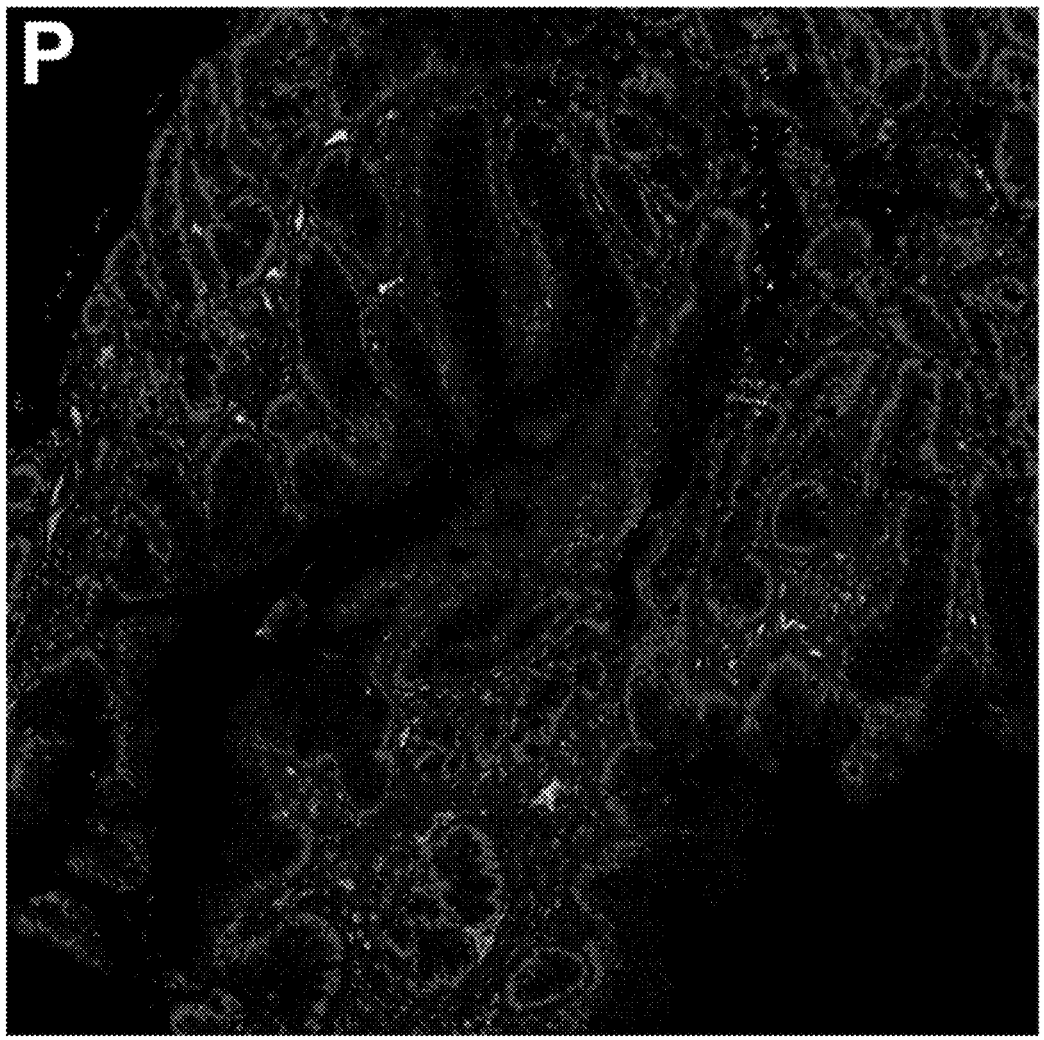
Figure 10A:
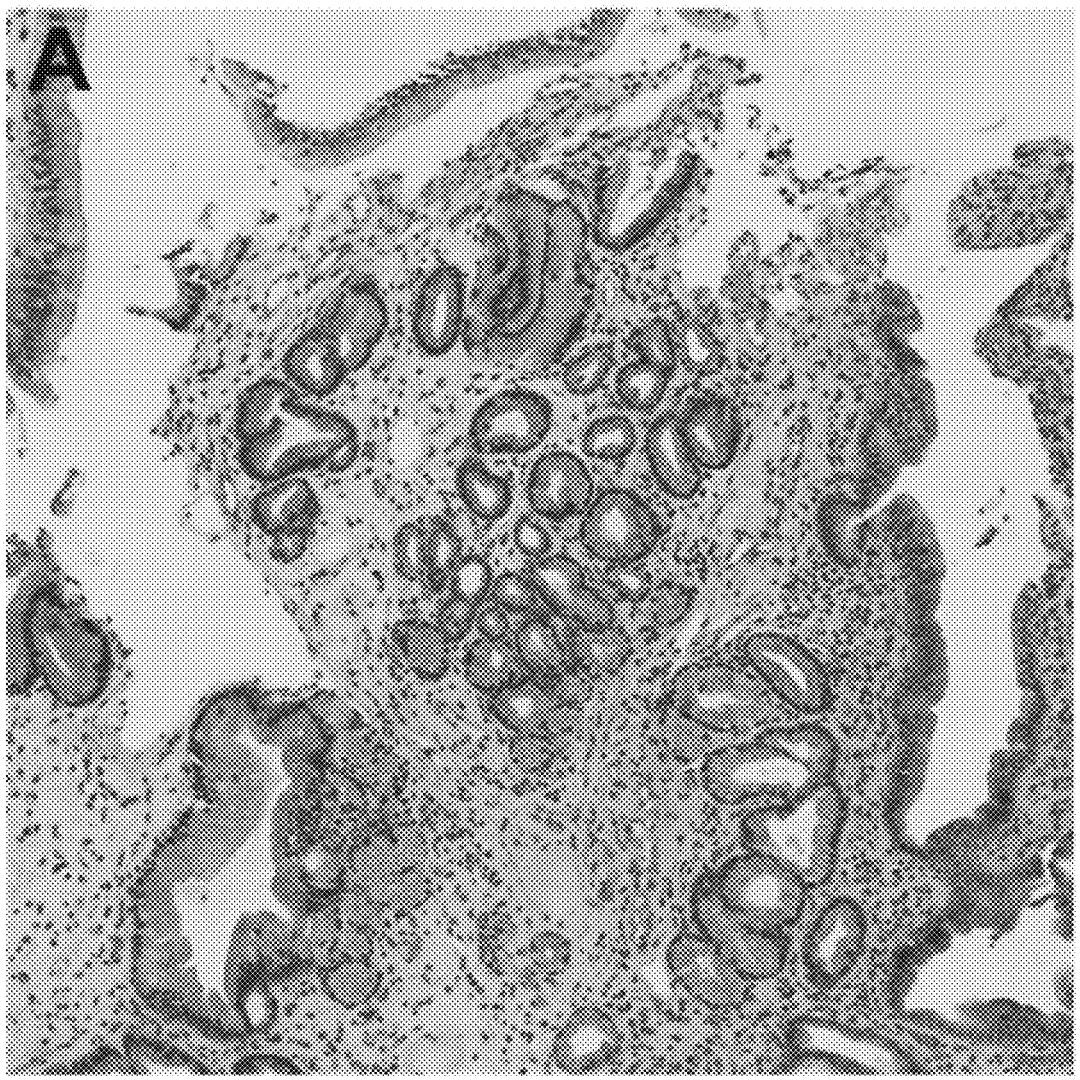
FIG. 10A-FIG. 10J illustrates representative Images of High Risk Biomarkers and Risk Scores at Multiple Endoscopic Levels.
Figure 10B:
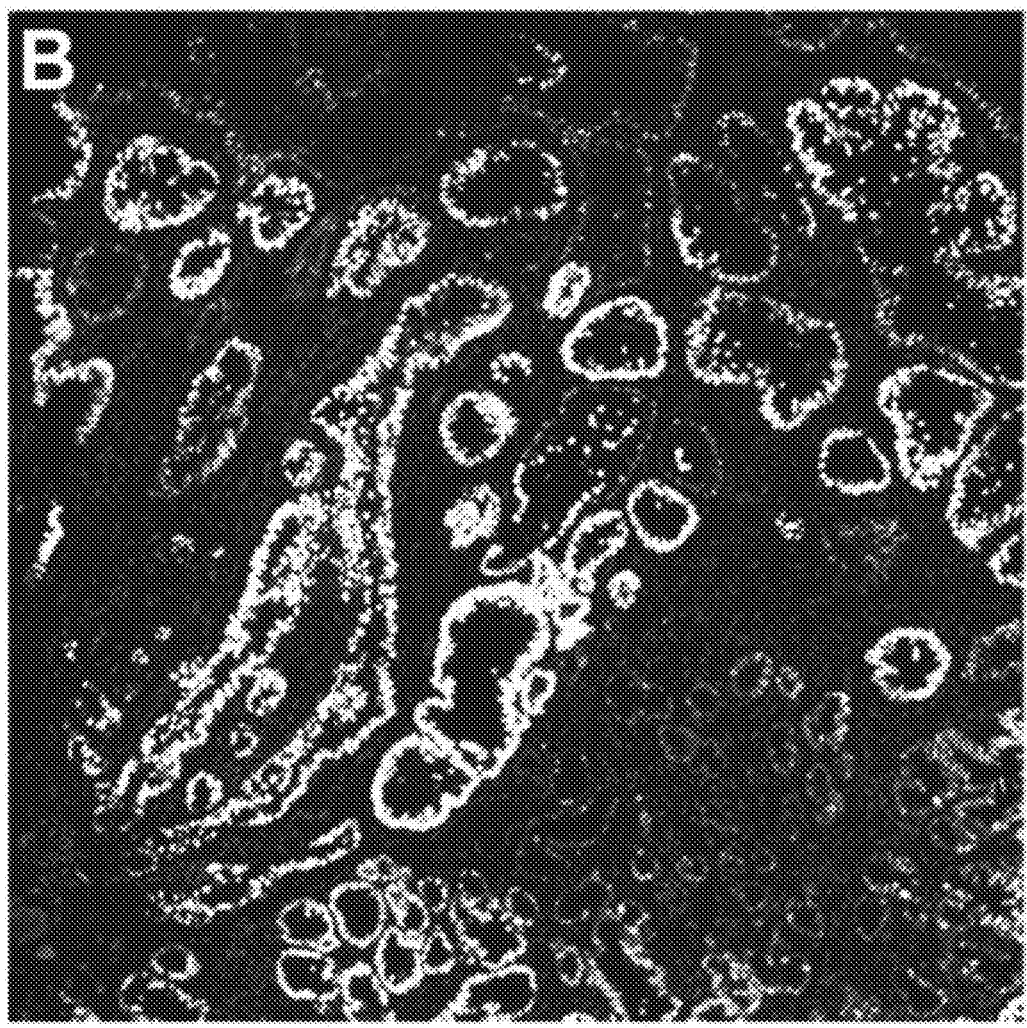
Figure 10C:
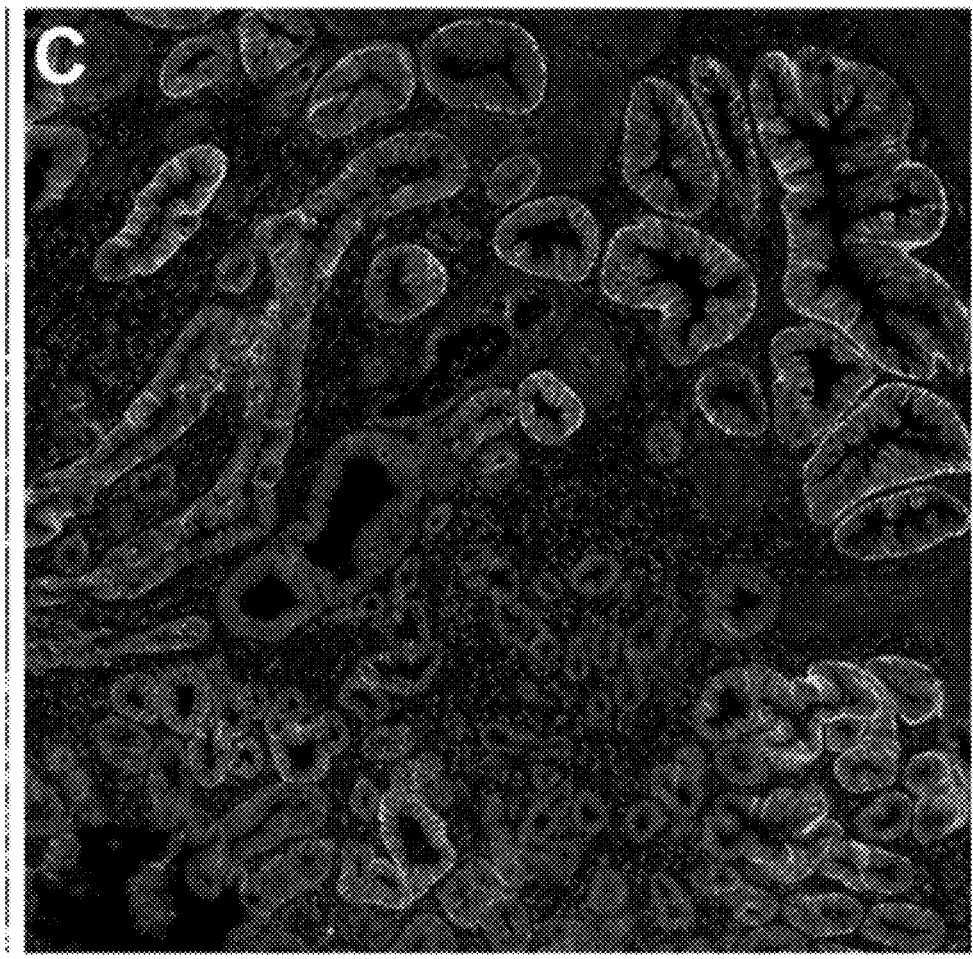
Figure 10D:
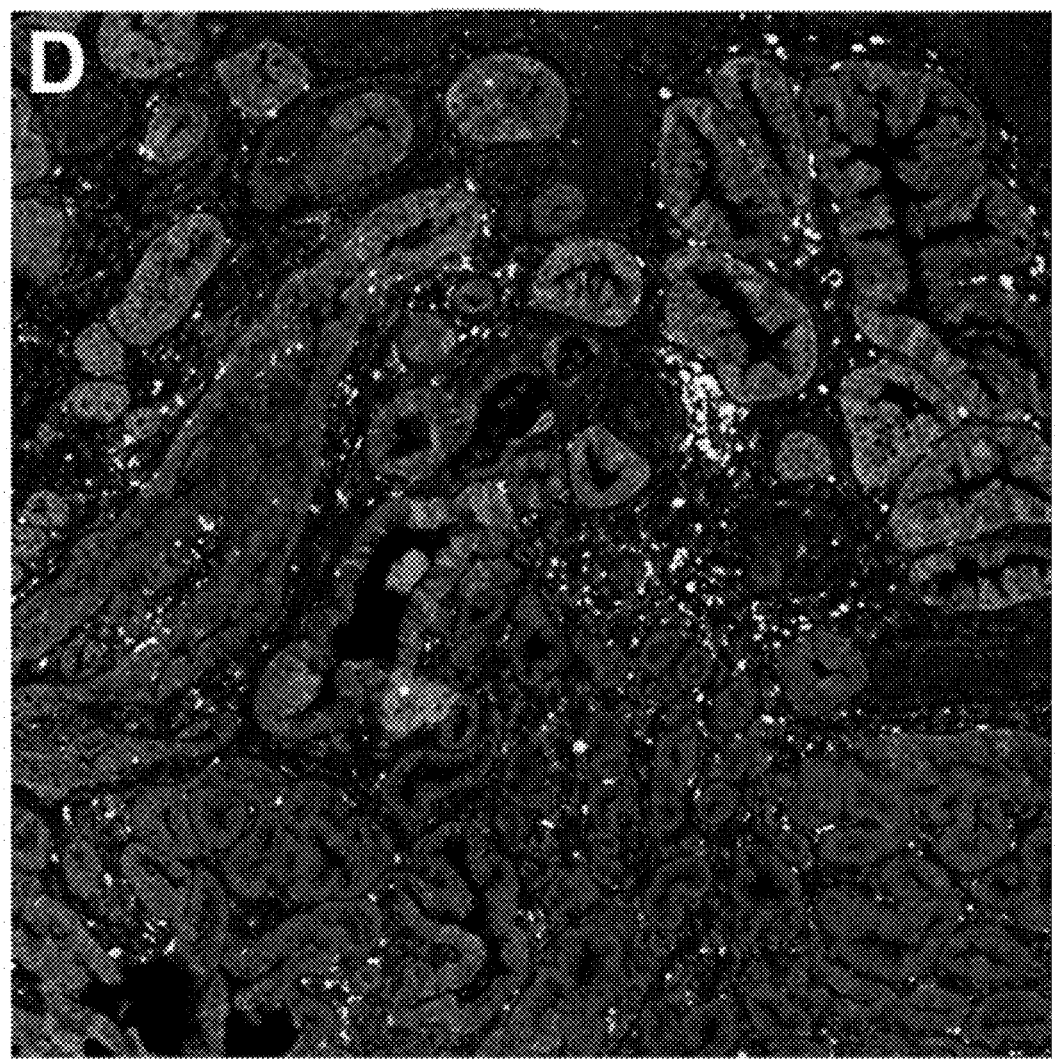
Figure 10E:
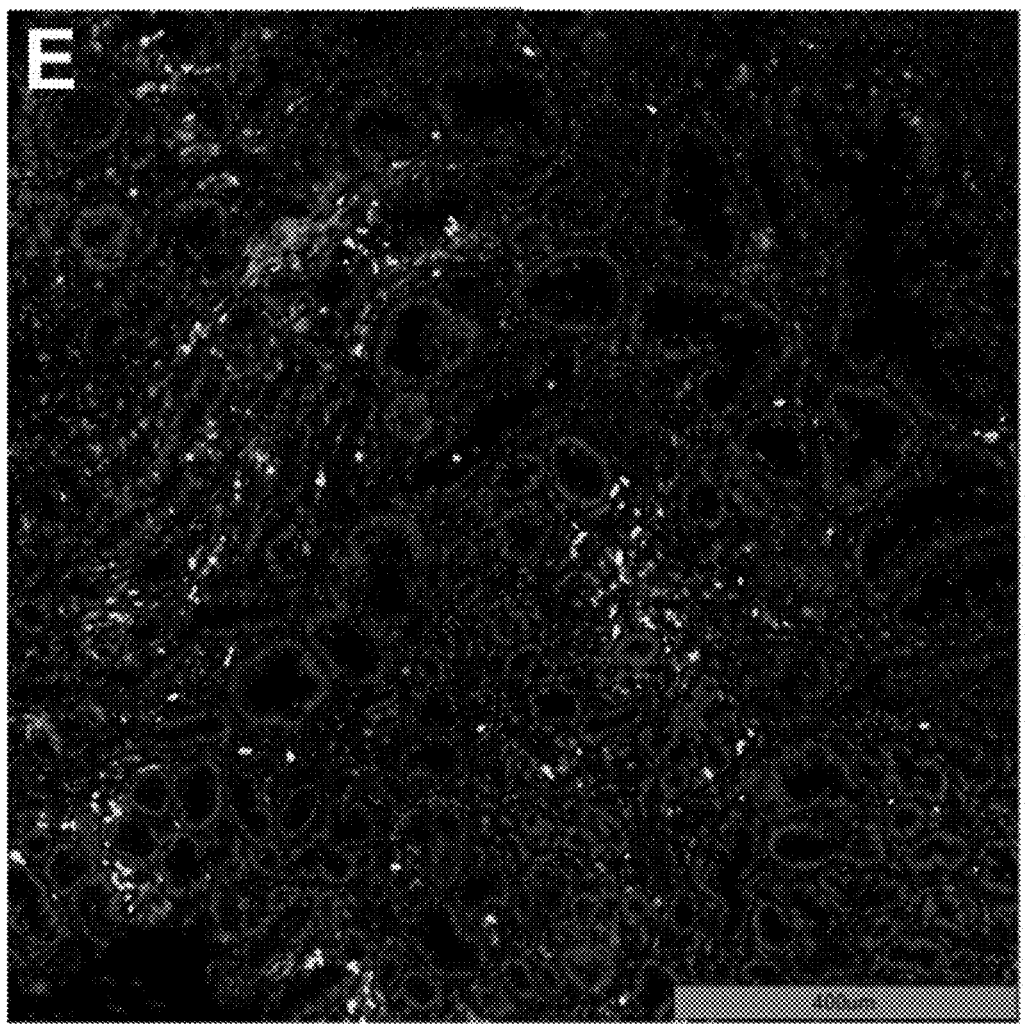
Figure 10F:
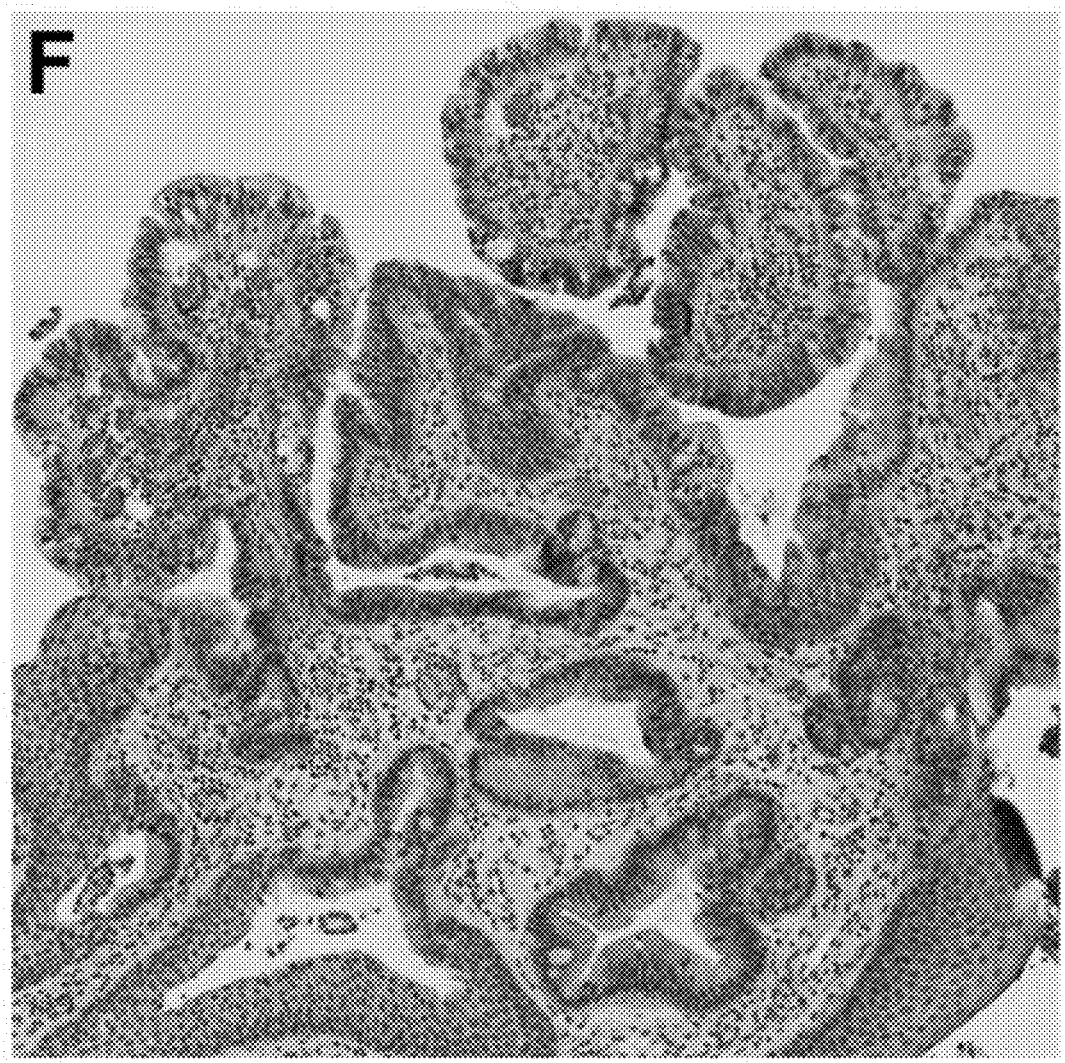
Figure 10G:
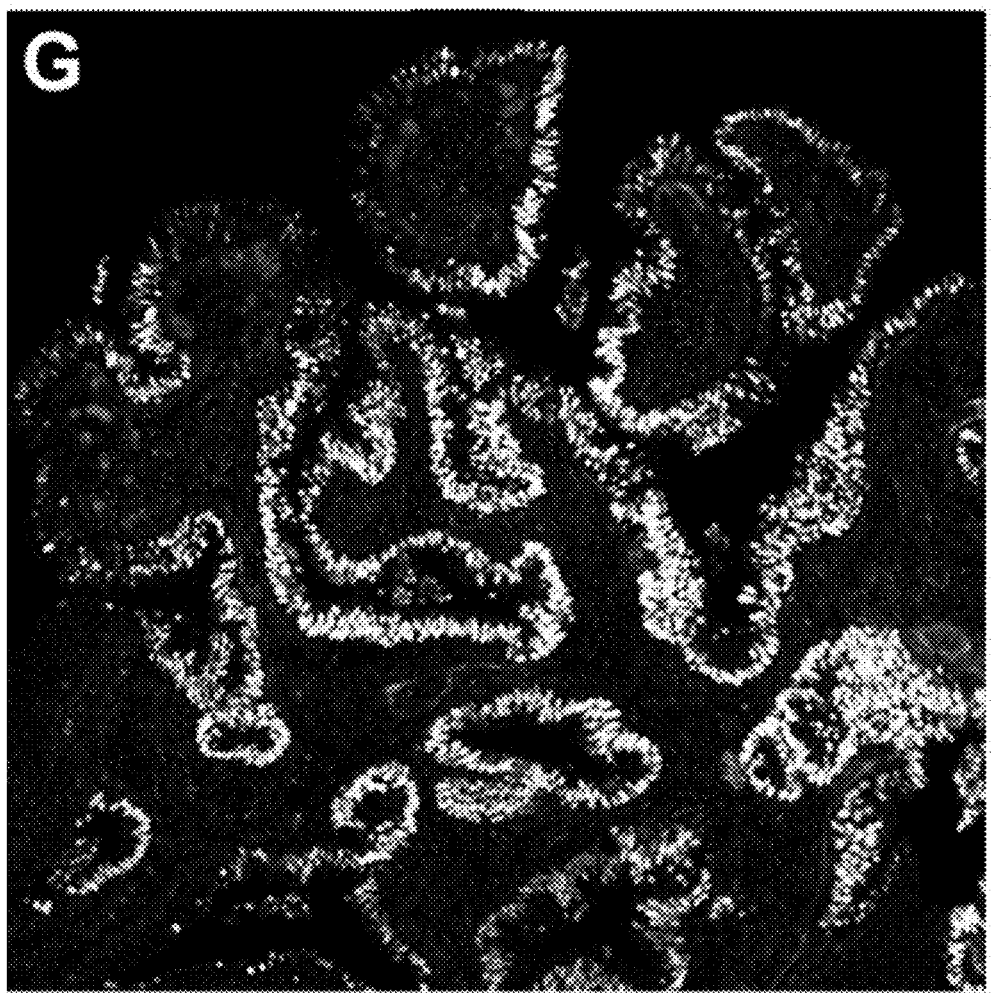
Figure 10H:
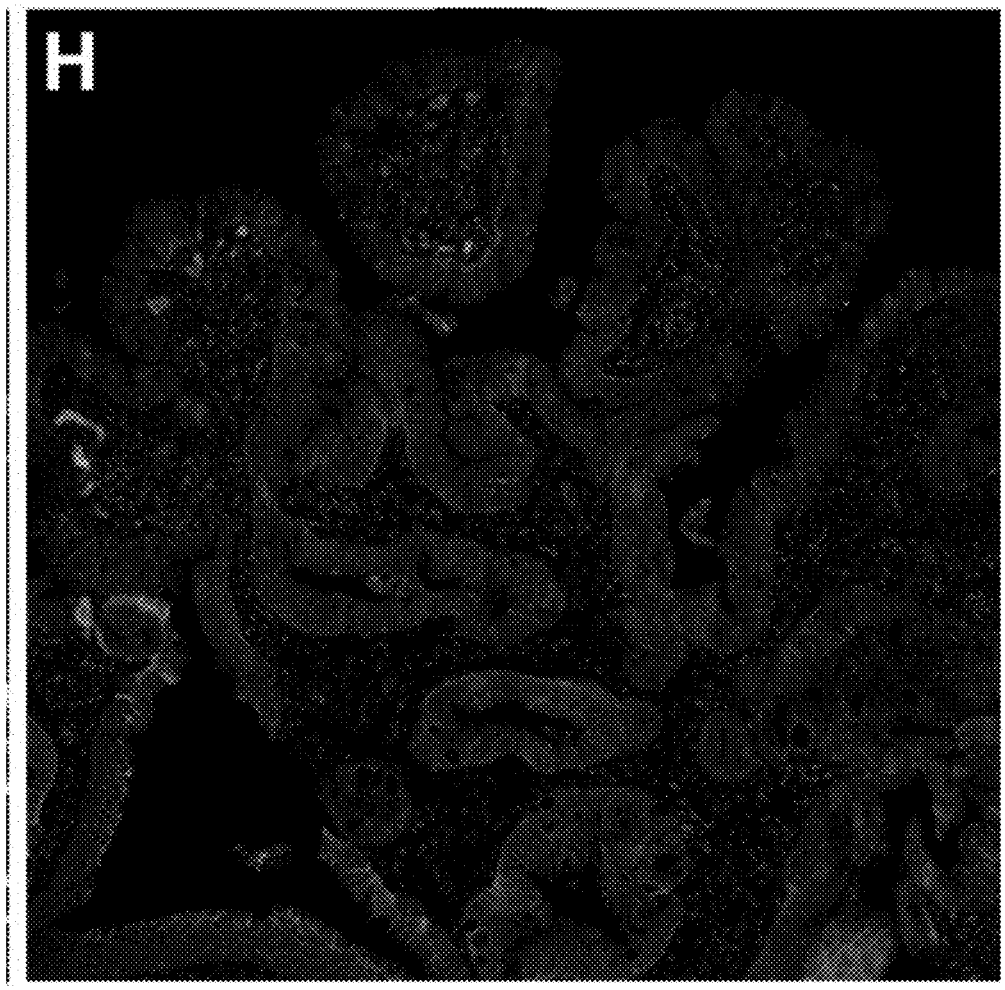
Figure 10I:
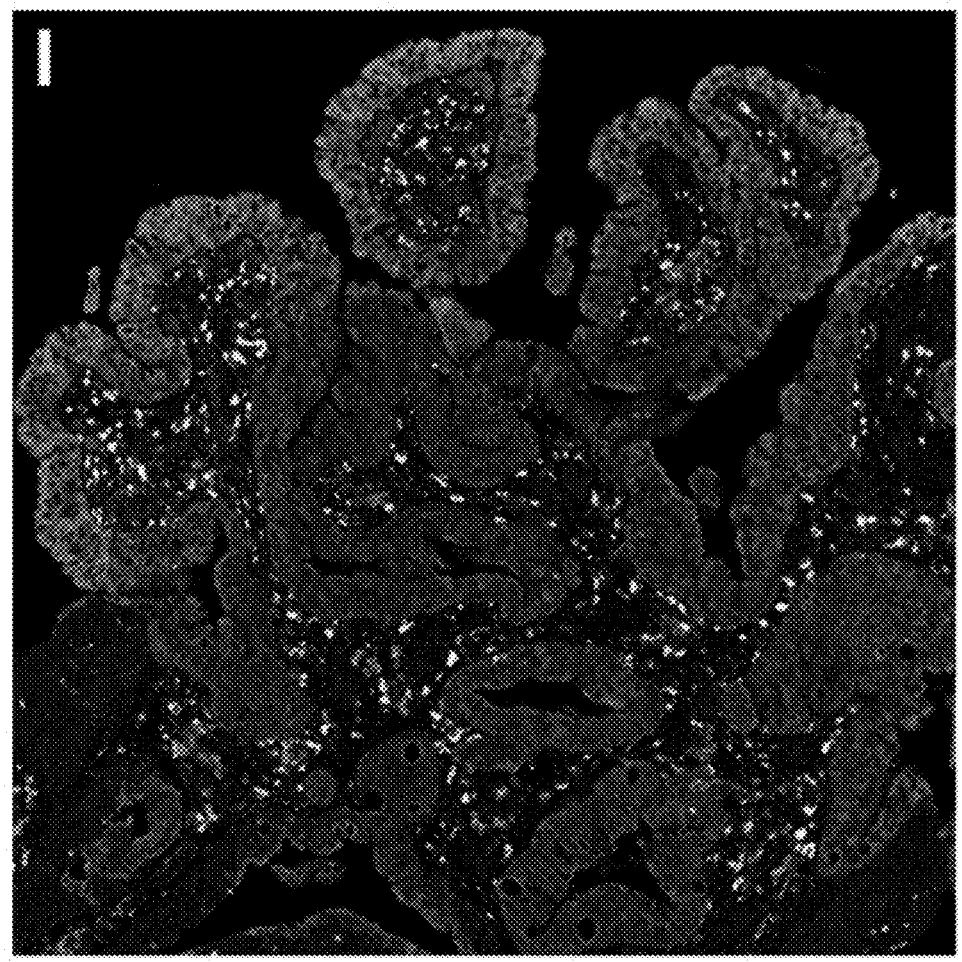
Figure 10J:
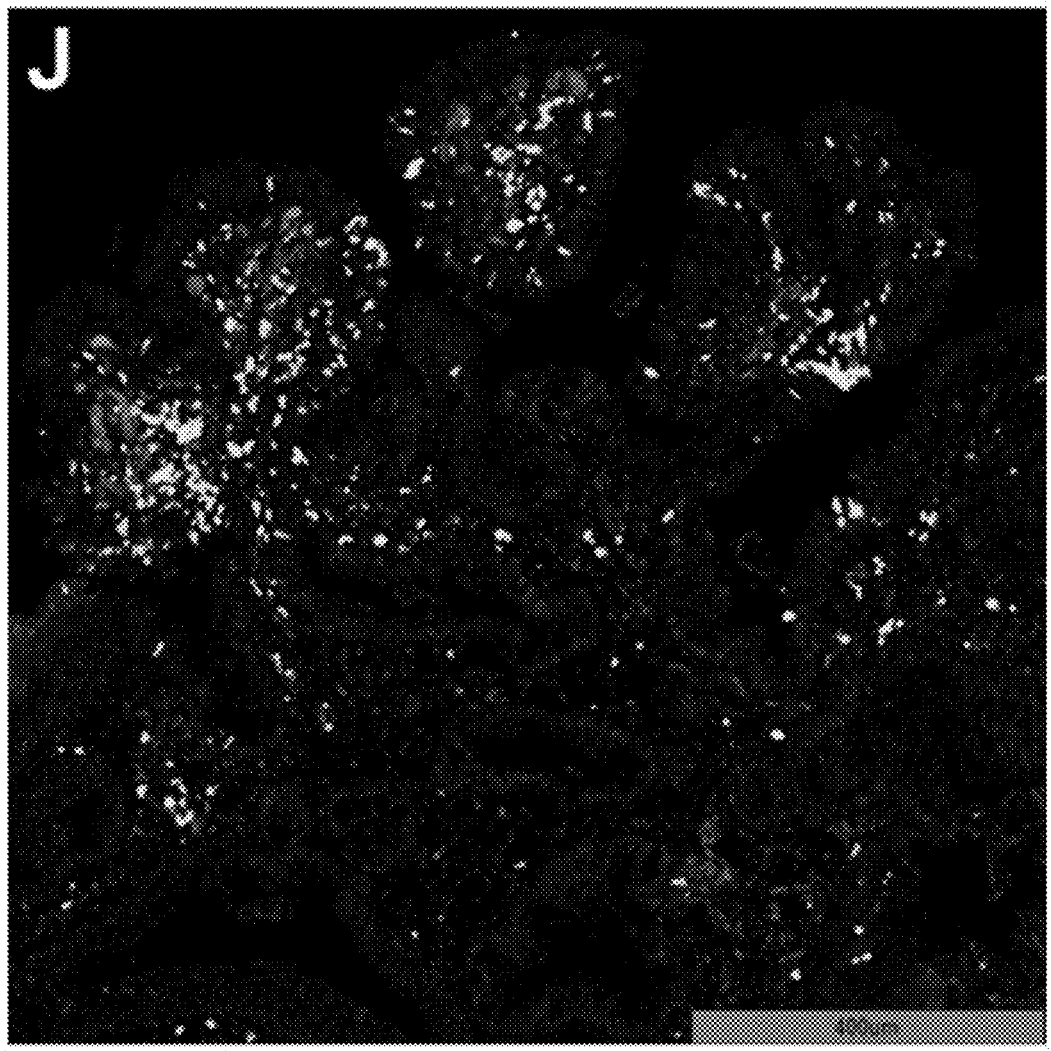

The patients identified as high-risk exhibited multiple epithelial and stromal abnormalities that are quantified by the 15 image analysis features utilized by the risk classifier. Abnormalities detected in ND and LGD biopsies in patients with prevalent HGD/EAC included overexpression of p53, HER2/neu and COX-2, focal AMACR overexpression, infiltration of the lamina propria by CD45RO-positive cells, CD68-positive cells and stromal cells expressing HIF-1α (FIG. 9A-FIG. 9P). The stronger predictive power of the risk classes compared to the pathologic diagnosis was illustrated in a patient with 2 cm segment BE with biopsies available from two endoscopic levels. Biopsies from 32 cm and 34 cm were diagnosed as ND and LGD, respectively, by a GI subspecialist in this study, and as ND and IND, respectively, by a general pathologist who recorded the original diagnosis. Repeat biopsy 56 days later showed HGD. Biopsies from the two levels, which were evaluated for illustrative purposes, scored 8.9 and 8.7 (on a scale of 0-10) with the 15-feature risk score, demonstrating that similar high-risk molecular and cellular changes were present at both biopsy levels despite the different pathologic diagnosis (FIG. 10A-FIG. 10J).

Discussion: Using a case-control study design we validated a multivariable classifier that assesses ND, IND and LGD biopsies to detect prevalent HGD/EAC in BE patients. The test integrates quantitative biomarker and morphometric data into a risk score, and incorporates 3-tier risk stratification to classify patients as low-, intermediate- or high-risk for HGD/EAC. The predicted high-risk group of patients was at 46-fold increased risk for prevalent HGD/EAC compared to the low-risk group. Importantly, the risk classes provided stronger predictive power than the expert GI and generalist pathologic diagnosis in this cohort of patients, and demonstrated high accuracy in detecting presence of prevalent HGD/EAC, even in non-dysplastic biopsies. The tissue systems pathology assay used in this study thus has the potential to provide physicians and patients with an individualized score that indicates potential for prevalent HGD/EAC, which may aid in decision-making on more rigorous surveillance examinations and endoscopic therapy in BE patients with ND, IND or LGD. This study was strengthened by the use of a diverse patient cohort from four high-volume institutions in the US and Europe. The study was further strengthened by the assay technology, which evaluates multiple pathways associated with carcinogenesis, and is also quantitative and objective. The assay can be performed on sections from FFPE blocks and is thus compatible with clinical practice.

Expert referral centers have higher rates of detection of HGD/EAC and mucosal abnormalities than community centers, but recognition of subtle lesions containing HGD and early EAC can be challenging in all settings. Endoscopic surveillance is effective when done in accordance with practice guidelines, however, adherence to the guidelines varies between settings. HGD and early EAC may be missed by random sampling, which can result in repeat endoscopies and delays in diagnosis and treatment of HGD and EAC. A diagnosis of LGD confirmed by multiple GI subspecialists is a strong predictor of malignant progression. However, intraobserver variability in the diagnosis, even among GI subspecialists, has been well documented.

Despite extensive efforts to identify and validate biomarkers in BE none have yet been translated into practice to overcome the limitations of random sampling via detection of a field effect. p53 IHC has been demonstrated to have diagnostic and prognostic significance in BE. However, assessment of p53 alone is not sufficient since not all patients have detectable abnormalities in p53 protein levels, and a subset of patients who exhibit p53 abnormalities do not develop HGD or EAC. Molecular approaches such as DNA sequencing, gene expression, mutation and methylation profiling have been applied to diagnostic and prognostic testing in BE but have not yet been evaluated in the detection of abnormalities in the expanded field surrounding HGD and EAC. These technologies have the disadvantage of requiring tissue digestion, resulting in loss of contextual information, such as nuclear morphology, and spatial relationships that are relevant to patient outcomes. Further disadvantages include the requirement for fresh frozen specimens for some of these genomic approaches, which is a logistical problem in clinical practice, and also the need for laser microdissection of tissue areas based on subjective review for some of these approaches.

The risk classifier evaluated in this study identifies patients who have prevalent HGD/EAC, despite receiving a pathologic diagnosis of ND, IND or LGD. The abnormalities quantified by the assay include loss of tumor suppression, loss of cell cycle control, morphologic changes, increased inflammation, stromal angiogenesis, and altered patterns of infiltrating immune cells. If validated in additional studies, this finding suggests that objective detection of multiple molecular and cellular abnormalities in the preneoplastic field of BE could overcome some of the limitations of random endoscopic sampling and pathologic diagnosis, and enable earlier detection of HGD/EAC in all practice settings. Additional studies are required to evaluate the performance of the assay in biopsies rom different endoscopic levels. Ex-vivo tests such as this may also complement newer endoscopic techniques such as volumetric laser endomicroscopy by providing objective, quantitative analysis of pathways involved in malignant transformation.

We readily recognize the limitations of this study, which include the retrospective nature of the study, the case-control cohort study design in which the proportion of prevalent cases was not representative of the general population, and the small number of available prevalent cases as reflected in the wide confidence intervals we report. Additional, larger studies will be required to validate our findings. However, large prospective studies are challenging in BE due to the low prevalence of malignant progression. The set of biopsies and patients was heterogeneous; the biopsies had diagnoses of ND, IND and LGD, 22/30 patients had prevalent HGD while 8/30 had prevalent EAC, and the intervals between the biopsy tested and the repeat endoscopy demonstrating HGD/EAC were variable. Biopsies from a single endoscopy level were evaluated in this study, and additional studies are required with biopsies from multiple endoscopy levels from patients with subtle lesions containing HGD or early EAC. The cohort in this study included patients in surveillance at multiple centers in the US and Europe over a wide timeframe, which prevented standardization of pre-analytic variables. However, the biopsies reflect routine samples requiring accurate risk assessment.

The assay requires instrumentation and software that could not easily be integrated into current pathology laboratories, which are only beginning to adopt digital pathology. The assay has been deployed in a central reference laboratory equipped with the necessary resources, which enables physicians at expert referral centers and community centers to order the assay. Unstained slides can be sent to the reference laboratory, the assay is performed and the laboratory provides a clinical report to the ordering physician and submitting pathologist. The testing process takes approximately 3 business days. The testing approach would initially add to the cost of BE surveillance. However, risk prediction testing has the potential to result in cost savings in high-risk patients by reducing repeat endoscopies and pathologist time required to diagnose HGD/EAC, enabling earlier intervention with endoscopic therapies to reduce EAC incidence and mortality. In low-risk patients there is the potential to lower future costs by extending surveillance intervals. While it is feasible to test biopsies from multiple levels in long segment BE, this may add significant cost in a subset of patients, which may outweigh the potential cost savings from reducing unnecessary endoscopies or intervening early to prevent progression.

In summary, the tissue systems pathology assay examined in this study objectively quantifies multiple epithelial and stromal processes that predict prevalent HGD/EAC in BE patients. The assay has the potential to improve upon current histology methods to enable earlier detection of HGD/EAC, which will facilitate earlier, more effective therapeutic interventions.

TABLE 11

Patient Characteristics

|  | Non-Progressors | Prevalent Cases |
|---|---|---|
| # patients | 145 | 30 |
| HGD/EAC-free surveillance time (Median days (IQR) | 2,015 (1,498, 3,111) | 140.5 (56, 241.3) |
| Age (mean years ± S.D.) | 61.0 ± 12.1 | 61.8 ± 9.5 |
| Segment Length (%) | | |
| Short (≤3 cm) | 58 (40.0) | 9 (30.0) |
| Long (>3 cm) | 73 (50.3) | 19 (63.3) |
| Unknown | 14 (9.7) | 2 (6.7) |
| Sex (%) | | |
| Male | 114 (78.6) | 28 (93.3) |
| Female | 31 (21.4) | 2 (6.7) |

| | Non-Progressors | | | Prevalent Cases | | |
|---|---|---|---|---|---|---|
| | ND | IND | LGD | ND | IND | LGD |
| Patients in each diagnostic class (%) | 138 (95.2) | 2 (1.4) | 5 (3.4) | 13 (43.3) | 1 (3.3) | 16 (53.3) |
| End point diagnoses (%) | na | na | na | HGD 7 (53.8) EAC 6 (46.2) | HGD 1 (100) EAC 0 (0) | HGD 14 (87.5) EAC 2 (12.5) |

| Each | Non-Progressors | | | | Prevalent Cases | | | |
|---|---|---|---|---|---|---|---|---|
| Institution | AMC | Gei | UPenn | UPitt | AMC | Gei | UPenn | UPitt |
| # patients (%) | 46 (31.7) | 63 (43.5) | 15 (10.3) | 21 (14.5) | 4 (13.3) | 12 (40.0) | 7 (23.3) | 7 (23.3) |
| HGD/EAC-free surveillance time (median days (IQR) | 1,816 (1,458, 2,847.3) | 2,361 (1,522, 3,698) | 1,497 (1,277, 1,736) | 2,306 (2,055, 3,155.5) | 98.5 (60.5, 172.5) | 42 (19, 134.5) | 220 (176, 321) | 179 (123, 242) |

*surveillance time: number of days between biopsy tested and last endoscopy with ND, IND or LGD (non-progressors) or endoscopy with diagnosis HGD or EAC (prevalent cases). Diagnosis provided by GI subspecialist pathologist.
AMC: Academic Medical Center, Netherlands;
Gei: Geisinger Health System;
UPenn: University of Pennsylvania;
UPitt, University of Pittsburgh.
S.D.: standard deviation,
IQR: interquartile range.

TABLE 12

Performance of Risk Classes Predicted by Test vs. Pathologic Diagnosis in Stratifying BE Patients with Prevalent HGD/EAC from Non-Progressor BE Patients

| Variable | Odds Ratio (95% CI) | P Value |
|---|---|---|
| A. Predictive Performance of Risk Classes vs. Generalist Pathologist Diagnosis | | |
| Analysis without Risk Prediction Test | | |
| General Pathologist's Dx (LGD vs. ND/IND) | 12.67 (4.17-44.05) | <0.0001 |
| Analysis with Risk Prediction Test | | |
| General Pathologist's Dx (LGD vs. ND/IND) | 5.28 (1.42-21.39) | 0.01 |
| Risk Classes (predicted by the test) | | |
| Intermediate vs. Low Risk | 12.23 (2.19-95.92) | 0.007 |
| High vs. Low Risk | 32.16 (6.40-246.94) | 0.0001 |
| B. Predictive Performance of Risk Classes vs. GI Subspecialist Pathologist Diagnosis | | |
| Analysis without Risk Prediction Test | | |
| GI Subspecialist Pathologist's Dx (LGD vs. | 28.0 (9.47-96.63) | <0.0001 |
| Analysis with Risk Prediction Test | | |
| GI Subspecialist Pathologist's Dx (LGD vs. | 10.36 (2.85-42.46) | 0.0006 |
| Risk Classes (predicted by the test) | | |
| Intermediate vs. Low Risk | 5.16 (1.34-20.34) | 0.01 |
| High vs. Low Risk | 24.65 (7.15-96.58) | <0.0001 |

Multivariate logistic regressions were run in which subsequent diagnosis of HGD/EAC as the dependent variable was evaluated first in relation to pathologic diagnosis alone, then in relation to risk classes and pathologic diagnosis, included as the independent variable in non-progressors and prevalent cases. Variables were dichotomized; diagnosis: LGD vs. ND/IND combined, predicted risk classes: intermediate- vs. low-risk class and high- vs. low-risk class.
Part A, n = 130 patients with generalist diagnosis recorded during surveillance.
Part B, n = 175 patients with GI subspecialist diagnosis provided for this study.

The teachings of all patents, published applications and references cited herein are incorporated by reference in their entirety and for the purpose for which they are being incorporated, which can be inferred from the context if not explicit.

While the embodiments have been described with references to example embodiments thereof, it will be understood by those skilled in the art that various changes in form and details may be made and be within the scope of what is described and claimed herein.

What is claimed is:

1. A method of determining a risk of progression of Barrett's esophagus in a subject, comprising:
   a) obtaining an upper gastrointestinal sample from the subject;
   b) labeling cell nuclei in the sample with a panel of reagents;
   c) labeling a plurality of biomarkers in the sample, wherein the plurality of biomarkers are p53, HIF-1α, COX2, p16, alpha-methylacyl-CoA racemase (AMACR), CD68, CD45RO, K20, and HER2/neu;
   d) detecting the labeled plurality of biomarkers and cell nuclei with an optical scanner;
   e) generating digital image data from the detected labeled plurality of biomarkers and cell nuclei;
   f) analyzing the labeled sample using a digital image platform for multi-channel fluorescence whole slide imaging to produce high dimensional quantitative image analysis features;
   g) analyzing the image analysis features associated with the plurality of biomarkers and cell nuclei, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity;
   h) determining a score using the combination of the image analysis features; and
   i) correlating the score to the risk of progression of Barrett's esophagus in the subject; wherein the score of 0 to less than 5.5 indicates a low risk of progression of Barrett's esophagus, the score of greater than or equal to 5.5 to less than 6.4 indicates an intermediate risk of progression of Barrett's esophagus, and the score of greater than or equal to 6.4 to 10 indicates a high risk of progression of Barrett's esophagus; and wherein the subject that is identified as having an intermediate risk or high risk score of progression of Barrett's esophagus is treated with an endoscopic ablation therapy, endoscopic photodynamic therapy, endoscopic cryotherapy, endoscopic mucosal resection, a surgical resection therapy, a non-endoscopic surgical therapy, or systemic therapy; and wherein the subject that is identified as having a low risk of progression has surveillance with reduced frequency.

2. The method of claim 1, wherein the subject having the immediate risk or the high risk score has an increased risk of progression to non-dysplastic intestinal metaplasia, reactive atypia, indefinite for dysplasia, low grade dysplasia, high grade dysplasia, or esophageal cancer.

3. The method of claim 1, wherein detecting the plurality of biomarkers comprises using probes that specifically bind to each of the biomarkers, and wherein the probes are fluorescent, comprise a fluorescent tag, are detected via a secondary fluorescent probe, or are detected via a secondary fluorescently tagged probes, and wherein each probe is labeled with a different fluorophore.

4. The method of claim 1, wherein the labeled plurality of biomarkers and cell nuclei are imaged to produce fields of view that are analyzed to extract features associated with biomarkers and morphology.

5. The method of claim 1, wherein the cell nuclei are labeled with a panel of reagents selected from the group consisting of Hoechst 33258, Hoechst 33342, Hoechst 34580, 4', 6'-diamidino-2-phenylindole (DAPI), cyanine nucleic acid stains, and hematoxylin.

6. The method of claim 1, wherein the score is used to determine the frequency of endoscopic surveillance in a subject with Barrett's esophagus or wherein a low risk score results in a treatment of reduced surveillance frequency in a subject with Barrett's esophagus.

7. The method of claim 1, wherein the score is used to determine whether a patient is a candidate for therapeutic intervention to prevent progression of Barrett's esophagus, and wherein the therapeutic intervention is an endoscopic ablation therapy, endoscopic photodynamic therapy, endoscopic cryotherapy, endoscopic mucosal resection, a surgical resection therapy, a non-endoscopic surgical therapy, or systemic therapy.

8. A method of classifying Barrett's esophagus in a subject, comprising:
- a) obtaining an upper gastrointestinal sample from the subject;
- b) labeling cell nuclei in the sample with a panel of reagents;
- c) labeling a plurality of biomarkers in the sample, wherein the plurality of biomarkers are p53, HIF-1α, COX2, p16, alpha-methylacyl-CoA racemase (AMACR), CD68, CD45RO, K20, and HER2/neu;
- d) detecting the labeled plurality of biomarkers and cell nuclei with an optical scanner;
- e) generating digital image data from the detected labeled plurality of biomarkers and cell nuclei;
- f) analyzing the labeled sample using a digital image platform for multi-channel fluorescence whole slide imaging to produce high dimensional quantitative image analysis features;
- g) analyzing the image analysis features associated with the plurality of biomarkers and cell nuclei, wherein the image analysis features are p53 nuclear sum intensity, p53 nuclear mean intensity, ratio of mean HER2/neu intensity:mean K20 intensity in nuclei clusters, ratio of 95th quantile HER2/neu intensity:95th quantile K20 intensity in nuclei clusters, coexpression cellular COX2 and CD68, p53 mean intensity in nuclei clusters, nuclear solidity in p53-overexpressing p16-negative cells, CD45RO plasma membrane sum intensity, AMACR microenvironment standard deviation, COX2 texture in cytoplasm, HIF-1α microenvironment cell mean intensity, HIF-1α microenvironment cell moment (product of mean and standard deviation), p16 cytoplasm mean intensity, nuclear area in p53-overexpressing p16-negative cells, and Hoechst nuclear 95th quantile intensity;
- h) determining a score using the combination of the image analysis features; and
- i) correlating the score to a classification of Barrett's esophagus; wherein the score classifies the Barrett's esophagus as low-risk, intermediate-risk or high-risk; wherein the low-risk classification of Barrett's esophagus comprises identifying patients at very low risk of progressing to high grade dysplasia or esophageal cancer within 5 years and further comprises extending the frequency of endoscopic surveillance up to 5 years for said patients and wherein the intermediate risk or high-risk classification of Barrett's esophagus comprises intervention with an endoscopic ablation therapy, endoscopic photodynamic therapy, endoscopic cryotherapy, endoscopic mucosal resection, a surgical resection therapy, a non-endoscopic surgical therapy, or systemic therapy.

9. The method of claim 8, wherein detecting the plurality of biomarkers comprises using probes that specifically bind to each of the biomarkers, and wherein the probes are fluorescent, comprise a fluorescent tag, are detected via a secondary fluorescent probe, or are detected via secondary fluorescently tagged probes, and wherein each probe is labeled with a different fluorophore.

10. The method of claim 8, wherein the labeled plurality of biomarkers and cell nuclei are imaged to produce fields of view that are analyzed to extract features associated with biomarkers and morphology.

11. The method of claim 8, wherein the cell nuclei are labeled with a panel of reagents selected from the group consisting of Hoechst 33258, Hoechst 33342, Hoechst 34580, 4', 6'-diamidino-2-phenylindole (DAPI), cyanine nucleic acid stains, and hematoxylin.

* * * * *